United States Patent
Choi et al.

(10) Patent No.: US 10,858,395 B2
(45) Date of Patent: *Dec. 8, 2020

(54) SKIN-PENETRATING PEPTIDE AND METHOD FOR USING SAME

(71) Applicant: IUCF-HYU (INDUSTRY-UNIVERSITY COOPERATION FOUNDATION HANYANG UNIVERSITY), Seoul (KR)

(72) Inventors: Je-Min Choi, Seoul (KR); Wonju Kim, Seoul (KR); Ja-Hyun Koo, Seoul (KR); Jiyun Kim, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/759,134

(22) PCT Filed: Sep. 9, 2016

(86) PCT No.: PCT/KR2016/010176
§ 371 (c)(1),
(2) Date: Mar. 9, 2018

(87) PCT Pub. No.: WO2017/043920
PCT Pub. Date: Mar. 16, 2017

(65) Prior Publication Data
US 2019/0055285 A1    Feb. 21, 2019

(30) Foreign Application Priority Data

Sep. 10, 2015   (KR) ................. 10-2015-0128275
Sep. 9, 2016   (KR) ................. 10-2016-0116282

(51) Int. Cl.

| | |
|---|---|
| *C07K 7/06* | (2006.01) |
| *A61K 8/64* | (2006.01) |
| *C07K 7/08* | (2006.01) |
| *C07K 19/00* | (2006.01) |
| *A61Q 19/00* | (2006.01) |
| *A61P 17/06* | (2006.01) |
| *A61P 17/00* | (2006.01) |
| *A61K 9/00* | (2006.01) |
| *C12N 9/16* | (2006.01) |
| *A61K 38/00* | (2006.01) |

(52) U.S. Cl.
CPC ................. *C07K 7/06* (2013.01); *A61K 8/64* (2013.01); *A61K 9/0014* (2013.01); *A61P 17/00* (2018.01); *A61P 17/06* (2018.01); *A61Q 19/00* (2013.01); *C07K 7/08* (2013.01); *C07K 19/00* (2013.01); *C12N 9/16* (2013.01); *C12Y 301/03048* (2013.01); *A61K 38/00* (2013.01); *C07K 2319/00* (2013.01)

(58) Field of Classification Search
CPC ........ A61K 38/00; A61K 8/64; A61K 9/0014; A61P 17/00; A61P 17/06; A61Q 19/00; C07K 19/00; C07K 2319/00; C07K 7/06; C07K 7/08; C12N 9/16; C12Y 301/03048
See application file for complete search history.

(56) References Cited

U.S. PATENT DOCUMENTS

| | | | | |
|---|---|---|---|---|
| 6,656,700 | B2 * | 12/2003 | Gu .................. | G16B 30/00 506/14 |
| 6,770,740 | B1 * | 8/2004 | Rice .................. | A61K 47/645 530/300 |
| 9,969,774 | B2 * | 5/2018 | Choi .................. | C07K 14/43595 |
| 2005/0196754 | A1 * | 9/2005 | Drmanac .............. | C07K 14/47 435/6.11 |
| 2009/0305900 | A1 * | 12/2009 | Belouchi ............. | C12Q 1/6883 506/7 |
| 2010/0186127 | A1 * | 7/2010 | Byrum ................ | C07K 14/415 800/298 |
| 2011/0033389 | A1 * | 2/2011 | Chen .................. | C07K 16/087 424/9.6 |
| 2015/0025221 | A1 | 1/2015 | Hsu et al. | |

FOREIGN PATENT DOCUMENTS

| | | | | |
|---|---|---|---|---|
| KR | 10-2012-0034927 | | 4/2012 | |
| KR | 10-2012-0104036 | | 9/2012 | |
| KR | 10-2013-0045143 | | 5/2013 | |
| KR | 10-20130135207 | | 12/2013 | |
| WO | WO2012113513 | * | 8/2012 | ............. A61K 47/48 |
| WO | 2012/150960 | | 11/2012 | |
| WO | W02012150960 | * | 11/2012 | ............. A61K 47/48 |
| WO | WO2012/150960 | * | 11/2012 | ............. A61K 47/48 |
| WO | 2015/137705 | | 9/2015 | |
| WO | WO2017/043920 | | 3/2017 | |

OTHER PUBLICATIONS

UniprotKB—L5KZJ6 (L5KZJ6_PTEAL) accessed online at http://www.uniprot.org/uniprot/L5KZJ6 on Jun. 5, 2017, 2 pages. (Year: 2017).*

(Continued)

*Primary Examiner* — Marcela M Cordero Garcia
(74) *Attorney, Agent, or Firm* — Sughrue Mion, PLLC

(57) ABSTRACT

The present disclosure is directed to providing a new skin-penetrating peptide, a fusion product with a biologically active substance bound using the same, a cosmetic composition containing the same and a pharmaceutical composition for external application to skin containing the same. The skin-penetrating peptide of the present disclosure is less likely to cause an immune response as compared to existing skin-penetrating peptides and exhibits remarkably improved skin permeability. Therefore, the biologically active substance can be effectively delivered through the skin, particularly through the stratum corneum.

15 Claims, 38 Drawing Sheets

Specification includes a Sequence Listing.

(56) References Cited

OTHER PUBLICATIONS

Uhlig et al. The emergence of peptides in the pharmaceutical business: From exploartion to exploitation. EuPA Open Proteomics, vol. 4, pp. 58-69. (Year: 2014).*

Desai et al., "Interaction of nanoparticles and cell-penetrating peptides with skin for transdermal drug delivery", Molecular Membrane Biology, 27:7, 247-259, DOI: 10.3109/09687688.2010.522203 yr: 2010.

Wang et al., "Recent progress of cell-penetrating peptides as new carriers for intracellular cargo delivery", Journal of Controlled Release 174 (2014) 126-136.

Bouwstra et al., "Structure of the skin barrier and its modulation by vesicular formulations", Progress in Lipid Research 42 (2003) 1-36.

Daftarian et al., "Rejection of large HPV-16 expressing tumors in aged mice by a single immunization of VacciMax® encapsulated CTL/T helper peptides", Journal of Translational Medicine 2007, 5:26, pp. 1-9.

Fawell et al., "Tat-mediated delivery of heterologous proteins into cells", Proc. Natl. Acad. Sci., vol. 91, pp. 664-668, Jan. 1994, Cell Biology.

International Search Report for PCT/KR2016/010176, dated Nov. 22, 2016, 3 pages.

Kawamura et al., "In Vivo Generation of Cytotoxic T Cells from Epitopes Displayed on Peptide-Based Delivery Vehicles", J. Immunol 2002; 168:5709-5715.

Kim et al., "Transduced PEP-1-FK506BP Ameliorates Atopic Dermatitis in NC/Nga Mice", Journal of Investigative Dermatology (2011) 131, 1477-1485.

Langdon et al., "Oncostatin M Regulates Eotaxin Expression in Fibroblasts and Eosinophilic Inflammation in C57BL/6 Mice", J Immunol 2003; 170:548-555.

Lee et al., "Evaluation of a Highly Skin Permeable Low-Molecular-Weight Protamine Conjugated Epidermal Growth Factor for Novel Burn Wound Healing Therapy", Journal of Pharmaceutical Sciences 102:4109-4120, 2013.

Mehta et al., "Endogenous growth factors as cosmeceuticals", Dermatologic Therapy, vol. 20, 2007, 350-359.

Prausnitz et al., "Transdermal drug delivery", Nature Biotechnology, vol. 26, No. 11, Nov. 2008, pp. 1261-1268.

Song et al., "Topical transduction of superoxide dismutase mediated by HIV-1 Tat protein transduction domain ameliorates 12-0-tetradecanoylphorbol-13-acetate (TPA)-induced inflammation in mice", Biochemical Pharmacology 75 (2008) 1348-1357.

Sutmuller et al., "Adoptive T Cell Immunotherapy of Human Uveal Melanoma Targeting gp100", J. Immunol 2000; 165:7308-7315.

Wadia et al., "Transducibel TAT-HA fusogenic peptide enhances escape of TAT-fusion proteins after lipid raft micropinocytosis", Nature Medicine, vol. 10, No. 3, Mar. 2004, pp. 310-315.

* cited by examiner

M; Marker
1; EGFP
2; TAT-EGFP
3; AP-EGFP

FIG. 17
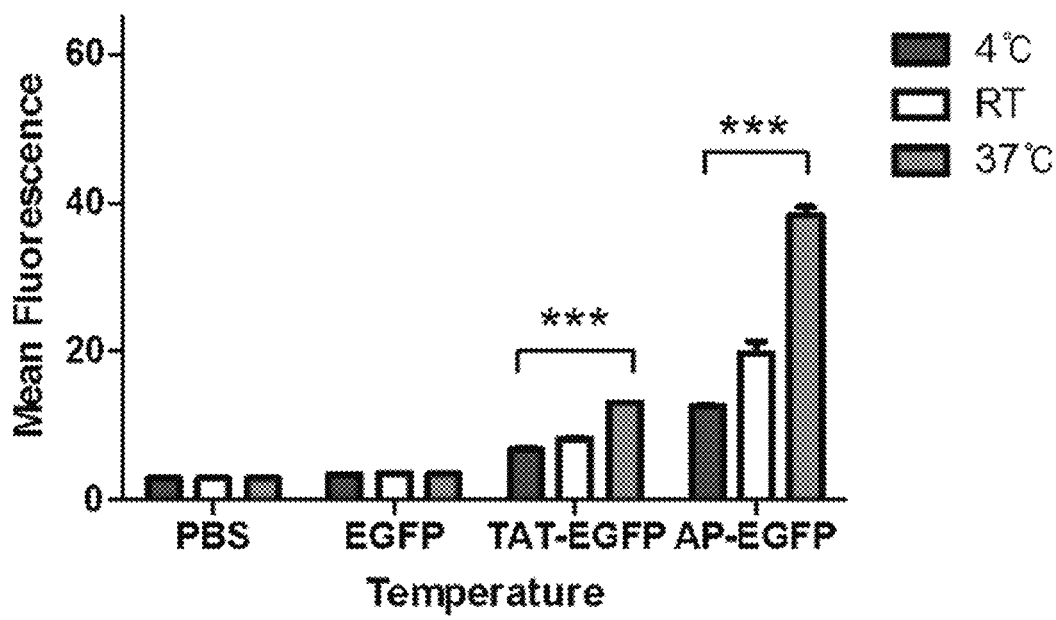
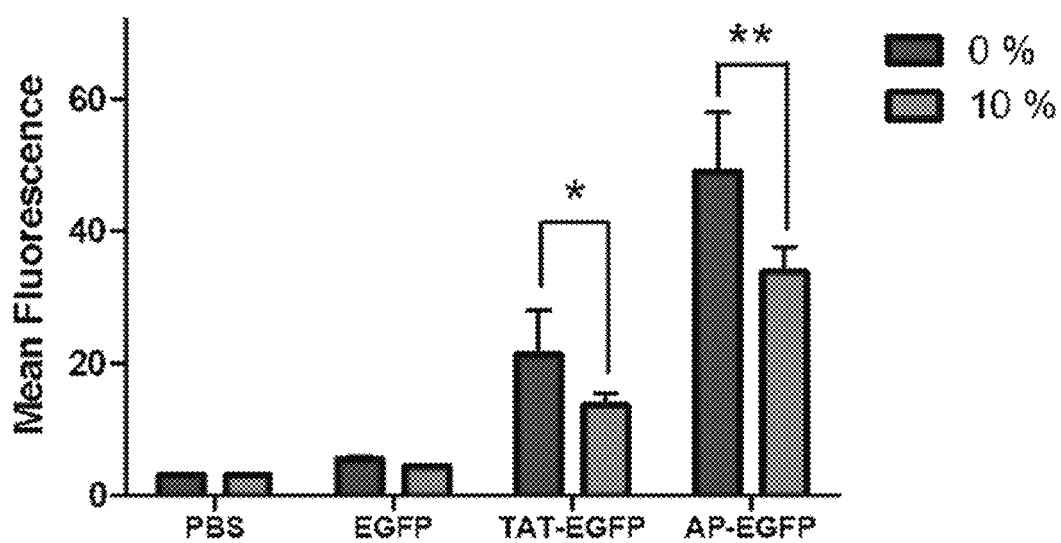

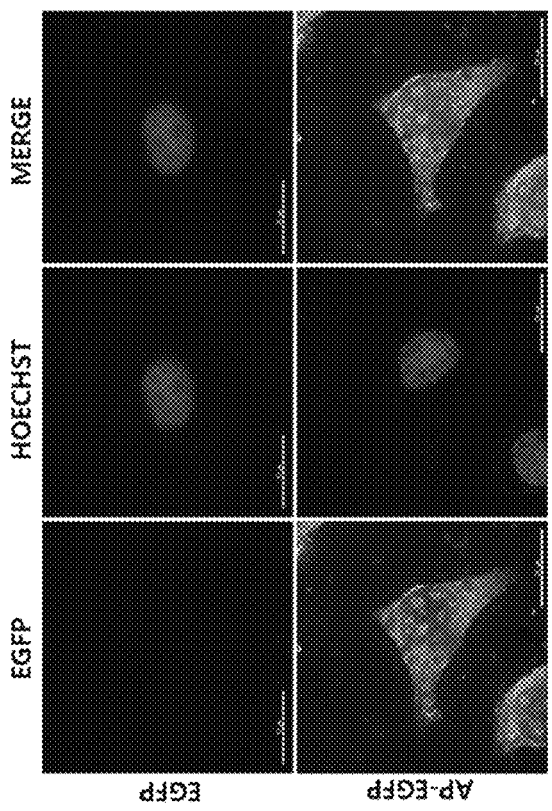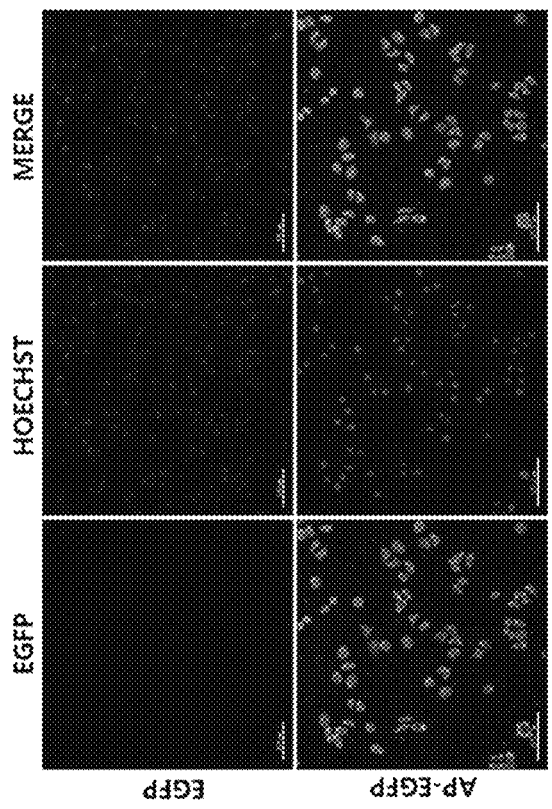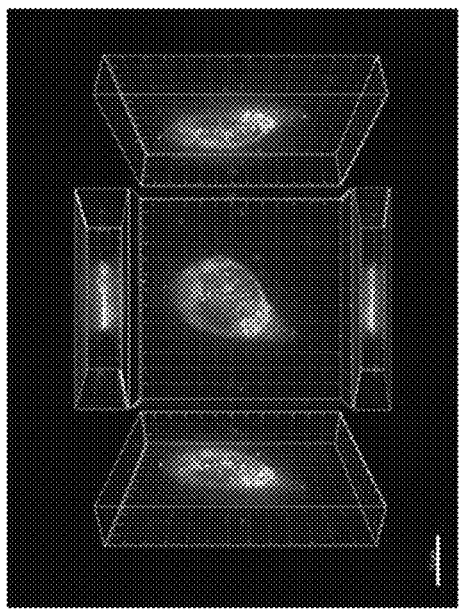
FIG. 19

1 : AP-PTPN2
2 : AP-EGFP

TC-PTP phosphatase domain
(5-275)

FIG. 45
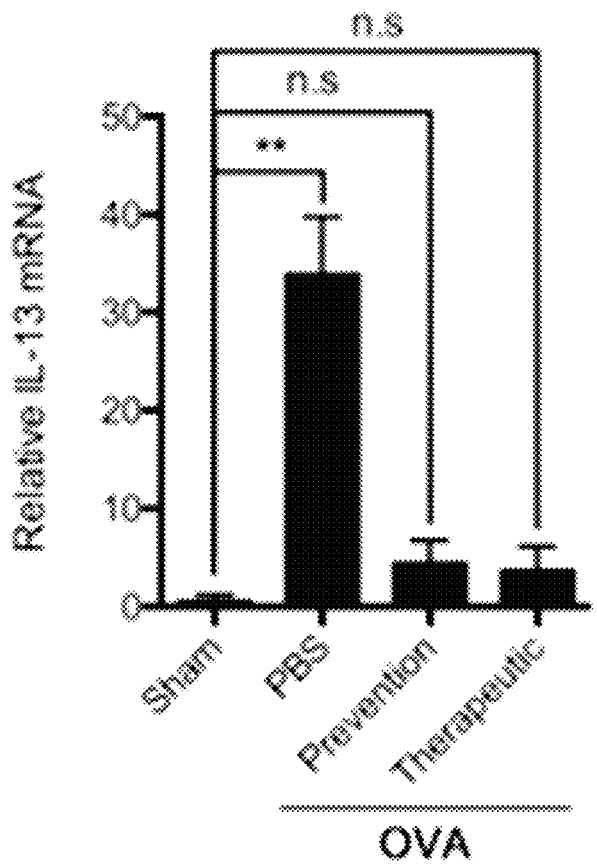
【FIG. 46】
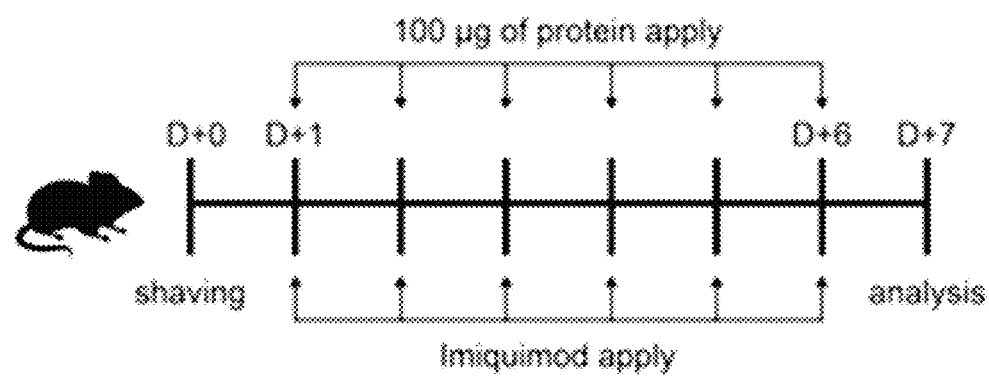

SEQUENCE LISTING

```
<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: synthetic

<400> SEQUENCE: 1

Arg Arg Arg Trp Cys Lys Arg Arg Arg
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Arg Arg Trp Cys Lys Arg Arg Arg
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

Arg Arg Arg Trp Cys Lys Arg Arg
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic

<400> SEQUENCE: 4

Arg Arg Trp Cys Lys Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic

<400> SEQUENCE: 5

Arg Arg Arg Ala Cys Lys Arg Arg Arg
1               5

<210> SEQ ID NO 6
<211> LENGTH: 9
<212> TYPE: PRT
```

```
<213> ORGANISM: Artificial Sequence
<220> FEATURE:
<223> OTHER INFORMATION: synthetic

<400> SEQUENCE: 6

Arg Arg Arg Trp Ala Lys Arg Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: synthetic

<400> SEQUENCE: 7

Arg Arg Arg Trp Cys Ala Arg Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic

<400> SEQUENCE: 8

Arg Arg Arg Arg Cys Lys Arg Arg Arg
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic

<400> SEQUENCE: 9

Arg Arg Arg Trp Arg Lys Arg Arg Arg
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic

<400> SEQUENCE: 10

Arg Arg Arg Trp Cys Arg Arg Arg Arg
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic

<400> SEQUENCE: 11

Arg Arg Arg Arg Arg Arg Arg Arg Arg
1               5

<210> SEQ ID NO 12
<211> LENGTH: 9
<212> TYPE: PRT
<213> ORGANISM: Artificial Sequence
```

```
<220> FEATURE:
<223> OTHER INFORMATION: synthetic

<400> SEQUENCE: 12

Arg Arg Arg Arg Cys Arg Arg Arg Arg
1               5

<210> SEQ ID NO 13
<211> LENGTH: 68
<212> TYPE: DNA
<213> ORGANISM: Artificial Sequence
<220> FEATURE:
<223> OTHER INFORMATION: EGFP forward primer

<400> SEQUENCE: 13
ctagctagcc gccggcgctg gtgcaaacgc cgccggggat ccgtgagcaa gggcgaggag    60
ctgttcac                                                             68

<210> SEQ ID NO 14
<211> LENGTH: 25
<212> TYPE: DNA
<213> ORGANISM: Artificial Sequence
<220> FEATURE:
<223> OTHER INFORMATION: EGFP reverse primer

<400> SEQUENCE: 14 caagcttttta cttgtatagc tcgtc                                         25

<210> SEQ ID NO 15
<211> LENGTH: 12
<212> TYPE: PRT
<213> ORGANISM: Artificial Sequence
<220> FEATURE:
<223> OTHER INFORMATION: synthetic

<400> SEQUENCE: 15

Asn Gly Ser Leu Asn Thr His Leu Ala Pro Ile Leu
1               5                   10

<210> SEQ ID NO 16
<211> LENGTH: 262
<212> TYPE: PRT
<213> ORGANISM: Artificial Sequence
<220> FEATURE:
<223> OTHER INFORMATION: synthetic

<400> SEQUENCE: 16

Met Arg Gly Ser His His His His His His Gly Met Ala Ser Asn Gly
1               5                   10                  15

Ser Leu Asn Thr His Leu Ala Pro Ile Leu Gly Ser Met Val Ser Lys
            20                  25                  30

Gly Glu Glu Val Ile Lys Glu Phe Met Arg Phe Lys Val Arg Met Glu
        35                  40                  45

Gly Ser Met Asn Gly His Glu Phe Glu Ile Glu Gly Glu Gly Glu Gly
    50                  55                  60

Arg Pro Tyr Glu Gly Thr Gln Thr Ala Lys Leu Lys Val Thr Lys Gly
65                  70                  75                  80

Gly Pro Leu Pro Phe Ala Trp Asp Ile Leu Ser Pro Gln Phe Met Tyr
                85                  90                  95

Gly Ser Lys Ala Tyr Val Lys His Pro Ala Asp Ile Pro Asp Tyr Lys
            100                 105                 110

Lys Leu Ser Phe Pro Glu Gly Phe Lys Trp Glu Arg Val Met Asn Phe
```

```
            115                 120                 125
Glu Asp Gly Gly Leu Val Thr Val Thr Gln Asp Ser Ser Leu Gln Asp
130                 135                 140
Gly Thr Leu Ile Tyr Lys Val Lys Met Arg Gly Thr Asn Phe Pro Pro
145                 150                 155                 160
Asp Gly Pro Val Met Gln Lys Lys Thr Met Gly Trp Glu Ala Ser Thr
                165                 170                 175
Glu Arg Leu Tyr Pro Arg Asp Gly Val Leu Lys Gly Glu Ile His Gln
            180                 185                 190
Ala Leu Lys Leu Lys Asp Gly Gly His Tyr Leu Val Glu Phe Lys Thr
        195                 200                 205
Ile Tyr Met Ala Lys Lys Pro Val Gln Leu Pro Gly Tyr Tyr Tyr Val
    210                 215                 220
Asp Thr Lys Leu Asp Ile Thr Ser His Asn Glu Asp Tyr Thr Ile Val
225                 230                 235                 240
Glu Gln Tyr Glu Arg Ser Glu Gly Arg His His Leu Phe Leu Tyr Gly
                245                 250                 255
Met Asp Glu Leu Tyr Lys
            260

<210> SEQ ID NO 17
<211> LENGTH: 10
<212> TYPE: PRT
<213> ORGANISM: Artificial Sequence
<220> FEATURE:
<223> OTHER INFORMATION: synthetic

<400> SEQUENCE: 17

Met Arg Ala Ala Ala Pro Ala Val Ala Ala
1               5                   10

<210> SEQ ID NO 18
<211> LENGTH: 260
<212> TYPE: PRT
<213> ORGANISM: Artificial Sequence
<220> FEATURE:
<223> OTHER INFORMATION: synthetic

<400> SEQUENCE: 18

Met Arg Gly Ser His His His His His His Gly Met Ala Ser Met Arg
1               5                   10                  15
Ala Ala Ala Pro Ala Val Ala Ala Gly Ser Met Val Ser Lys Gly Glu
            20                  25                  30
Glu Val Ile Lys Glu Phe Met Arg Phe Lys Val Arg Met Glu Gly Ser
        35                  40                  45
Met Asn Gly His Glu Phe Glu Ile Glu Gly Glu Gly Glu Gly Arg Pro
    50                  55                  60
Tyr Glu Gly Thr Gln Thr Ala Lys Leu Lys Val Thr Lys Gly Gly Pro
65                  70                  75                  80
Leu Pro Phe Ala Trp Asp Ile Leu Ser Pro Gln Phe Met Tyr Gly Ser
                85                  90                  95
Lys Ala Tyr Val Lys His Pro Ala Asp Ile Pro Asp Tyr Lys Lys Leu
            100                 105                 110
Ser Phe Pro Glu Gly Phe Lys Trp Glu Arg Val Met Asn Phe Glu Asp
        115                 120                 125
Gly Gly Leu Val Thr Val Thr Gln Asp Ser Ser Leu Gln Asp Gly Thr
    130                 135                 140
```

```
Leu Ile Tyr Lys Val Lys Met Arg Gly Thr Asn Phe Pro Pro Asp Gly
145                 150                 155                 160

Pro Val Met Gln Lys Lys Thr Met Gly Trp Glu Ala Ser Thr Glu Arg
            165                 170                 175

Leu Tyr Pro Arg Asp Gly Val Leu Lys Gly Glu Ile His Gln Ala Leu
        180                 185                 190

Lys Leu Lys Asp Gly Gly His Tyr Leu Val Glu Phe Lys Thr Ile Tyr
    195                 200                 205

Met Ala Lys Lys Pro Val Gln Leu Pro Gly Tyr Tyr Val Asp Thr
210                 215                 220

Lys Leu Asp Ile Thr Ser His Asn Glu Asp Tyr Thr Ile Val Glu Gln
225                 230                 235                 240

Tyr Glu Arg Ser Glu Gly Arg His His Leu Phe Leu Tyr Gly Met Asp
            245                 250                 255

Glu Leu Tyr Lys
            260

<210> SEQ ID NO 19
<211> LENGTH: 313
<212> TYPE: PRT
<213> ORGANISM: Artificial Sequence
<220> FEATURE:
<223> OTHER INFORMATION: synthetic

<400> SEQUENCE: 19

Met Gly Ser Ser His His His His His His Ser Ser Gly Leu Val Pro
1               5                   10                  15

Arg Gly Ser His Met Ala Ser Arg Arg Arg Trp Cys Lys Arg Arg Arg
            20                  25                  30

Glu Phe Ile Glu Arg Glu Phe Glu Glu Leu Asp Ala Gln Cys Arg Trp
        35                  40                  45

Gln Pro Leu Tyr Leu Glu Ile Arg Asn Glu Ser His Asp Tyr Pro His
    50                  55                  60

Arg Val Ala Lys Phe Pro Glu Asn Arg Asn Arg Tyr Arg Asp
65                  70                  75                  80

Val Ser Pro Tyr Asp His Ser Arg Val Lys Leu Gln Ser Thr Glu Asn
                85                  90                  95

Asp Tyr Ile Asn Ala Ser Leu Val Asp Ile Glu Glu Ala Gln Arg Ser
            100                 105                 110

Tyr Ile Leu Thr Gln Gly Pro Leu Pro Asn Thr Cys Cys His Phe Trp
        115                 120                 125

Leu Met Val Trp Gln Gln Lys Thr Lys Ala Val Val Met Leu Asn Arg
    130                 135                 140

Thr Val Glu Lys Glu Ser Val Lys Cys Ala Gln Tyr Trp Pro Thr Asp
145                 150                 155                 160

Asp Arg Glu Met Val Phe Lys Glu Thr Gly Phe Ser Val Lys Leu Leu
                165                 170                 175

Ser Glu Asp Val Lys Ser Tyr Tyr Thr Val His Leu Leu Gln Leu Glu
            180                 185                 190

Asn Ile Asn Thr Gly Glu Thr Arg Thr Ile Ser His Phe His Tyr Thr
        195                 200                 205

Thr Trp Pro Asp Phe Gly Val Pro Glu Ser Pro Ala Ser Phe Leu Asn
    210                 215                 220

Phe Leu Phe Lys Val Arg Glu Ser Gly Cys Leu Thr Pro Asp His Gly
225                 230                 235                 240
```

```
Pro Ala Val Ile His Cys Ser Ala Gly Ile Gly Arg Ser Gly Thr Phe
                    245                 250                 255

Ser Leu Val Asp Thr Cys Leu Val Leu Met Glu Lys Gly Glu Asp Val
            260                 265                 270

Asn Val Lys Gln Leu Leu Leu Asn Met Arg Lys Tyr Arg Met Gly Leu
        275                 280                 285

Ile Gln Thr Pro Asp Gln Leu Arg Phe Ser Tyr Met Ala Ile Ile Glu
    290                 295                 300

Gly Leu Glu His His His His His His
305                 310

<210> SEQ ID NO 20
<211> LENGTH: 271
<212> TYPE: PRT
<213> ORGANISM: Artificial Sequence
<220> FEATURE:
<223> OTHER INFORMATION: synthetic

<400> SEQUENCE: 20

Ile Glu Arg Glu Phe Glu Leu Asp Ala Gln Cys Arg Trp Gln Pro
1               5                   10                  15

Leu Tyr Leu Glu Ile Arg Asn Glu Ser His Asp Tyr Pro His Arg Val
            20                  25                  30

Ala Lys Phe Pro Glu Asn Arg Asn Arg Asn Arg Tyr Arg Asp Val Ser
        35                  40                  45

Pro Tyr Asp His Ser Arg Val Lys Leu Gln Ser Thr Glu Asn Asp Tyr
    50                  55                  60

Ile Asn Ala Ser Leu Val Asp Ile Glu Glu Ala Gln Arg Ser Tyr Ile
65                  70                  75                  80

Leu Thr Gln Gly Pro Leu Pro Asn Thr Cys Cys His Phe Trp Leu Met
                85                  90                  95

Val Trp Gln Gln Lys Thr Lys Ala Val Val Met Leu Asn Arg Thr Val
            100                 105                 110

Glu Lys Glu Ser Val Lys Cys Ala Gln Tyr Trp Pro Thr Asp Asp Arg
        115                 120                 125

Glu Met Val Phe Lys Glu Thr Gly Phe Ser Val Lys Leu Leu Ser Glu
    130                 135                 140

Asp Val Lys Ser Tyr Tyr Thr Val His Leu Leu Gln Leu Glu Asn Ile
145                 150                 155                 160

Asn Thr Gly Glu Thr Arg Thr Ile Ser His Phe His Tyr Thr Thr Trp
                165                 170                 175

Pro Asp Phe Gly Val Pro Glu Ser Pro Ala Ser Phe Leu Asn Phe Leu
            180                 185                 190

Phe Lys Val Arg Glu Ser Gly Cys Leu Thr Pro Asp His Gly Pro Ala
        195                 200                 205

Val Ile His Cys Ser Ala Gly Ile Gly Arg Ser Gly Thr Phe Ser Leu
    210                 215                 220

Val Asp Thr Cys Leu Val Leu Met Glu Lys Gly Glu Asp Val Asn Val
225                 230                 235                 240

Lys Gln Leu Leu Leu Asn Met Arg Lys Tyr Arg Met Gly Leu Ile Gln
                245                 250                 255

Thr Pro Asp Gln Leu Arg Phe Ser Tyr Met Ala Ile Ile Glu Gly
            260                 265                 270

<210> SEQ ID NO 21
<211> LENGTH: 63
```

-continued

```
<212> TYPE: DNA
<213> ORGANISM: Artificial Sequence
<220> FEATURE:
<223> OTHER INFORMATION: AP-rPTP forward primer

<400> SEQUENCE: 21
ctagctagcc gccggcgctg gtgcaaacgc cgccggggat ccgaattcat cgagcgggag      60
ttc                                                                   63

<210> SEQ ID NO 22
<211> LENGTH: 23
<212> TYPE: DNA
<213> ORGANISM: Artificial Sequence
<220> FEATURE:
<223> OTHER INFORMATION: AP-rPTP reverse primer

<400> SEQUENCE: 22
ccgctcgagt ccttctatta tgg                                             23
```

SKIN-PENETRATING PEPTIDE AND METHOD FOR USING SAME

CROSS-REFERENCE TO RELATED APPLICATION

This application claims priority to and is a 35 U.S.C. § 371 national phase application of PCT/KR2016/010176 (WO2017/043920), filed on Sep. 9, 2016 entitled "SKIN PERMEABLE PEPTID AND METHOD FOR USING SAME", which application claims priority to and the benefit of Korean Patent Application No. 10-2015-0128275, filed Sep. 10, 2015 and Korean Patent Application No. 10-2016-0116282, filed Sep. 9, 2016; the disclosures of which is incorporated herein by reference in their entirety.

SEQUENCE STATEMENT

Incorporated by reference herein in its entirety is the Sequence Listing entitled "PCT461-ST25.txt," created Mar. 9, 2018, size of 14 kilobyte.

TECHNICAL FIELD

The present disclosure relates to a skin-penetrating peptide capable of delivering a biologically active substance through skin, a derivative thereof, a pharmaceutical composition for external application to skin containing the peptide or the derivative thereof and a cosmetic composition containing the peptide or the derivative thereof.

BACKGROUND ART

Skin is the tissue which is constantly in contact with the external environment. It functions as a protective barrier that prevents leakage of body fluid, infection and water loss. Especially, the stratum corneum of the epidermis, which is the outermost layer of the skin, prevents skin dryness by preventing loss of water and electrolytes out of the skin and protects the human body from physical damage and chemicals from outside by providing an environment for normal biochemical metabolism of the skin. In addition, it plays an important role of preventing the invasion of bacteria, fungi, viruses, etc. into the skin (Bouwstra J. A, Honeywell-Nguyen P. L. Gooris G. S. and Ponec M. *Prog Lipid Res.* 42: 1-36 (2003)).

The routes of absorption through the skin include absorption through the stratum corneum, absorption through hair follicles and sebaceous glands and absorption through sweat glands (Prausnitz M. R. and Langer R. *Nat Biotech.* 26: 1261-1268 (2008)). The delivery of physiologically active molecules through the skin is restricted by the structural and physical characteristics of the skin. At present, the absorption through the stratum corneum is known as the most important route of absorption. Especially, the stratum corneum of the skin, which is formed as keratinocyte are transformed into non-living corneocytes, is the outermost layer with a dense structure. It prevents evaporation of water and invasion of foreign materials and exhibits acidity with pH of around 5 due to sweat and various lipid components. For a material to penetrate the barrier of the stratum corneum, it should have a molecular weight of 500 Da or smaller as well as lipophilicity (Metha R. C. and Fitzpatrick R. E. *Dermatol. Ther.* 20: 350-359 (2007)).

Although it is known that low-molecular-weight synthetic compounds or natural compounds with a molecular weight of 500 Da or smaller, which are commonly used as cosmetic ingredients, can be easily delivered into cells, the permeation efficiency of the low-molecular-weight substances is low due to the intrinsic properties of the stratum corneum constituting the skin barrier. Macromolecules with a molecular weight of 500 Da or larger, such as proteins, peptides and nucleic acids, are more difficult to penetrate into the cell membrane consisting of a lipid bilayer structure due to their large molecular weight. As a method for improving the permeation efficiency of the low-molecular-weight substances and macromolecules through the plasma membrane of cells, interests in transdermal drug delivery (TDD) are increasing recently (Prausnitz M. R. and Langer R. *Nat Biotech.* 26: 1261-1268 (2008)). However, the biggest obstacles to the transdermal delivery are keratinocytes in the stratum corneum and intercorneocyte lipids. Because the stratum corneum of the skin is resistant to most molecules exhibiting physiological activity to the skin (hereinafter, referred to as physiologically active molecules), their transdermal permeability is low.

A variety of methods for enhancing the transdermal permeability of these physiologically active molecules have been studied. Recently, a delivery system using a cell-penetrating peptide is drawing a lot of attentions. The use of a cell-penetrating peptide has several advantages, which are mainly derived from various modifications that can be made to the sequence of the peptide. This allows for designation of other cell subdomains and manipulation of a carrier capable of carrying cargo molecules of various forms.

TAT, a representative example of the membrane-penetrating peptide, was the first protein found to penetrate the cell membrane in the HIV-1 (human immunodeficiency virus-1) infection mechanism. The TAT peptide 'YGRKKRRQRRR' derived therefrom is the most frequently used and is being actively studied (Mann, D. A. et al., *Embo J* 10: 1733-1739, 1991). The TAT peptide has been used to deliver β-galactosidase, horseradish peroxidase, RNase A, the domain of *Pseudomonas* exotoxin A (PE), etc. into cells to study their functions and localization in the cells (Fawell, S. et al., *PNAS* 91: 664-668, 1994). It has been found that the TAT peptide enters the cells by interacting with heparan sulfate on the cell membrane, followed by endocytosis wherein lipid rafts are involved (Jehangir S. W. et al., *Nature Med* 10: 310-315, 2004).

In addition, the cell-penetrating peptide penetratin (Antp), consisting of 16 amino acid sequences, which is derived from Antennapedia homeoprotein and is an essential transcription factor in the development of fruit fly, the cell-penetrating peptide VP22 which is derived from the VP22 protein expressed by HSV-1 (herpes simplex virus type 1), the artificially synthesized transportan, consisting of 27 amino acid sequences, polyarginine obtained by artificially repeating the arginine residues expected to play the most important role in cell-penetrating peptides, etc. are well known as cell-penetrating peptides.

These existing cell-penetrating peptides may cause side effects such as immune response, etc. when used in the human body because they are derived from the proteins of viruses such as HIV-1, derived from the proteins expressed by other species such as fruit fly or artificially synthesized based on the amino acid sequence analysis of previously known cell-penetrating peptides.

In addition, they are more likely to cause unwanted immune responses because they consist of relatively long amino acid chains and the efficiency of linking to biologically active substances to be delivered into cells is often low because they may affect the structure and function of the proteins to be delivered.

The inventors of the present disclosure have demonstrated that a peptide sequence derived from the human ASTN1 (astrotactin 1) protein, which is one of neuroproteins involved in the development of the cerebellum and the migration of neurons, exhibits remarkably superior permeation efficiency into epidermal cells or skin tissues as compared to the cell-penetrating peptide TAT or previously known skin-penetrating peptides and have completed the present disclosure.

DISCLOSURE

Technical Problem

The present disclosure is directed to providing a skin-penetrating peptide for effectively introducing a physiologically active molecule, which cannot be easily delivered through skin due to its molecular weight or the intrinsic property of the stratum corneum of the skin, into skin cells, which is less likely to cause immune response and exhibits remarkably improved skin permeability as compared to existing skin-penetrating peptides.

The present disclosure is also directed to providing a peptide fusion product which solves the difficulty in preventing or treating inflammatory skin diseases through direct administration onto skin surface due to the molecular weight or the intrinsic property of the stratum corneum of the skin and, at the same time, is less likely to cause immune response and exhibits remarkably improved skin permeability as compared to existing peptides.

The present disclosure is also directed to providing a cosmetic composition for effectively preventing or treating skin diseases by administering through skin, particularly through the stratum corneum, or a pharmaceutical composition for external application to skin for preventing or treating inflammatory skin diseases.

Technical Solution

The present disclosure provides a skin-penetrating peptide having a sequence of $(X1)_n$-X2-(cysteine)-$(X3)_m$, wherein n is an integer from 3 to 14, m is an integer from 4 to 14, each of X1 and X3 is independently arginine, lysine or histidine, and X2 is alanine, glycine, proline, tryptophan, phenylalanine, leucine, isoleucine, methionine, valine, arginine, lysine or histidine.

The present disclosure also provides a fusion product in which the skin-penetrating peptide is fused with a biologically active substance.

The present disclosure also provides a recombinant expression vector comprising a gene encoding the fusion product.

The present disclosure also provides a cosmetic composition containing the fusion product as an active ingredient.

The present disclosure also provides a pharmaceutical composition for external application to skin, containing the fusion product as an active ingredient.

The present disclosure also provides a method for preventing or treating an inflammatory skin disease, including a step of applying an effective amount of the pharmaceutical composition for external application to skin to the skin of a subject.

Advantageous Effects

A skin-penetrating peptide of the present disclosure can effectively deliver a protein into epidermal cells, dermal cells and skin tissues. It can deliver the protein more effectively than the existing TAT peptide or skin-penetrating peptides and can also be used usefully for delivery of biologically active substances such as proteins, genetic materials, chemical compounds, etc. which are delivered through skin and used for therapeutic purposes.

A fusion product according to the present disclosure can be effectively delivered into epidermal cells, dermal cells and skin tissues and can inhibit not only various inflammatory cytokine signaling causing skin diseases but also T cell activation and proliferation at the same time. Therefore, it exhibits very superior effect in treating, preventing or improving inflammatory skin diseases or conditions.

In addition, the peptide fusion product of the present disclosure exhibits very superior stability and skin permeability and, thus, can be applied very advantageously to pharmaceuticals, quasi-drugs and cosmetics.

BRIEF DESCRIPTION OF DRAWINGS

FIG. 17 shows a result of intracellular fluorescence intensity analysis by flow cytometry in Test Example 7 comparing the change in the intracellular delivery efficiency of AP into cells depending on the change in temperature and serum concentration in a medium with that of existing cell-penetrating peptides as positive control groups.

FIG. 19 shows fluorescence microscopic images showing that AP-EGFP is delivered into HeLa cells in Test Example 9.

FIG. 45 shows a result of comparing the IL-13 mRNA expression level in the skin tissue of an animal model in Test Example 25.

FIG. 46 shows a scheme of an imiquimod-induced psoriasis-like dermatitis animal model of Test Example 26.

BEST MODE

Figure 1:
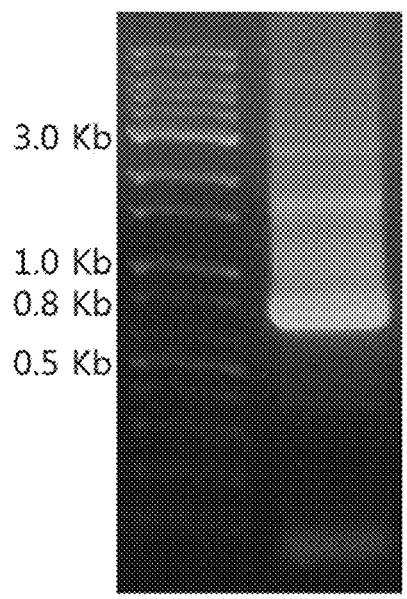
FIG. 1 shows a result of 1% agarose gel electrophoresis of a 789-bp double-stranded DNA fragment encoding AP-EGFP wherein AP is linked with EGFP of Preparation Example 2.

The present disclosure provides a skin-penetrating peptide having a sequence of $(X1)_n$-X2-(cysteine)-$(X3)_m$, wherein n is an integer from 3 to 14, specifically an integer from 3 to 6, and m is an integer from 4 to 14, specifically is an integer from 4 to 7.

The skin-penetrating peptide consists of specifically 9-14, more specifically 9-12, most specifically 9-10 amino acids. When the number of amino acids is smaller than the lower limit, cell permeation efficiency may decrease rapidly. And, if it exceeds the upper limit, the risk of immune response is increased.

In the skin-penetrating peptide, each of X1 and X3 is independently a positively charged amino acid, specifically arginine (Arg, R), lysine (Lys, K) or histidine (His, H), more specifically arginine or lysine. $(X1)_n$ is formed by n positively charged amino acids corresponding to X1. The n amino acids may be the same or different positively charged amino acids. Similarly, $(X3)_m$ is formed by m positively charged amino acids which may be different from each other.

In the skin-penetrating peptide, X2 is a nonpolar or positively charged amino acid, specifically alanine (Ala, A), glycine (Gly, G), proline (Pro, P), tryptophan (Trp, W), phenylalanine (Phe, F), leucine (Leu, L), isoleucine (Ile, I), methionine (Met, M), valine (Val, V), arginine (Arg, R), lysine (Lys, K) or histidine (His, H), more specifically alanine, tryptophan or arginine.

More specifically, the skin-penetrating peptide consists of an amino acid sequence of SEQ ID NO 1, SEQ ID NO 5, SEQ ID NO 8 or SEQ ID NO 12.

The present disclosure also provides a fusion product in which a skin-penetrating peptide is fused with a biologically active substance.

The biological activity means the activity of a substance delivered into the body or cells through skin, related with physiological phenomena or therapeutic purposes. The biologically active substance is also called a cargo because it is delivered by the skin-penetrating peptide of the present disclosure and may be a protein, a genetic material, a fat, a carbohydrate or a chemical compound.

The protein fused with the skin-penetrating peptide may include, for example, a cytokine and a receptor thereof, in addition to a chimeric protein containing a cytokine or a receptor, e.g., tumor necrosis factor-alpha and -beta, receptors thereof and derivatives thereof; renin; a growth hormone, e.g., human growth hormone, bovine growth hormone, methionine human growth hormone, desphenylalanine human growth hormone and porcine growth hormone; growth hormone-releasing factor (GRF); parathyroid and pituitary hormones; thyroid-stimulating hormone; human pancreatic hormone-releasing factor; a lipoprotein; colchicine; prolactin; corticotropin; oxytocin; vasopressin; somatostatin; terlipressin; pancreozymin; leuprolide; alpha-1-antitrypsin; insulin A-chain; insulin B-chain; proinsulin; follicle-stimulating hormone; calcitonin; luteinizing hormone; luteinizing hormone-releasing hormone (LHRH); LHRH agonist and antagonist; glucagon; a coagulation factor, e.g., factor VIIIC, factor IX, tissue factor and von Willebrand Factor; an anticoagulation factor, e.g., protein C; atrial natriuretic factor; pulmonary surfactant; plasminogen activators other than tissue plasminogen activator (t-PA), e.g., urokinase; bombesin; thrombin; hemopoietic growth factor; enkephalinase; RANTES (regulated on activation, normal T-cell expressed and secreted); human macrophage inflammatory protein (MIP-1-alpha); serum albumin such as human serum albumin; Müllerian-inhibiting substance; relaxin A-chain; relaxin B-chain; prorelaxin; mouse gonadotropin-associated peptide; chorionic gonadotropin; gonadotropin-releasing hormone; bovine somatotropin; porcine somatotropin; a microbial protein, e.g., beta-lactamase; DNase; inhibin; activin; vascular endothelial growth factor (VEGF); a receptor for a hormone or a growth factor; integrin; protein A or D; rheumatoid factor; a neurotrophic factor, e.g., bone-derived neurotrophic factor (BDNF), neurotropin-3, -4, -5 or -6 (NT-3, NT-4, NT-5 or NT-6), nerve growth factor, e.g., NGF-β; platelet-derived growth factor (PDGF); fibroblast growth factor, e.g., acidic FGF and basic FGF; epidermal growth factor (EGF); transforming growth factor (TGF), e.g., TGF-α and TGF-β including TGF-β1, TGF-β2, TGF-β3, TGF-β4 or TGF-β5; insulin-like growth factor-I and -II (IGF-I and IGF-II); des(1-3)-IGF-I (brain IGF-I), insulin-like growth factor-binding protein; a CD protein, e.g., CD-3, CD-4, CD-8 and CD-19; erythropoietin; osteoinductive factor; an immunotoxin; a bone morphogenetic protein (BMP); an interferon, e.g., interferon-α (e.g., interferon α2A), -β, -γ, -λ and consensus interferon; a colony-stimulating factor (CSF), e.g., M-CSF, GM-CSF and G-CSF; an interleukin (IL), e.g., IL-1 to IL-10; superoxide dismutase; T-cell receptor; a surface membrane protein; decay-accelerating factor; a viral antigen, e.g., a portion of the HIV-1 envelope glycoprotein, gp120, gp160 or fragments thereof; a transport protein; a homing receptor; addressin; a fertility inhibitor, e.g., prostaglandin; a fertility promoter; a regulatory protein; an antibody (including fractions thereof) and a chimeric protein, e.g., immunoadhesin; precursors, derivatives, prodrugs and analogues of these compounds, and pharmaceutically acceptable salts of these compounds, or their precursors, derivatives, prodrugs and analogues.

Specifically, the protein is a growth hormone, e.g. human growth hormone (hGH), recombinant human growth hormone (rhGH), bovine growth hormone, methionine human growth hormone, des-phenylalanine human growth hormone and porcine growth hormone; insulin, insulin A-chain, insulin B-chain and proinsulin; or a growth factor, e.g., vascular endothelial growth factor (VEGF), nerve growth factor (NGF), platelet-derived growth factor (PDGF), fibroblast growth factor (FGF), epidermal growth factor (EGF), transforming growth factor (TGF) and insulin-like growth factor-I and -II (IGF-I and IGF-II).

The biologically active substance may be a recombinant peptide (rPTP) derived from the PTPN2 protein. The rPTP peptide fused with the skin-penetrating peptide of the present disclosure may be topically applied to skin to improve or treat the symptoms of dermatitis.

The genetic material fused with the skin-penetrating peptide may be not only a nucleic acid but also a precursor, a derivative, a prodrug or an analogue thereof, for example, a therapeutic nucleotide or nucleoside and an analogue thereof; a therapeutic oligonucleotide; and a therapeutic polynucleotide.

The genetic material may find a specific use as an anticancer agent or an antiviral agent. The genetic material may be, for example, a ribozyme, an antisense oligodeoxynucleotide, an aptamer or a siRNA. Examples of an adequate nucleoside analogue include cytarabine (araCTP), gemcitabine (dFdCTP) and floxuridine (FdUTP). In addition, the genetic material may be, for example, an interfering RNA, e.g., shRNA, miRNA or siRNA. Examples of adequate siRNA include IL-7 (interleukin-7) siRNA, IL-10 (interleukin-10) siRNA, IL-22 (interleukin-22) siRNA, IL-23 (interleukin 23) siRNA, CD86 siRNA, KRT6a (keratin 6A) siRNA, K6a N171K (keratin 6a N171K) siRNA, TNFα (tumor necrosis factor α) siRNA, TNFR1 (tumor necrosis factor receptor-1) siRNA, TACE (tumor necrosis factor (TNF)-α converting enzyme) siRNA, RRM2 (ribonucleotide reductase subunit) siRNA and VEGF (vascular endothelial growth factor) siRNA. Human gene target mRNA sequences of these siRNAs are known in the art. Also, various methods and techniques for selecting specific mRNA target sequences for siRNA design are known in the art.

The fat coupled with the skin-penetrating peptide includes a fatty acid. A fatty acid is a monocarboxylic acid having a saturated or unsaturated aliphatic tail. As defined in International Cosmetic Ingredient Dictionary and Handbook, 7th Ed. (1997) volume 2, page 1567, the fatty acid has about 7 or more carbon atoms. For example, palmitic acid, which is the most abundant natural fatty acid, is a saturated fatty acid found in palm oil and other fats. The palmitic acid is also one of major fatty acids of skin produced by the sebaceous gland and is used in beauty care and cosmetic products as a moisturizer. It maintains skin in normal and health state by stabilizing oil balance, softens the skin and acts like an anti-keratinizing agent. An ester of palmitic acid is used to provide silkiness to the skin and hair. The palmitic acid acts as a carrier that can deliver a pentapeptide into the skin. It is also used widely as a lubricant, an emulsifier, a surfactant and a formula texturizer.

A fatty acid appropriate for the present disclosure includes lauric acid, stearic acid, palmitic acid, undecylenic acid, palmitoleic acid, oleic acid, linoleic acid, linolenic acid, arachidonic acid and erucic acid, although not being limited thereto. Additional appropriate fatty acids are disclosed in International Cosmetic Ingredient Dictionary and Handbook, 7th Ed. (1997) volume 2, page 1567.

The chemical compound fused with the skin-penetrating peptide may include a vitamin, a derivative thereof and a retinoid, although not being limited thereto. Ascorbic acid (vitamin C), α-tocopherol (vitamin E) and retinoid (vitamin A) may provide favorable characteristics to skin. Ascorbic acid stimulates the synthesis of connective tissues and, in particular, is involved in the stimulation and regulation of collagen production. It helps to prevent or minimize cell damages caused by fat oxidation, continued exposure to UV or other reasons (Varani, J. et al., *J. Invest. Dermatol.* 114: 480-486 (2000); Offord, E. A. et al, *Free Radical Biol. & Med.* 32:1293-1303, (2002)). Ascorbic acid helps to inhibit melanin production and histamine secretion by the cell membrane, compensates for vitamin E deficiency in skin, is involved in preventing decoloration of the skin and has anti-free radical activity. α-Tocopherol is an antioxidant which prevents harmful effects of phospholipids and free radicals of the cell membrane (J. B. Chazan et al. Free Radicals and Vitamin E. *Cah. Nutr. Diet.* 1987, 22(1): 66-76). Retinoids block inflammatory mediators in the skin and increase the production of type 1 and type III collagen by increasing procollagen production.

The term "peptide fusion product (fusion peptide)" used in the present disclosure means a peptide fusion product with a new molecular structure, obtained by binding a rPTP peptide, which is a low-molecular-weight peptide having physiological activity, to the N-terminal or C-terminal of a skin-penetrating peptide or a variant of the skin-penetrating peptide with one or more amino acid changed.

The skin-penetrating peptide may be a skin-penetrating peptide having a sequence of $(X1)_n$-X2-(cysteine)-$(X3)_m$, wherein n is an integer from 3 to 14, specifically an integer from 3 to 6, m is an integer from 4 to 14, specifically an integer from 4 to 7.

The skin-penetrating peptide consists of specifically 9-14, more specifically 9-12, most specifically 9-10, amino acids. When the number of amino acids is smaller than the lower limit, cell permeation efficiency may decrease rapidly. And, if it exceeds the upper limit, the risk of immune response is increased.

In the skin-penetrating peptide, each of X1 and X3 is independently a positively charged amino acid, specifically arginine (Arg, R), lysine (Lys, K) or histidine (His, H), more specifically arginine or lysine. $(X1)_n$ is formed by n positively charged amino acids corresponding to X1. The n amino acids may be the same or different positively charged amino acids. Similarly, $(X3)_m$ is formed by m positively charged amino acids which may be different from each other.

In the skin-penetrating peptide, X2 is a nonpolar or positively charged amino acid, specifically alanine (Ala, A), glycine (Gly, G), proline (Pro, P), tryptophan (Trp, W), phenylalanine (Phe, F), leucine (Leu, L), isoleucine (Ile, I), methionine (Met, M), valine (Val, V), arginine (Arg, R), lysine (Lys, K) or histidine (His, H), more specifically alanine, tryptophan or arginine.

More specifically, the skin-penetrating peptide consists of an amino acid sequence of SEQ ID NO 1, SEQ ID NO 5, SEQ ID NO 8 or SEQ ID NO 12.

The rPTP peptide is a recombinant peptide having biological activity and consisting of the fragments of the PTPN2 protein. It exhibits activity related with physiological phenomena or therapeutic purposes by being delivered into cells through the skin.

Figure 52:
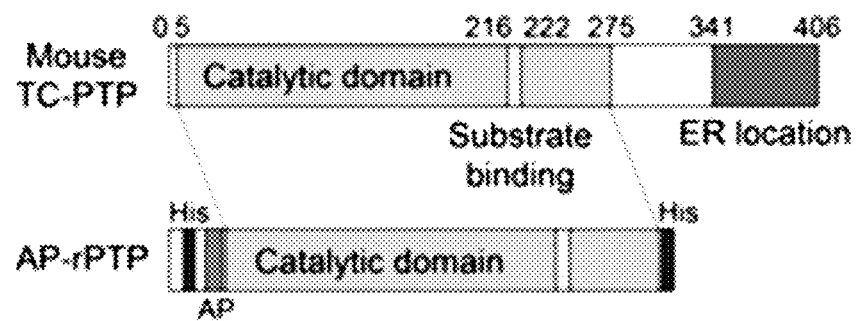
FIG. 52 shows the structure of a fusion product of a recombinant peptide (rPTP) designed from a PTPN2 protein (TC-PTP) and a skin-penetrating peptide (AP).

The PTPN2 protein is T-cell protein tyrosine phosphatase also called TC-PTP. It is an enzyme that can regulate cytokine receptor signals (JAK1, JAK3, STAT1, STAT3, STATS, STATE) associated with the JAK-STAT pathway and inhibits T-cell receptor signaling molecules such as Src family tyrosine kinases (Lck, Fyn). Genes encoding the PTNT2 protein are shown in FIG. 52. Among them, the rPTP peptide is designed by binding a catalytic domain with a substrate-binding domain binding to the AP sequence (FIG. 52, bottom). The rPTP peptide designed as described above is topically applied to skin to improve or treat the symptoms of dermatitis.

Because subtypes derived from the PTPN2 protein other than the above-described amino acid sequence are difficult to be effectively bound to the skin-penetrating peptide, they may exhibit decreased skin permeation efficiency or decreased effect of preventing and treating inflammatory skin diseases.

In addition, the rPTP peptide of an amino acid sequence formed of SEQ ID NO 20 designed according to the present disclosure is advantageous in that it exhibits superior effect of treating or preventing inflammatory skin disease (psoriasis, allergy, chronic dermatitis, etc.).

The fusion between the skin-penetrating peptide and the rPTP peptide is peptide bonding or chemical bonding. The chemical bonding may be selected from a group consisting of disulfide bonding, diamine bonding, sulfide-amine bonding, carboxyl-amine bonding, ester bonding and covalent bonding.

The fusion product according to the present disclosure may have an amino acid sequence of SEQ ID NO 19 and has remarkably superior effect of preventing and treating inflammatory skin diseases as compared to the physiologically active protein alone.

When other existing peptides are used as the skin-penetrating peptide, the effect on inflammatory skin diseases is decreased remarkably. Therefore, it can be seen that the improvement in skin permeation efficiency (particularly, transdermal cell-penetrating efficiency) and effect of treating or preventing inflammatory skin diseases is not due to the inherent property of the skin-penetrating peptide or the rPTP peptide.

As described above, the peptide fusion product according to the present disclosure not only exhibits superior skin permeation efficiency but also is capable of exhibiting superior therapeutic and preventive effects with transdermal administration only. Accordingly, the fusion product according to the present disclosure can be usefully used as a drug which is effective in preventing and treating inflammatory skin diseases.

The fusion product effectively regulates cytokine production in activated T cells and shows inhibitory effect in both preventive and therapeutic models of inflammatory skin diseases (psoriasis, allergy dermatitis, chronic dermatitis).

The skin-penetrating peptide and the rPTP peptide are fused by covalent bonding, including ester, amide, ether and carbamide bonding, although not being limited thereto.

Because the skin-penetrating peptide is a very small peptide, it can minimize biological interference by active substances that may occur. The fusion product of the skin-penetrating peptide and the biologically active substance may be delivered into the body through skin.

Another aspect of the present disclosure relates to a recombinant expression vector containing a gene encoding the fusion product.

The recombinant expression vector may contain the sequence of the skin-penetrating peptide and the rPTP peptide (SEQ ID NO 19) and a tag sequence facilitating the purification of the fusion product, e.g., a continuous histidine codon, a maltose-binding protein codon, a Myc codon, etc., and may further contain a fusion partner for increasing the solubility of the fusion product. For stabilization of the entire structure and function of the recombinant protein or the flexibility of the protein encoded by each gene, it may further contain a spacer amino acid or a base sequence. Examples of the spacer include, but are not limited to, AAY (P. M. Daftarian et al., *J Trans Med* 2007, 5:26), AAA, NKRK (R. P. M. Sutmuller et al., *J Immunol.* 2000, 165: 7308-7315) or one or several lysine residues (S. Ota et al., *Can Res.* 62, 1471-1476; K. S. Kawamura et al., *J Immunol.* 2002, 168: 5709-5715). Also, a marker or reporter gene sequence for identifying the delivery of a sequence specifically cleaved by an enzyme in order to remove undesired portion from the recombinant protein or an expression-regulating sequence into cells may be contained, although not being limited thereto.

The expression-regulating sequence used in the recombinant expression vector may be a regulatory domain including a promoter which is specific for cells, tissues or organs to which or in which the target DNA and/or RNA is selectively delivered or expressed.

In a cosmetic composition of the present disclosure, the biologically active substance fused with the skin-penetrating peptide may be a substance having the activity of antioxidation, increasing vascularization, reducing symptoms of acne, reducing secretion, delaying aging, reducing wrinkles, reducing melanin production, alleviating skin inflammations or improving skin dryness.

In a pharmaceutical composition for external application to skin of the present disclosure, the biologically active substance fused with the skin-penetrating peptide may be a chemical compound acting on the peripheral nerve, adrenaline receptor, choline receptor, skeletal muscles, cardiovascular system, smooth muscles, blood circulatory system, synaptic sites, neuroeffector junctions, endocrine and hormone systems, immune system, reproductive system, skeletal system, autacoid system, digestive and excretory systems, histamine system and central nervous system.

The chemical compound may include a local anesthetic, an antiinflammatory agent, an antiinfective, an antiacne agent, an antiviral agent, an antibacterial agent, an antipsoriasis agent such as topical corticosteroid, etc.

For example, the chemical compound may be selected from 16α,17α-epoxyprogesterone (CAS No. 1097-51-4), p-methoxycinnamic acid/4-methoxycinnamic acid (CAS No. 830-09-1), octyl methoxycinnamate (CAS No. 5466-77-3), octyl methoxycinnamate (CAS No. 5466-77-3), methyl p-methoxycinnamate (CAS No. 832-01-9), 4-estrene-17β-OL-3-one (CAS No. 62-90-8), ethyl p-anisoyl acetate (CAS No. 2881-83-6), dihydrouracil (CAS No. 1904-98-9), lopinavir (CAS No. 192725-17-0), ritanserin (CAS No. 87051-43-2), nilotinib (CAS No. 641571-10-0); rocuronium bromide (CAS No. 119302-91-9), p-nitrobenzyl-6-(1-hydroxyethyl)-1-azabicyclo(3.2.0)heptane-3,7-dione 2-carboxylate (CAS No. 74288-40-7), abamectin (CAS No. 71751-41-2), paliperidone (CAS No. 144598-75-4), gemifloxacin (CAS No. 175463-14-6), valrubicin (CAS No. 56124-62-0), mizoribine (CAS No. 50924-49-7), solifenacin succinate (CAS No. 242478-38-2), lapatinib (CAS No. 231277-92-2), dydrogesterone (CAS No. 152-62-5), 2,2-dichloro-N-[(1R,2S)-3-fluoro-1-hydroxy-1-(4-methylsulfonylphenyl)propan-2-yl]acetamide (CAS No. 73231-34-2), tilmicosin (CAS No. 108050-54-0), efavirenz (CAS No. 154598-52-4), pirarubicin (CAS No. 72496-41-4), nateglinide (CAS No. 105816-04-4), epirubicin (CAS No. 56420-45-2), entecavir (CAS No. 142217-69-4), etoricoxib (CAS No. 202409-33-4), cilnidipine (CAS No. 132203-70-4), doxorubicin hydrochloride (CAS No. 25316-40-9), escitalopram (CAS No. 128196-01-0), sitagliptin phosphate monohydrate (CAS No. 654671-77-9), acitretin (CAS No. 55079-83-9), rizatriptan benzoate (CAS No. 145202-66-0), doripenem (CAS No. 148016-81-3), atracurium besilate (CAS No. 64228-81-5), nilutamide (CAS No. 63612-50-0), 3,4-dihydroxyphenylethanol (CAS No. 10597-60-1), ketanserin tartrate (CAS No. 83846-83-7), ozagrel (CAS No. 82571-53-7), eprosartan mesylate (CAS No. 144143-96-4), ranitidine hydrochloride (CAS No. 66357-35-5), 6,7-dihydro-6-mercapto-5H-pyrazolo[1,2-a][2,4]triazolium chloride (CAS No. 153851-71-9), sulfapyridine (CAS No. 144-83-2), teicoplanin (CAS No. 61036-62-2), tacrolimus (CAS No. 104987-11-3), lumiracoxib (CAS No. 220991-20-8), allyl alcohol (CAS No. 107-18-6), protected meropenem (CAS No. 96036-02-1), nelarabine (CAS No. 121032-29-9), pimecrolimus (CAS No. 137071-32-0), 4-[-methoxy-7-(3-piperidin-1-ylpropoxy)quinazolin-4-yl]-N-(4-propan-2-yloxyphenyl)piperazine-1-carboxamide (CAS No. 387867-13-2), ritonavir (CAS No. 155213-67-5), adapalene (CAS No. 106685-40-9), aprepitant (CAS No. 170729-80-3), eplerenone (CAS No. 107724-20-9), rasagiline mesylate (CAS No. 161735-79-1), miltefosine (CAS No. 58066-85-6), raltegravir potassium (CAS No. 871038-72-1), dasatinib monohydrate (CAS No. 863127-77-9), oxomemazine (CAS No. 3689-50-7), pramipexole (CAS No. 104632-26-0), parecoxib sodium (CAS No. 198470-85-8), tigecycline (CAS No. 220620-09-7), toltrazuril (CAS No. 69004-03-1), vinflunine (CAS No. 162652-95-1), drospirenone (CAS No. 67392-87-4), daptomycin (CAS No. 103060-53-3), montelukast sodium (CAS No. 151767-02-1), brinzolamide (CAS No. 138890-62-7), maraviroc (CAS No. 376348-65-1), doxercalciferol (CAS No. 54573-75-0), oxolinic acid (CAS No. 14698-29-4), daunorubicin hydrochloride (CAS No. 23541-50-6), nizatidine (CAS No. 76963-41-2), idarubicin (CAS No. 58957-92-9), fluoxetine hydrochloride (CAS No. 59333-67-4), ascomycin (CAS No. 11011-38-4), β-methyl vinyl phosphate (MAP) (CAS No. 90776-59-3), amorolfine (CAS No. 67467-83-8), fexofenadine hydrochloride (CAS No. 83799-24-0), ketoconazole (CAS No. 65277-42-1), 9,10-difluoro-2,3-dihydro-3-methyl-7-oxo-7H-pyrido-1 (CAS No. 82419-35-0), ketoconazole (CAS No. 65277-42-1), terbinafine hydrochloride (CAS No. 78628-80-5), amorolfine (CAS No. 78613-35-1), methoxsalen (CAS No. 298-81-7), olopatadine (CAS No. 113806-05-6), zinc pyrithione (CAS No. 13463-41-7), olopatadine hydrochloride (CAS No. 140462-76-6), cyclosporin (CAS No. 59865-13-3), botulinum toxin and analogues and vaccine components thereof.

The skin-penetrating peptide and the biologically active substance are fused by covalent bonding, including ester, amide, ether and carbamide bonding, although not being limited thereto.

Because the skin-penetrating peptide is a very small peptide, it can minimize biological interference by active substances that may occur. The fusion product of the skin-penetrating peptide and the biologically active substance may be delivered into the body through skin.

The cosmetic composition of the present disclosure may contain the fusion product in which the skin-penetrating peptide is fused with the rPTP peptide.

The cosmetic composition of the present disclosure or the pharmaceutical composition for external application to skin contains the fusion product in an amount of 0.0001-50 wt % based on the total weight of the composition. The composition may further contain, in addition to the fusion product, one or more active ingredient exhibiting the same or similar effect.

Because the fusion product penetrates the stratum corneum of skin, the cosmetic composition or the pharmaceutical composition for external application to skin containing the same may be most specifically transdermal. For example, it may be formulated as an ointment or a gel. Due to this special property, it can be directly administered to a disease site. In addition, it can provide preventive and therapeutic effects for skin diseases more advantageously through transdermal administration because it has fewer side effects.

The composition may further contain, in addition to the fusion product described above, a pharmaceutically or physiologically acceptable carrier, excipient or diluent. Examples of the suitable carrier, excipient or diluent that can be contained in the composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinylpyrrolidone, water, methyl hydroxybenzoate, propyl hydroxybenzoate, talc, magnesium stearate, mineral oil, etc. The composition may further contain a commonly used filler, extender, binder, disintegrant, surfactant, anticoagulant, lubricant, wetting agent, fragrance, emulsifier, antiseptic, etc.

The composition may be formulated into a solution, an emulsion (including microemulsion), a suspension, a cream, a lotion, a gel, a powder or a typical solid or liquid composition for application to skin or other tissues. The composition may additionally contain an antimicrobial, a moisturizer, a hydration agent, a penetration agent, a preservative, an emulsifier, a natural oil or synthetic oil, a solvent, a surfactant, a detergent, a gelling agent, an emollient, an antioxidant, a fragrance, a filler, a thickener, a wax, a deodorant, a dye, a colorant, a powder, a viscosity-controlling agent and water, and may optionally contain an anesthetic, an anti-itch agent, a plant extract, a conditioning agent, a darkening or lightening agent, a glitter, a humectant, mica, a mineral, a polyphenol, a silicone or a derivative thereof, a sunblock, a vitamin and a phytomedicine.

The administration dosage of the composition may vary depending on the body weight, age, sex, physical condition and diet of a subject, administration time, administration method, excretion rate, severity of a disease, etc. A daily administration dosage may be about 0.01-100 mg/kg, specifically 0.5-10 mg/kg, and may be administered once or several times a day.

Most specifically, the inflammatory skin disease may be inflammatory dermatitis, psoriasis, wound or atopic dermatitis.

The present disclosure provides a method for preventing or treating an inflammatory skin disease, including a step of applying an effective amount of the pharmaceutical composition for external application to skin to the skin of a subject.

Because the pharmaceutical composition for external application to skin can be injected to the body or cells through the skin, it may be applied to the skin, particularly a disease site, of a human or a non-human animal to effectively prevent or treat the disease.

The present disclosure provides a method for transdermal delivery of a biologically active substance, including: a step of preparing a delivery complex by binding the skin-penetrating peptide to a biologically active substance; and a step of injecting the delivery complex into the body or cells through skin.

The binding between the skin-penetrating peptide and the biologically active substance may be achieved in a nucleotide level via indirect linking by a cloning technique using an expression vector or via direct linking by chemical or physical covalent bonding or noncovalent bonding between the peptide and the biologically active substance.

Most specifically, the biologically active substance may be the rPTP peptide derived from the PTPN2 protein.

The present disclosure provides a method for gene therapy, including: a step of preparing a delivery complex by binding the skin-penetrating peptide to a genetic material; and a step of injecting the delivery complex into skin cells.

The binding between the skin-penetrating peptide and the genetic material may be achieved via direct linking by chemical or physical covalent bonding or noncovalent bonding between the peptide and the genetic material. The delivery complex of the genetic material may be injected into the body or cells via the same route as described above.

Most specifically, the biologically active substance may be the rPTP peptide derived from the PTPN2 protein.

The delivery complex of the genetic material is nonimmunogenic and noninfectious and is not limited by the size of a plasmid because DNA is not packaged in a vector organism such as a retrovirus or an adenovirus. Accordingly, it can be used in recombinant gene-expressing structures of any practical sizes.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

<Preparation of Peptide Derived from Skin-Penetrating Peptide (AP) and PTPN2>

Preparation Example 1: Synthesis and Purification of Peptide

A recombinant peptide (rPTP) having an amino acid sequence of SEQ ID NO 20 was synthesized from a skin-penetrating peptide (AP) having an amino acid sequence selected from SEQ ID NOS 1-12, 15 and 17 and the PTPN2 protein.

After synthesizing sense and antisense oligodeoxynucleotides corresponding to the amino acid sequences, followed by removal of secondary or tertiary structures (denaturation) at 95° C. for 3 minutes, double-stranded DNAs were prepared by changing temperature to 50° C. and then to 72° C. For insertion into a pRSET-b vector, restriction enzyme-specific sequences were inserted into 5' and 3' sites in addition to the sense and antisense oligodeoxynucleotides. Then, the sequences were amplified in large quantities by transforming into E. coli. After confirming the integrity of the sequences, expression was induced in E. coli.

In order to fuse the peptide having an amino acid sequence selected from SEQ ID NOS 1-12, 15 and 17 (hereinafter also referred to as 'AP') with recombinant peptide designed from the PTPN2 protein (hereinafter also referred to as 'rPTP') (SEQ ID NO 20) or a green fluorescent protein (EGFP), a primer was constructed which allows linking of EGFP at the N-terminal of AP. After producing an AP-rPTP or AP-EGFP gene through PCR, it was inserted into a vector (pRSET-b). The protein was expressed in E. coli and then purified to measure intracellular delivery effect.

<Preparation of AP-EGFP Protein and Recombinant Expression Vector>

Preparation Example 2: Preparation of Double-Stranded DNA Encoding AP Having EGFP Linked at N-Terminal A forward primer was constructed by adding a DNA base sequence which encodes the peptide having an amino acid sequence of SEQ ID NO 1 to a DNA base sequence which encodes a part of the N-terminal of green fluorescent protein (hereinafter also referred to as 'EGFP').

A forward primer of SEQ ID NO 13 contained a NheI restriction enzyme recognition site for DNA cloning at the 5' end and a BamHI restriction enzyme recognition site between the base sequences of AP and EGFP. Meanwhile, a reverse primer of SEQ ID NO 14 was constructed for amplification of AP-EGFP by PCR. The reverse primer contained a DNA base sequence which encodes a part of the C-terminal of EGFP. For DNA cloning, a HindIII restriction enzyme recognition site was inserted at the 5' end of the primer.

PCR was conducted using the pRSETb vector containing the EGFP gene as a template and using the primers of SEQ ID NO 13 and SEQ ID NO 14. After initial thermal denaturation at 95° C. for 3 minutes, PCR was carried out using a PCR machine (Bio-Rad) for 30 cycles (thermal denaturation of the template at 95° C. for 20 seconds→polymerization between the primers and the template at 50° C. for 20 seconds→extension at 72° C. for 30 seconds).

The obtained amplification product AP-EGFP was subjected to 1% agarose gel electrophoresis. It was confirmed that a 789-bp DNA fragment was amplified (FIG. 1).

Preparation Example 3: Preparation of pRSETb Vector Having AP-EGFP Inserted

In order to express the AP-EGFP protein, the 789-bp DNA fragment prepared in Preparation Example 2 was inserted into the protein expression vector pRSETb using a restriction enzyme and a ligase.

The DNA fragment amplified in Preparation Example 2 was treated with NheI and HindIII (NEB) enzymes to make the 5'/3' ends of the DNA sticky. Meanwhile, pRSETb was treated with the same restriction enzymes to prepare a linear pRSETb vector having NheI and HindIII insertion sites. After each enzymatic reaction, the product was separated using a PCR purification kit (Cosmo Genetech).

Figure 2:
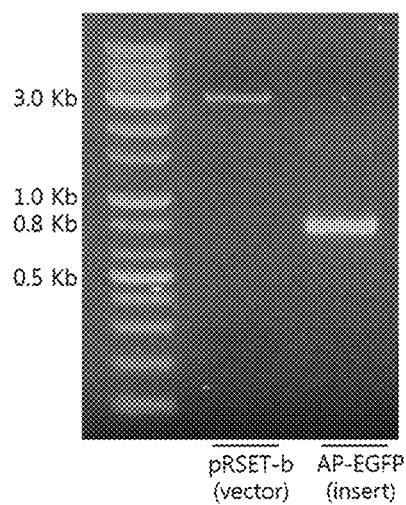
FIG. 2 shows a result of treating an AP-EGFP DNA fragment (789 bp) and a pRSET-b vector (2.9 Kb) of Preparation Example 3 with NheI and HindIII restriction enzymes for insertion of the AP-EGFP DNA fragment and quantifying the amount of DNA by 1% agarose gel electrophoresis.

The separated AP-EGFP double-stranded DNA fragment and pRSET-b vector were treated with T4 ligase (NEB) at 25° C. for 2 hours. The concentrations of the AP-EGFP double-stranded DNA fragment and the pRSET-b vector were analyzed by 1% agarose gel electrophoresis (FIG. 2).

Figure 3:
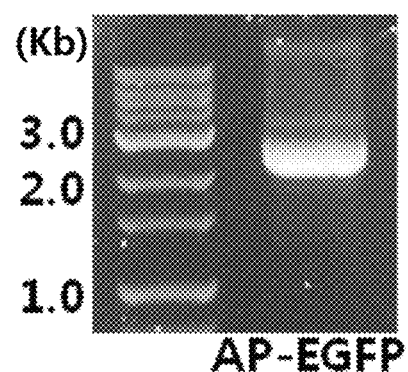
FIG. 3 shows a result of transforming DH5α *E. coli* with a pRSET-b vector in which a DNA fragment encoding AP-EGFP is inserted of Preparation Example 3, culturing a colony selected from culturing on a plate LB medium in a liquid LB medium, isolating DNA through plasmid minipreparation and conducting 1% agarose gel electrophoresis.

The resulting circular pRSETb vector in which AP-EGFP was inserted was transformed into DH5α E. coli and the transformed E. coli, which formed a colony when cultured on a plate LB medium containing 50 μg/mL ampicillin as an antibiotic, was selected. The selected E. coli colony was cultured again in a liquid LB medium containing 50 μg/mL ampicillin and then the plasmid vector was separated using a plasmid minipreparation kit (Cosmo Genetech) (FIG. 3).

Figure 4:
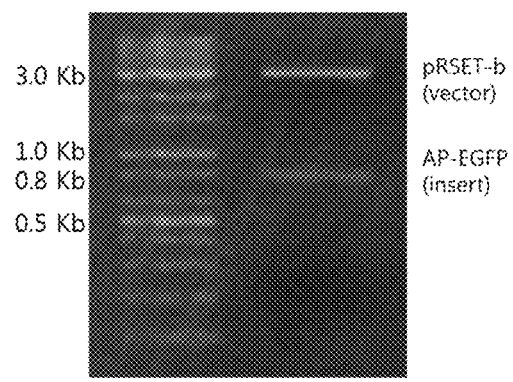
FIG. 4 shows a result confirming that a plasmid DNA isolated in Preparation Example 3 consists of a DNA fragment encoding AP-EGFP (789 bp) and a pRSET-b vector (2.9 Kb) by treating with NheI and HindIII restriction enzymes and conducting 1% agarose gel electrophoresis.
Figure 5:
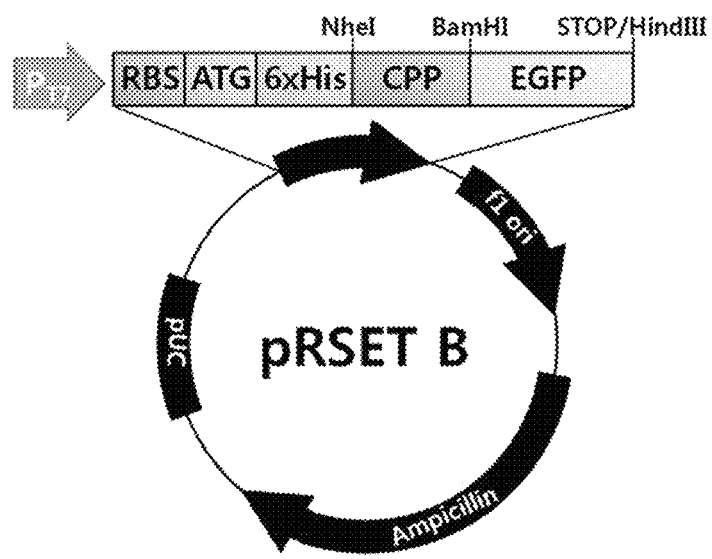
FIG. 5 is a schematic of a pRSET-b vector in which AP-EGFP is inserted of Preparation Example 3.

In order to confirm that the separated plasmid vector is a pRSETb vector in which AP-EGFP is inserted, it was treated with NheI and HindIII restriction enzymes and then analyzed by 1% agarose gel electrophoresis. As a result, it was confirmed that the 789-bp AP-EGFP DNA fragment was inserted in the 2.9-kbp pRSET-b vector (FIG. 4). This could be finally confirmed by DNA base sequence analysis (Bionics). The structure of the pRSETb vector in which AP-EGFP is inserted is shown in FIG. 5.

Preparation Example 4: Expression of AP-EGFP Protein in *E. coli* and Purification The pRSETb vector in which AP-EGFP was inserted of Preparation Example 3 was transformed into *E. coli* BL21 (DE3) star pLysS. A colony formed on a plate LB medium containing 34 µg/mL chloramphenicol and 50 µg/mL ampicillin as antibiotics was cultured in 50 mL of a liquid LB medium at 37° C. for 10 hours and then transferred to 500 mL of a fresh liquid LB medium. After culturing at the same temperature until the quantity of *E. coli* measured by a spectrophotometer reached O.D. 0.5, IPTG (isopropyl β-D-1-thiogalactopyranoside) was added to a concentration of 1 mM and the *E. coli* was further cultured in a shaking incubator set to 20° C. and 150 rpm for 14 hours. The protein expressed by the *E. coli* contained a 6x-His tag upstream of AP-EGFP of the pRSET-b vector. The protein was purified as follows.

Figure 6:
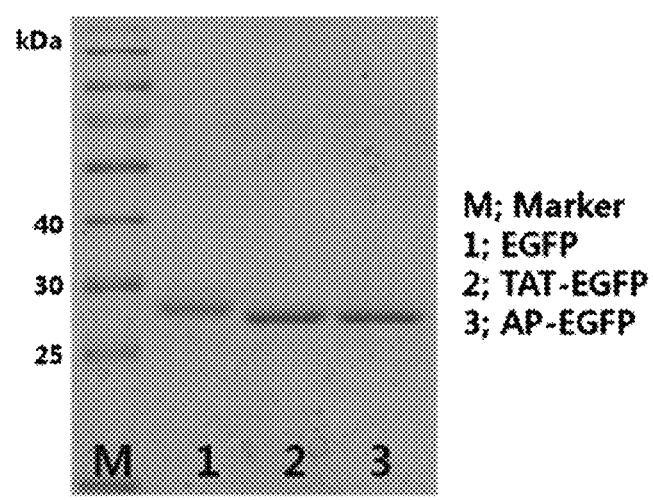
FIG. 6 shows a result of 12% SDS gel electrophoresis of a purified AP-EGFP protein of Preparation Example 4, an EGFP protein in which a cell-penetrating peptide is not linked as a negative control group and a TAT-EGFP protein, which is the most widely known cell-penetrating peptide, as a positive control group.

The culture was centrifuged and then resuspended in a lysis buffer (0.5 M NaCl, 5 mM imidazole, 20 mM Tris-HCl, pH 8.0) under a native condition. Then, the cells were disrupted using the ultrasonic cell crusher VCX-130 (Sonics & Materials) and then centrifuged. The separated supernatant was filtered once through a 0.45-µm filter (Advantec) and was allowed to bind to Ni-NTA agarose (Qiagen) at room temperature for 1 hour. Then, only the protein product binding to the Ni-NTA agarose was made to bind to a histidine column (His-column, Bio-Rad). After washing with a 20 mM imidazole solution, the protein was eluted using a 250 mM imidazole solution. Finally, AP-EGFP was purified from the eluted protein product using a PD-10 desalination column (Amersham Biosciences) (FIG. 6).

<Preparation of AP-rPTP Protein and Recombinant Expression Vector>

Preparation Example 5: Preparation of Double-Stranded DNA Encoding rPTP Having AP Linked at N-Terminal A forward primer was constructed by adding a DNA base sequence which encodes the skin-penetrating peptide having an amino acid sequence of SEQ ID NO 1 to a DNA base sequence which encodes a part of the N-terminal SEQ ID NO 20 derived from rPTP.

A forward primer of SEQ ID NO 21 contained a NheI restriction enzyme recognition site for DNA cloning at the 5' end and BamHI and EcoRI restriction enzyme recognition sites between the base sequences of AP and rPTP. Meanwhile, a reverse primer of SEQ ID NO 22 was constructed for amplification of AP-rPTP by PCR. The reverse primer contained a DNA base sequence which encodes a part of the C-terminal of rPTP. For DNA cloning, an XhoI restriction enzyme recognition site was inserted at the 5' end of the primer.

PCR was conducted using the PET28a vector containing the rPTP gene as a template and using the primers of SEQ ID NO 21 and SEQ ID NO 22. After initial thermal denaturation at 95° C. for 3 minutes, PCR was carried out using a PCR machine (Bio-Rad) for 30 cycles (thermal denaturation of the template at 95° C. for 20 seconds→polymerization between the primers and the template at 50° C. for 20 seconds→extension at 72° C. for 30 seconds).

The obtained amplification product AP-rPTP was subjected to 1% agarose gel electrophoresis. It was confirmed that a 945-bp DNA fragment was amplified.

Preparation Example 6: Preparation of PET28a Vector Having AP-rPTP Inserted

In order to express the AP-rPTP protein, the 945-bp DNA fragment prepared in Preparation Example 5 was inserted into the protein expression vector PET28a using a restriction enzyme and a ligase.

The DNA fragment amplified in Preparation Example 5 was treated with NheI and XhoI (NEB) enzymes to make the 5'/3' ends of the DNA sticky. Meanwhile, PET28a was treated with the same restriction enzymes to prepare a linear PET28a vector having NheI and XhoI insertion sites. After each enzymatic reaction, the product was separated using a PCR purification kit (Cosmo Genetech).

The separated AP-rPTP double-stranded DNA fragment and PET28a vector were treated with T4 ligase (NEB) at 25° C. for 2 hours. The concentrations of the AP-rPTP double-stranded DNA fragment and the PET28a vector were analyzed by 1% agarose gel electrophoresis.

The resulting circular PET28a vector in which AP-rPTP was inserted was transformed into DH5α *E. coli* and the transformed *E. coli*, which formed a colony when cultured on a plate LB medium containing 50 µg/mL kanamycin as an antibiotic, was selected. The selected *E. coli* colony was cultured again in a liquid LB medium containing 50 µg/mL kanamycin and then the plasmid vector was separated using a plasmid minipreparation kit (Cosmo Genetech) (FIG. 3).

In order to confirm that the separated plasmid vector is a PET28a vector in which AP-rPTP is inserted, it was treated with NheI and XhoI restriction enzymes and then analyzed by 1% agarose gel electrophoresis. As a result, it was confirmed that the 945-bp AP-rPTP DNA fragment was inserted in the 2.9-kbp PET28a vector. This could be finally confirmed by DNA base sequence analysis (Bionics).

Preparation Example 7: Expression of AP-rPTP Protein in *E. coli* and Purification The PET28a vector in which AP-rPTP was inserted of Preparation Example 6 was transformed into *E. coli* Rosetta. A colony formed on a plate LB medium containing 34 µg/mL chloramphenicol and 50 µg/mL kanamycin as antibiotics was cultured in 50 mL of a liquid LB medium at 37° C. for 10 hours and then transferred to 500 mL of a fresh liquid LB medium. After culturing at the same temperature until the quantity of *E. coli* measured by a spectrophotometer reached O.D. 0.5, IPTG (isopropyl β-D-1-thiogalactopyranoside) was added to a concentration of 0.2 mM and the *E. coli* was further cultured in a shaking incubator set to 20° C. and 150 rpm for 14 hours. The protein expressed by the *E. coli* contained a 6x-His tag upstream of AP-rPTP of the PET28a vector. The protein was purified as follows.

The culture was centrifuged and then resuspended in a lysis buffer (0.3 M NaCl, 10 mM imidazole, 50 mM NaH$_2$PO$_4$, pH 8.0) under a native condition. Then, the cells were disrupted using the ultrasonic cell crusher VCX-130 (Sonics & Materials) and then centrifuged. The separated supernatant was filtered once through a 0.45-µm filter (Advantec) and was allowed to bind to Ni-NTA agarose (Qiagen) at room temperature for 1 hour. Then, only the protein product binding to the Ni-NTA agarose was made to bind to a histidine column (His-column, Bio-Rad). After washing with a 20 mM imidazole solution, the protein was eluted using a 250 mM imidazole solution. Finally, AP-rPTP was purified from the eluted protein product using a PD-10 desalination column (Amersham Biosciences) (FIG. 5I).

Test Example 1: Comparison of Delivery Efficiency of AP-EGFP Protein into Jurkat Cells which are Immortalized Human T Cells The AP-EGFP protein purified in Preparation Example 4 was delivered into Jurkat cells which are immortalized human T cells and the efficiency was investigated. Jurkat cells were cultured using an RPMI medium (HyClone) and then transferred to a 24-well plate (SPL Life Sciences) containing 350 μL of an RPMI medium, with $1 \times 10^6$ cells per well in 100 μL of an RPMI medium. Then, after mixing the protein with 50 μL of D-PBS (Welgene) to a total volume of 500μ, the cells were treated with the protein under various conditions as follows. Unless specified otherwise hereinafter, the cells were treated with each protein at 5 μM and then cultured in a 5% $CO_2$ incubator at 37° C. for 1 hour.

First, after treating with the AP-EGFP protein at a concentration of 1 μM or 5 μM, the cells were cultured in a 5% $CO_2$ incubator at 37° C. for 1 hour. As control groups, the EGFP protein not linked to AP and the TAT-EGFP protein as one of existing cell-penetrating peptides were used. After 1 hour, all the cells were recovered and transferred to a tube. After performing centrifugation, the supernatant was removed. A procedure of washing the cells with 1 mL of D-PBS, resuspending and then centrifuging was repeated 2 times. After the washing, the obtained cells were resuspended finally in 500 μL of D-PBS and the delivery efficiency of the protein into the cells was measured by measuring intracellular fluorescence by flow cytometry using a FACS machine (FACSCanto II, BD Science). As a result, it was confirmed that the AP-EGFP protein was delivered into the Jurkat cells in a concentration-dependent manner.

Figure 7:
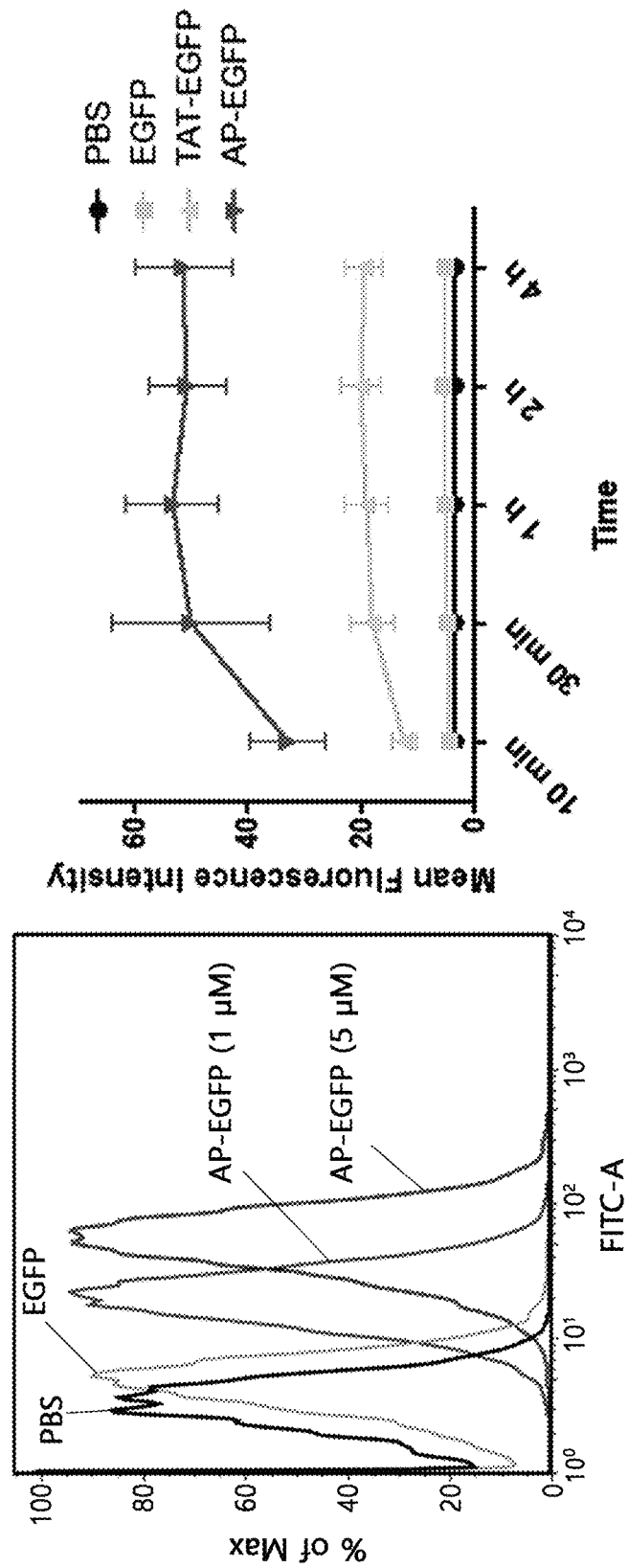
FIG. 7 shows a result of intracellular fluorescence intensity analysis by flow cytometry in Test Example 1 showing that an AP-EGFP protein is delivered into Jurkat cells in a concentration-dependent and time-dependent manner.

Then, after treating with the AP-EGFP protein at a concentration of 5 μM, the cells were cultured in a 5% $CO_2$ incubator at 37° C. for 30 minutes to 4 hours. After washing the cells as described above, intracellular fluorescence was measured by flow cytometry. As a result, it was confirmed that the AP-EGFP protein was delivered into the Jurkat cells in a time-dependent manner (FIG. 7).

Test Example 2: Comparison of Protein Delivery Efficiency into Jurkat Cells with Existing Cell-Penetrating Peptides For comparison of the delivery efficiency with existing cell-penetrating peptides, each protein was delivered into Jurkat cells in the same manner as described in Test Example 1 at the same concentration and for the same time.

Figure 8:
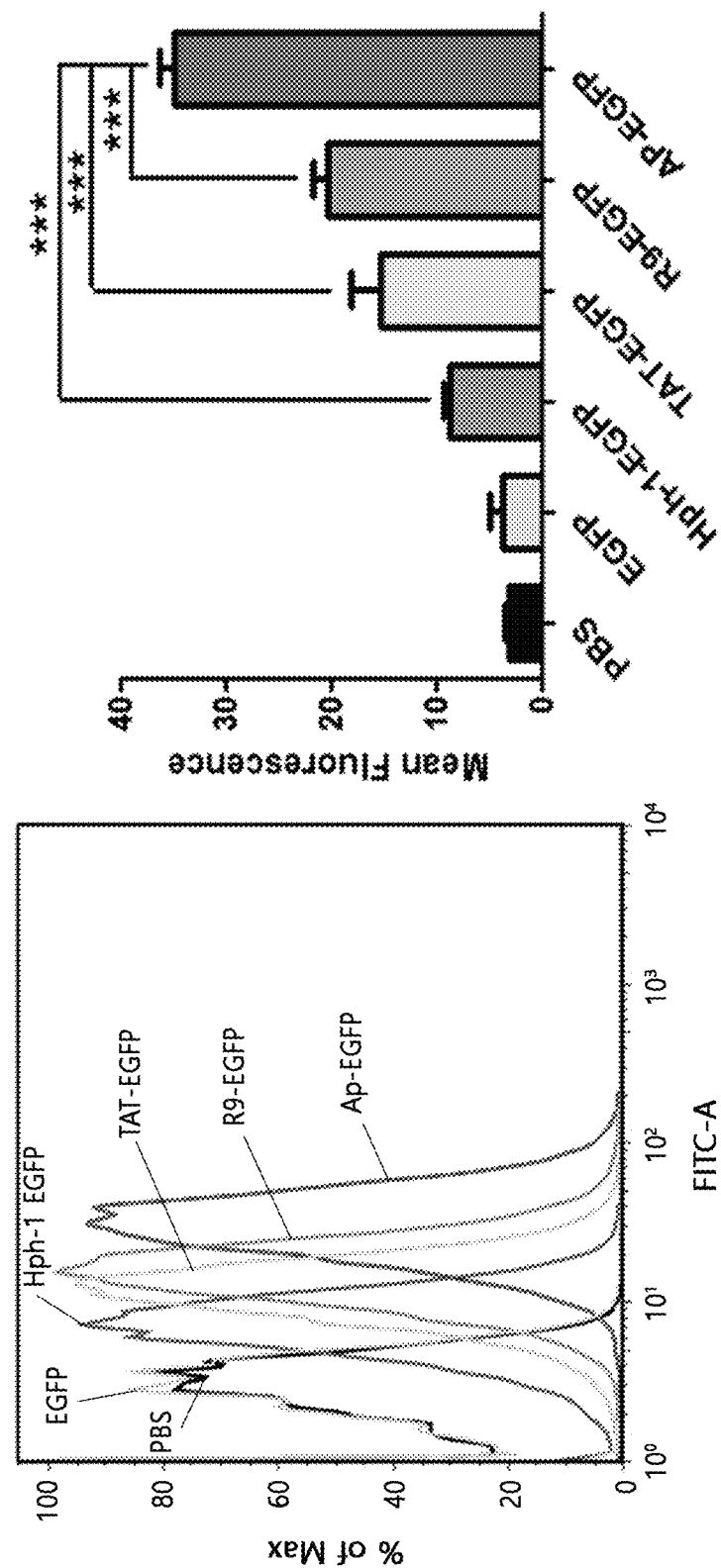
FIG. 8 shows a result of intracellular fluorescence intensity analysis by flow cytometry in Test Example 2 comparing the efficiency of delivery of a protein by AP into Jurkat cells with that of existing cell-penetrating peptides as positive control groups.

The EGFP protein not linked with a cell-penetrating peptide was used as a negative control group and TAT-EGFP, R9-EGFP and Hph-1 EGFP in which EGFP (enhanced green fluorescent protein) is linked with each cell-penetrating peptide were used as positive control groups. As a result, it was confirmed that the AP sequence of the present disclosure delivers the protein into Jurkat cells with higher efficiency than TAT (FIG. 8).

Test Example 3: Comparison of Protein Delivery Efficiency into Jurkat Cells with Existing Skin-Penetrating Peptides For comparison of the delivery efficiency with existing skin-penetrating peptides, each protein was delivered into Jurkat cells in the same manner as described in Test Example 1 at the same concentration and for the same time.

The dTomato fluorescent protein not linked with a skin-penetrating peptide was used as a negative control group and TDP1-dTomato and TDP2-dTomato in which the dTomato fluorescent protein is linked with the skin-penetrating peptide were used as positive control groups.

TDP1-dTomato is a fusion product having an amino acid sequence of SEQ ID NO 16, obtained by linking a linker that can be recognized by a restriction enzyme (amino acid sequence 'GS') at the C-terminal of the skin-penetrating peptide disclosed in Korean Patent Publication No. 10-2013-0135207 (amino acid sequence 'NGSLNTHLAPIL', hereinafter referred to as a 'peptide having an amino acid sequence of SEQ ID NO 15' or 'TDP1') and then linking the dTomato fluorescent protein at the C-terminal of the linker.

TDP2-dTomato is a fusion product having an amino acid sequence of SEQ ID NO 18, obtained by linking a linker that can be recognized by a restriction enzyme (amino acid sequence 'GS') at the C-terminal of the skin-penetrating peptide disclosed in Korean Patent Publication No. 10-2013-0070607 (amino acid sequence 'MRAAAPAVAA', hereinafter referred to as a 'peptide having an amino acid sequence of SEQ ID NO 17' or 'TDP2') and then linking the dTomato fluorescent protein at the C-terminal of the linker.

Figure 9:
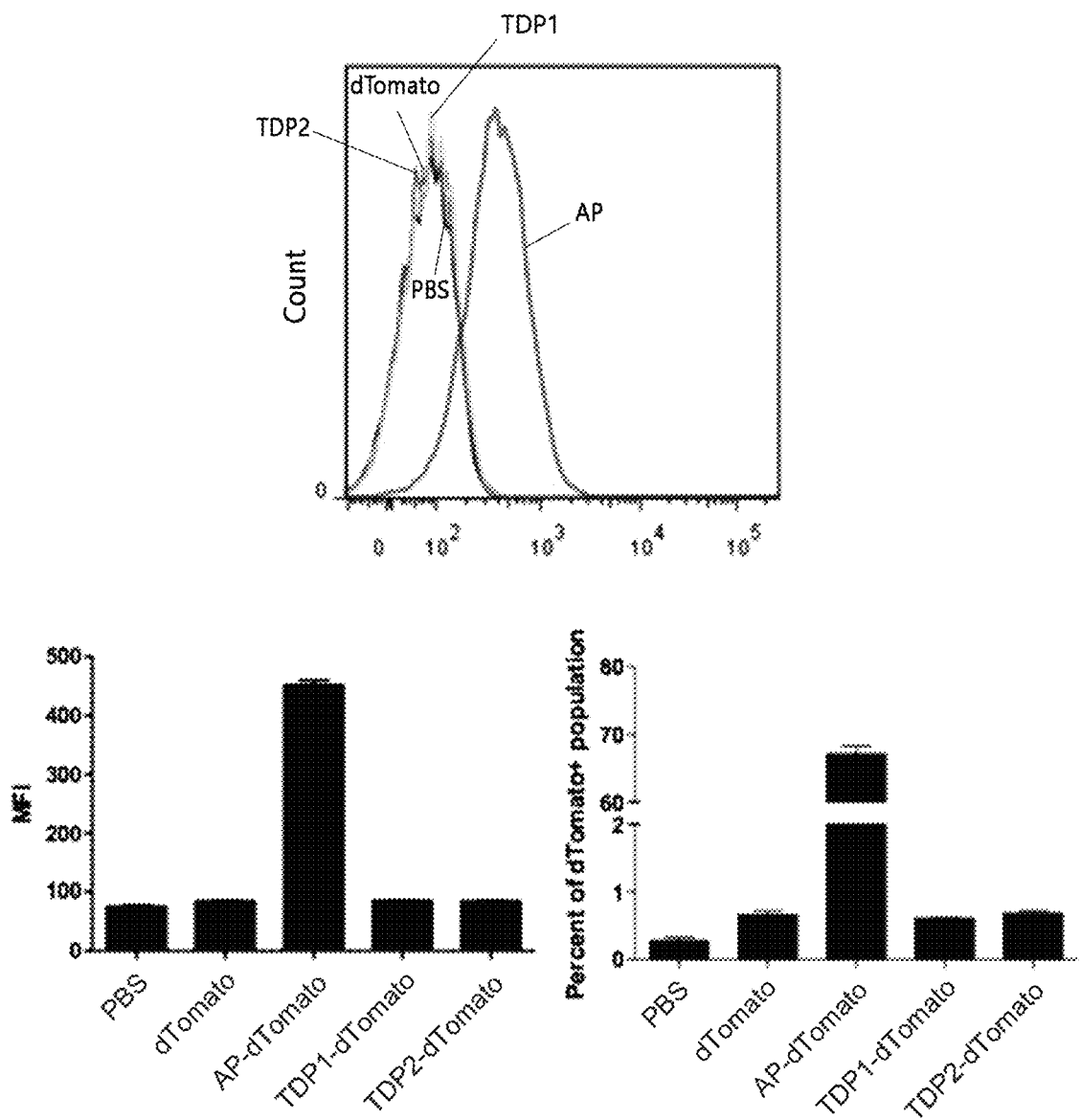
FIG. 9 shows a result of intracellular fluorescence intensity analysis by flow cytometry in Test Example 3 comparing the efficiency of delivery of a protein by AP into Jurkat cells with that of existing cell-penetrating peptides as positive control groups.

As the fusion product in which AP is linked with EGFP was delivered effectively into Jurkat cells in Test Example 2, the fusion product in which AP is linked with dTomato also showed remarkably improved delivery efficiency as compared to the negative control group (dTomato alone). It was also confirmed that the existing skin-penetrating peptide TDP1 or TDP2 exhibits very low delivery efficiency as compared to AP-dTomato when they are linked with the fluorescent protein dTomato having a large molecular weight (FIG. 9).

Test Example 4: Comparison of Protein Delivery Efficiency into Skin Cells with Existing Cell-Penetrating Peptides HaCaT cells are human epidermal cells used in research of in-vitro delivery efficiency and mechanism related with transdermal delivery and skin diseases [*J Invest Dermatol.* 2011 July 131(7): 1477-85; *Biochem Pharmacol.* 2008 Mar. 15; 75(6): 1348-57]. And, NIH3T3 cells are mouse dermal cells which are frequently used in in-vitro experiments for the study of transdermal delivery and skin disease mechanism like HaCaT cells [*J Pharm Sci.* 2013 November 102(11): 4109-20; *J Immunol.* 2003 Jan. 1. 170(1): 548-55.].

Figure 10:
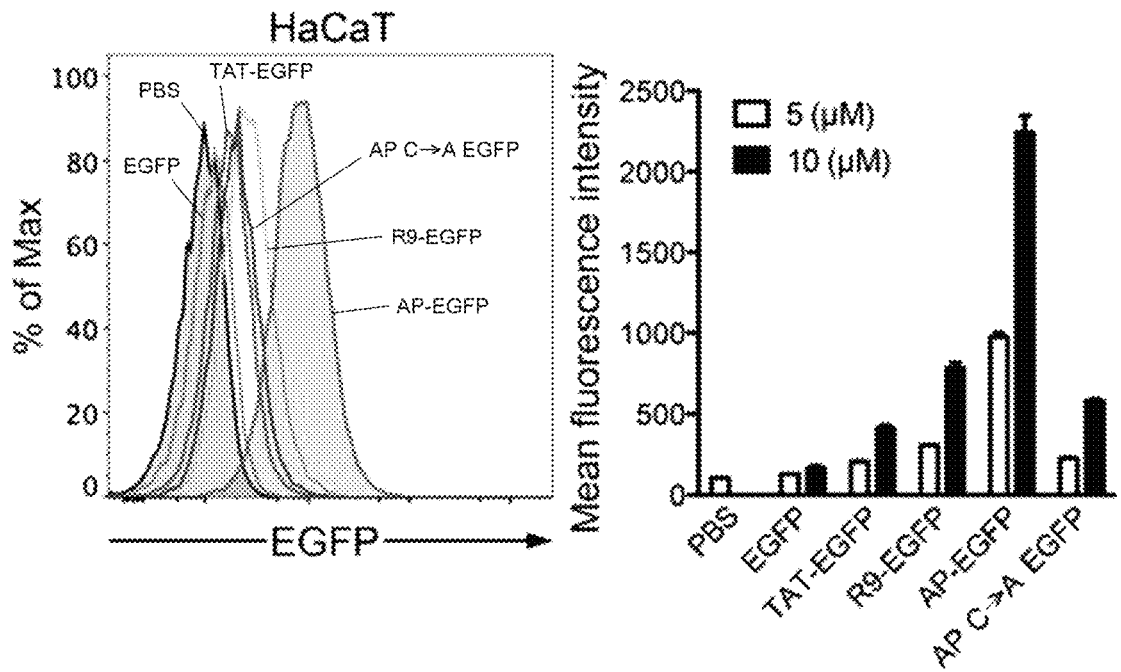
FIG. 10 shows a result of intracellular fluorescence intensity analysis by flow cytometry in Test Example 4 comparing the efficiency of delivery of a protein by AP into skin epidermal HaCaT cells with that of existing cell-penetrating peptides as positive control groups.
Figure 11:
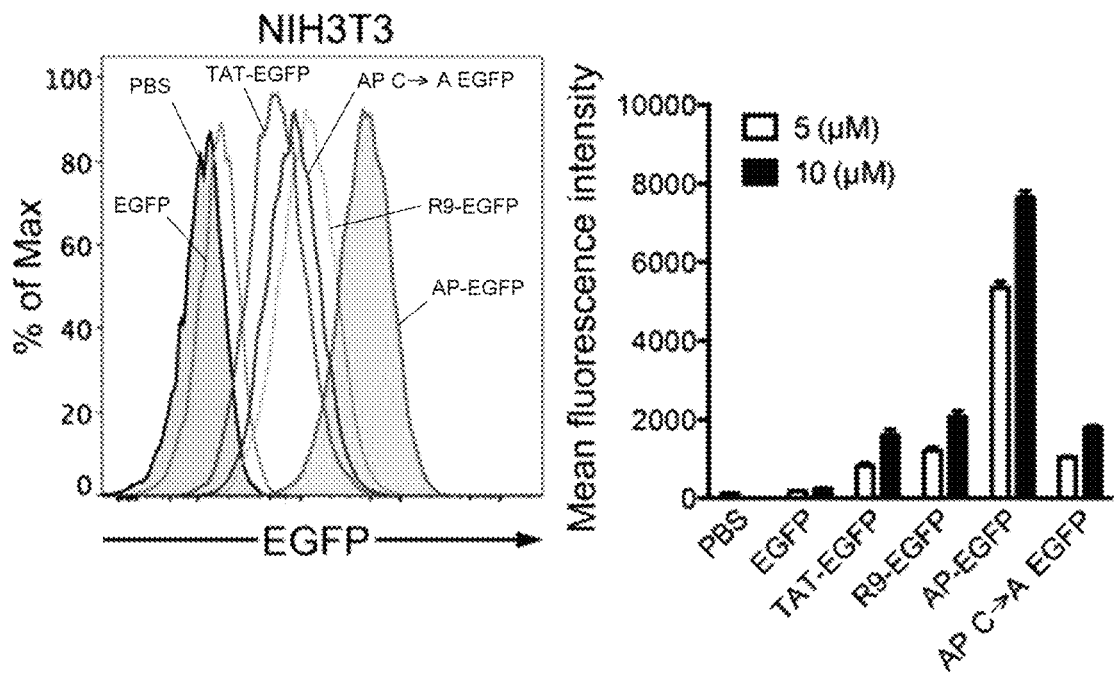
FIG. 11 shows a result of intracellular fluorescence intensity analysis by flow cytometry in Test Example 4 comparing the efficiency of delivery of a protein by AP into skin dermal NIH3T3 cells with that of existing cell-penetrating peptides as positive control groups.

The delivery efficiency of the EGFP fluorescent protein into skin cells by AP was compared with that of existing cell-penetrating peptides using HaCaT cells and NIH3T3 cells. The result is shown in FIG. 10 and FIG. 11.

As in Test Example 2, the EGFP protein not linked with a cell-penetrating peptide was used as a negative control group and TAT-EGFP and R9-EGFP in which EGFP is linked with each cell-penetrating peptide were used as positive control groups. In addition, AP C→A EGFP in which the cysteine of the AP sequence was replaced with alanine was used as another test group.

It was confirmed that AP effectively delivers the protein with a large molecular weight not only into immune cells (Jurkat cells) but also into HaCaT cells and NIH3T3 cells as compared to TAT or R9. The delivery efficiency of AP was significantly decreased when the cysteine contained in the amino acid sequence was replaced with alanine.

Figure 12:
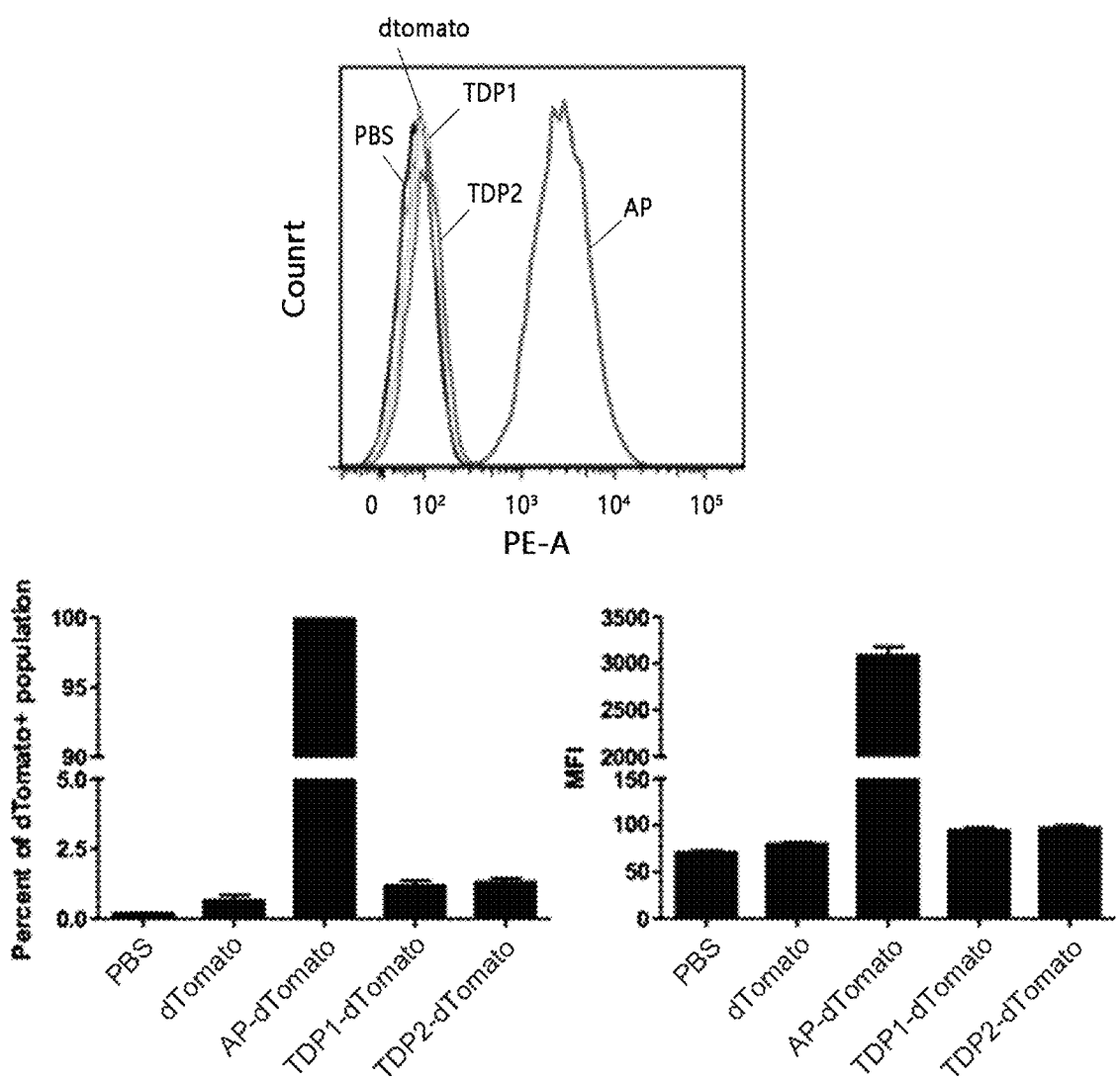
FIG. 12 shows a result of result of intracellular fluorescence intensity analysis by flow cytometry in Test Example 5 comparing the efficiency of delivery of a protein by AP into skin epidermal HaCaT cells with that of existing cell-penetrating peptides as positive control groups.
Figure 13:
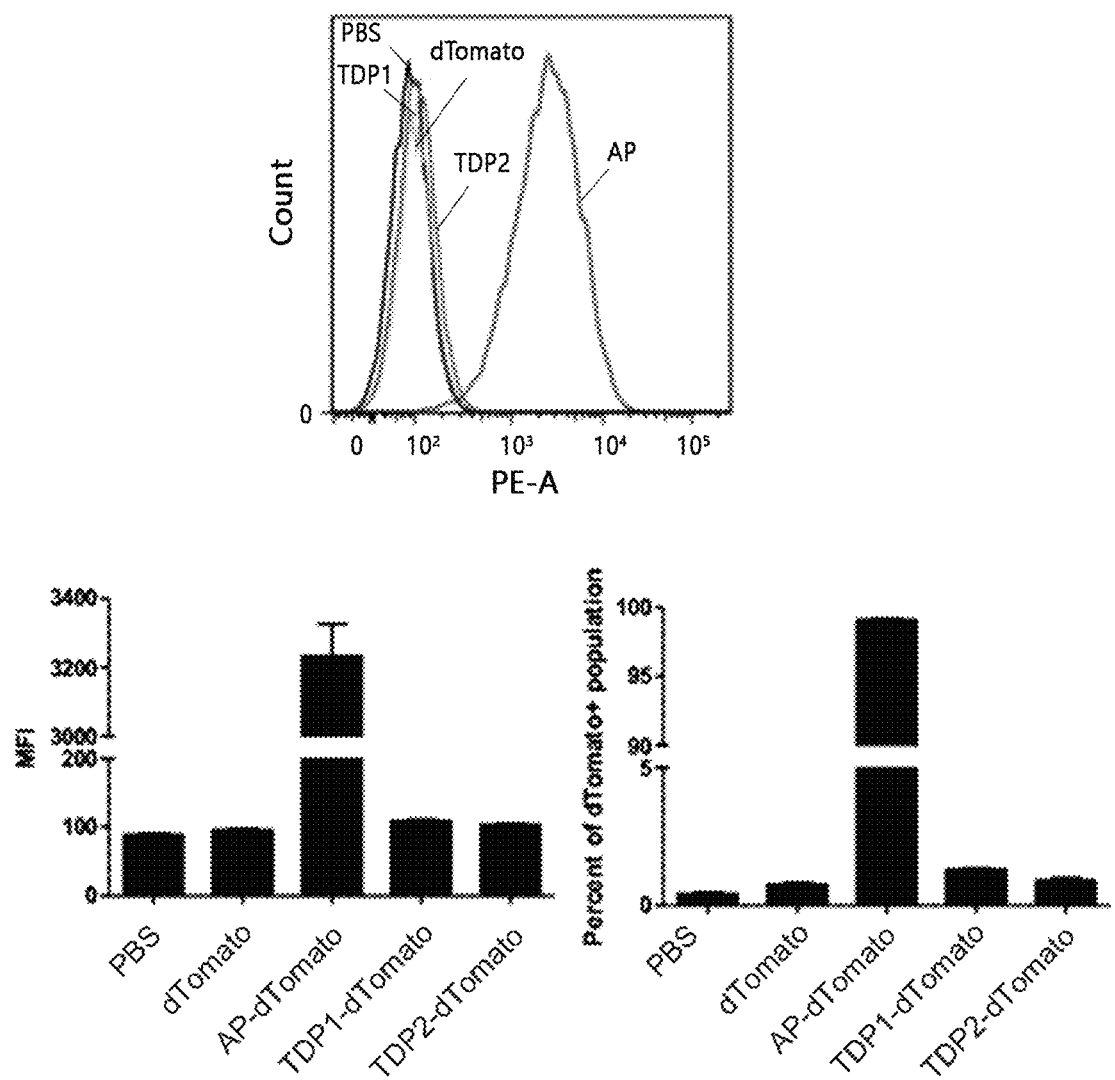
FIG. 13 shows a result of intracellular fluorescence intensity analysis by flow cytometry in Test Example 5 comparing the efficiency of delivery of a protein by AP into skin dermal NIH3T3 cells with that of existing cell-penetrating peptides as positive control groups.

Test Example 5: Comparison of Protein Delivery Efficiency into Skin Cells with Existing Skin-Penetrating Peptides The delivery efficiency of the dTomato fluorescent protein into skin cells by AP was compared with that of existing skin-penetrating peptides using HaCaT cells and NIH3T3 cells. The result is shown in FIG. 12 and FIG. 13.

As in Test Example 3, the dTomato protein not linked with a skin-penetrating peptide was used as a negative control group and TDP1-dTomato and TDP2-dTomato in which the dTomato fluorescent protein is linked with each skin-penetrating peptide were used as positive control groups.

It was confirmed that AP effectively delivers the protein with a large molecular weight not only into immune cells (Jurkat cells) but also into HaCaT cells and NIH3T3 cells, whereas the existing skin-penetrating peptides TDP1 and TDP2 show insignificant effect of improving permeation efficiency when linked with the protein with a large molecular weight.

Test Example 6: Comparison of Protein Delivery Efficiency Depending on Substitution, Removal or Addition of Amino Acid Constituting AP In order to investigate the role of each amino acid constituting AP, various variants were prepared and analyzed for comparison.

(1) Comparison of Protein Delivery Efficiency Depending on Removal of Terminal Amino Acid First, variants with one arginine removed from the N-terminal of AP (AP_D1, SEQ ID NO 2), with one arginine removed from the C-terminal (AP_D2, SEQ ID NO 3) and with one arginine removed from each of the N- and C-terminals (AP_D3, SEQ ID NO 4) were prepared and they were compared with EGFP, AP-EGFP, TAT-EGFP and R9-EGFP as control groups.

Figure 14:
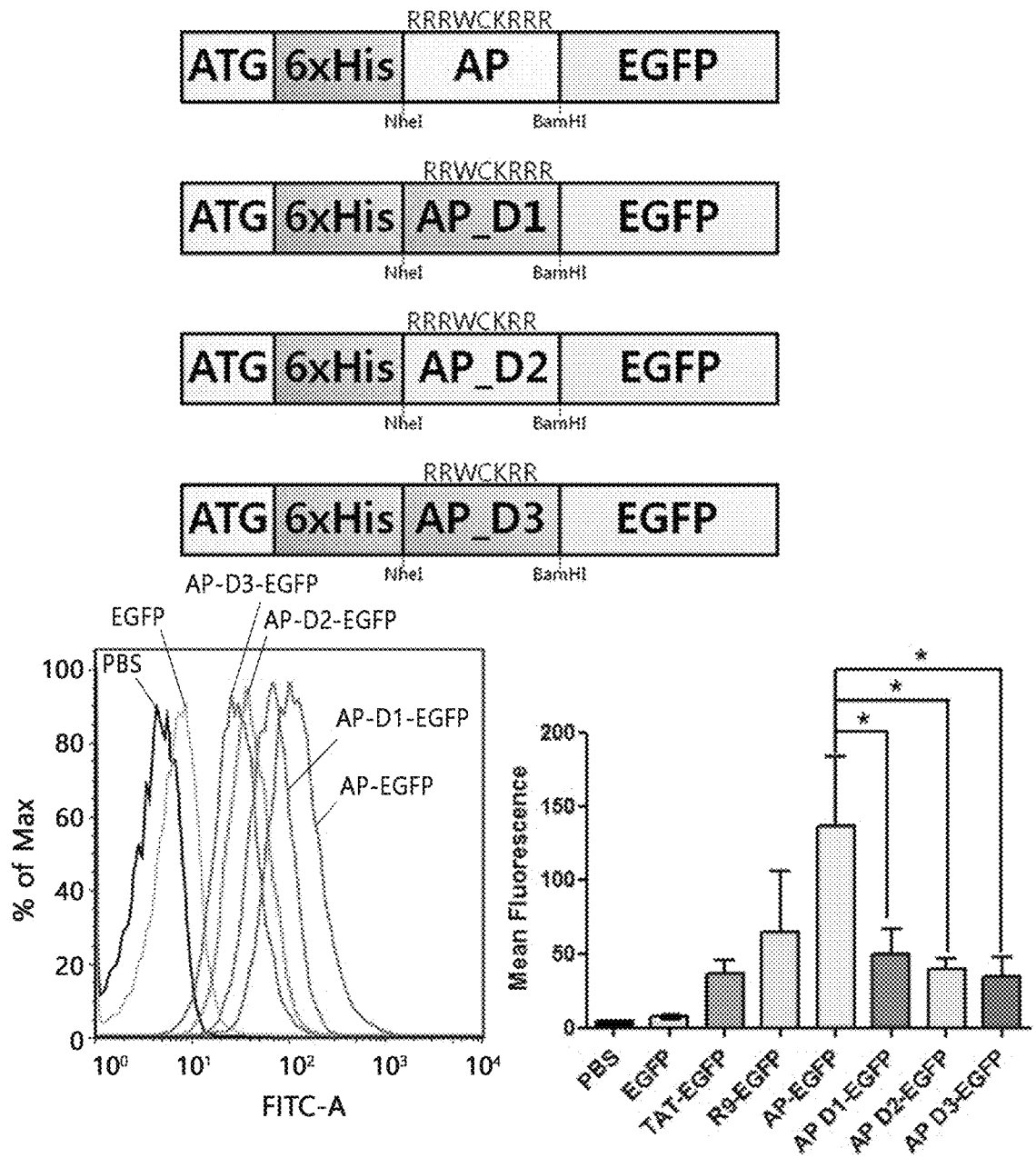
FIG. 14 shows a result of intracellular fluorescence intensity analysis by flow cytometry in Test Example 6 comparing the effect of arginine which occupies the largest portion of AP on delivery of a protein into cells with that of those having less arginines as control groups.

As a result, it was found out that, when one arginine is missing, i.e. when the number of X1 is smaller than 3 or when the number of X2 is smaller than 4, the delivery efficiency decreases significantly as compared to AP. Accordingly, the critical meaning of the lower limit of the number of amino acids X1 and X2 in the delivery of the protein into cells by AP was confirmed (FIG. 14).

(2) Comparison of Protein Delivery Efficiency Depending on Substation of X2, Cysteine or X3

In order to investigate the role of tryptophan (X2), cysteine and lysine (first amino acid of X3), variants were prepared by substituting each amino acid with alanine or arginine. Alanine is suitable as a control group because it has no charge, is the simplest and has a small size.

Figure 15:
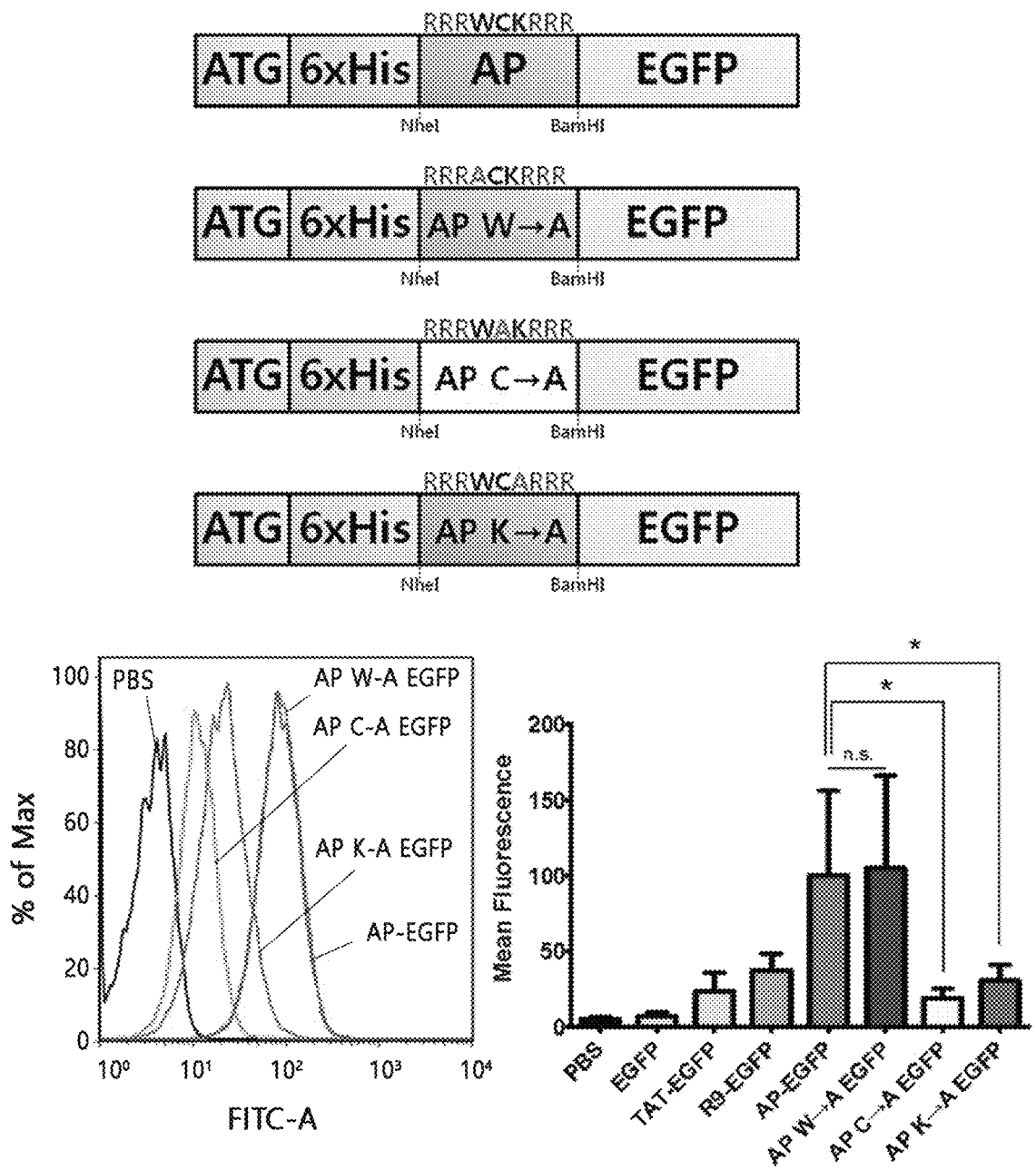
FIG. 15 shows a result of intracellular fluorescence intensity analysis by flow cytometry in Test Example 6 comparing the effect of tryptophan (X2), cysteine and lysine (First amino acid of X3) constituting AP on delivery of a protein into cells by replacing each of them with alanine.
Figure 16:
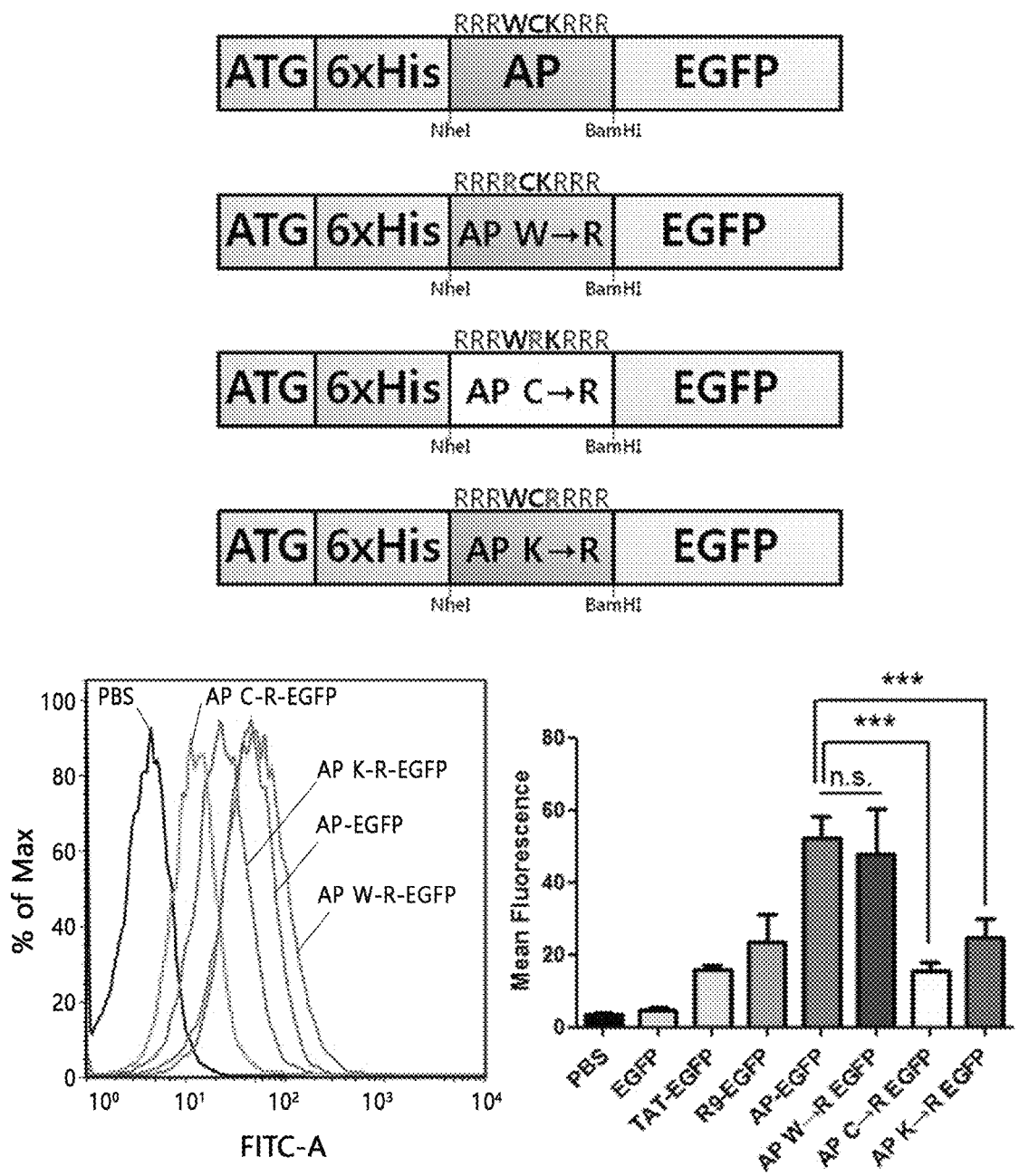
FIG. 16 shows a result of intracellular fluorescence intensity analysis by flow cytometry in Test Example 6 comparing the effect of tryptophan (X2), cysteine and lysine (First amino acid of X3) constituting AP on delivery of a protein into cells by replacing each of them with arginine.

A variant having the positively charged arginine was used as a control group for comparison of efficiency with R9 which consists of 9 arginines. As a result, the alanine variant and the arginine variant showed similar patterns. Because no significant difference in efficiency was observed when tryptophan was replaced with other amino acids, it was confirmed not to contribute significantly to the functional role of AP. When arginine was substituted with other amino acids, the efficiency decreased greatly. It is though that the positively charged arginine plays a positive role. The greatest decrease in efficiency was observed when cysteine was substituted with other amino acids. This suggests that cysteine plays a very important functional role in AP (FIG. 15 and FIG. 16).

Test Example 7: Investigation of AP's Cell-Penetrating Mechanism

In order to investigate whether AP is delivered into cells through endocytosis as the most widely known existing cell-penetrating peptide TAT, the change in intracellular delivery depending on temperature was measured and it was investigated whether it is affected by other proteins depending on the serum concentration of a medium. EGFP not linked with a cell-penetrating peptide was used as a negative control group and TAT-EGFP was used as a positive control group.

Jurkat cells were treated with each protein at 5 µM as described above at temperatures of 4° C., 25° C. and 37° C. independently for 1 hour. As a result, it was confirmed that the intracellular delivery was affected by temperature like TAT. This suggests that AP is delivered by energy-dependent endocytosis like TAT. Thus, it was confirmed that AP delivers a protein into cells in a manner similar to that of previously known cell-penetrating peptides. In addition, it was confirmed that the delivery efficiency was higher than TAT at all temperatures (FIG. 17, top).

Also, the delivery efficiency of each protein (5 µM) was analyzed when the serum concentration in an RPMI medium was 0% and 10%, respectively. After treating with each protein, the cells were cultured at 37° C. for 1 hour. EGFP not linked with a cell-penetrating peptide was used as a negative control group and TAT-EGFP was used as a positive control group.

As a result, it was confirmed that the efficiency of the delivery of the AP-EGFP protein into cells through the cell membrane decreased with the serum concentration. This suggests that the cell-penetrating peptide is affected by competition or interaction with other proteins and confirms again the function of the AP according to the present disclosure as a cell-penetrating peptide. AP showed higher delivery efficiency than the positive control groups at each serum concentration (FIG. 17, bottom).

Test Example 8: Intracellular Protein Delivery Efficiency of AP-EGFP Depending on Change in Heparin and MβCD Concentration (1) Intracellular Protein Delivery Efficiency of AP-EGFP Depending on Change in Heparin Concentration With the expectation that treatment with heparin which can interfere with binding of the cell-penetrating peptide to heparan sulfate on cell surface would directly or indirectly affect the interaction based on the delivery mechanism of AP-EGFP confirmed in Test Example 4, Jurkat cells were treated for 30 minutes with heparin (heparin sodium salt from porcine intestinal mucosa, Sigma) at different concentrations of 0 µm/mL, 10 µm/mL, 20 µm/mL and 50 µm/mL and then with 10 µm/mL AP-EGFP whose final volume was made 100 µL with D-PBS. TAT-EGFP was used as a positive control group for comparison. The cells were then cultured for 1 hour in a 5% $CO_2$ incubator at 37° C. 1 hour later, all the cells were recovered and transferred to a tube. After performing centrifugation, the supernatant was removed. A procedure of washing the cells with 1 mL of D-PBS, resuspending and then centrifuging was repeated 2 times. After the washing, the obtained cells were resuspended finally in 500 µL of D-PBS and delivery efficiency of the protein into the cells was measured by measuring intracellular fluorescence by flow cytometry using a FACS machine (FACSCanto, BD Biosciences).

Figure 18:
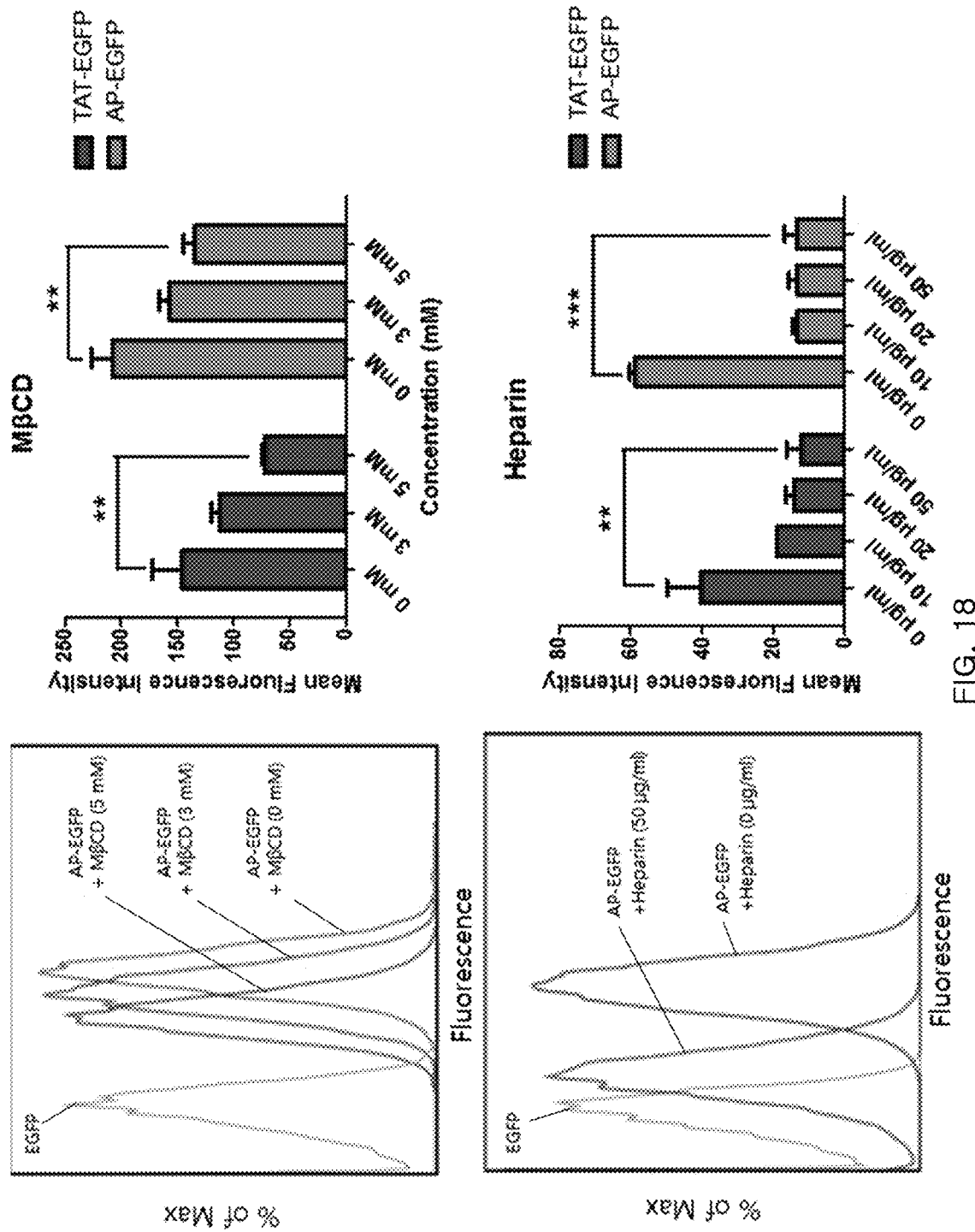
FIG. 18 shows a result of comparing the change in the intracellular delivery efficiency of AP-EGFP depending on the change in heparin and MβCD (methyl-beta-cyclodextrin) concentrations with that of existing cell-penetrating peptides as positive control groups in Test Example 8.

As a result, it was confirmed that the intracellular delivery efficiency of AP-EGFP decreases remarkably as the heparin concentration is increased (FIG. 18, top).

(2) Intracellular Protein Delivery Efficiency of AP-EGFP Depending on Change in MβCD Concentration Also, with the expectation that the intracellular delivery of AP-EGFP would be affected by endocytosis which is associated with the lipid raft constituting the phospholipid bilayer of the cell membrane, lipid-mediated endocytosis was inhibited in advance by treating with MβCD (methyl-β-cyclodextrin) which is known to remove cholesterol from the cell membrane. After treating Jurkat cells with 0 mM, 3 mM or 5 mM MβCD for 20 minutes on ice, the cells were treated with 10 μM AP-EGFP for 1 hour. TAT-EGFP was used as a positive control group for comparison. As a result, it was confirmed that the intracellular delivery efficiency of AP-EGFP decreases remarkably as the MβCD concentration is increased (FIG. 18, bottom).

This also suggests that the cell-penetrating peptide is directly or indirectly affected by competition or interaction with other proteins and confirms again the function of the AP according to the present disclosure as a cell-penetrating peptide.

Test Example 9: Delivery of AP-EGFP into HeLa Cancer Cells

In order to investigate whether AP is actually delivered into cells together with a protein and where it exists in the cells, AP-EGFP was delivered into HeLa cells, which are cervical cancer cells, and analysis was conducted using a confocal microscope.

After seeding 1×10$^5$ HeLa cells on a circular cover glass (Marinfield) in each well of a 12-well plate (SPL Life Sciences), the cells were cultured for 18 hours in a DMEM medium (HyClone) so that the cells were attached to the cover glass. After completely discarding the medium by suction and adding 450 μL of fresh DMEM, the cells were treated with the AP-EGFP protein purified in Preparation Example 3 (5 μM) whose final volume was made 50 μL by mixing with D-PBS. Then, the cells were incubated for 30 minutes in a 5% CO$_2$ incubator at 37° C. Then, after completely discarding the medium by suction to remove extracellular proteins, the cells were washed with 1 mL of D-PBS. This procedure was repeated 5 times. Then, the cells were fixed with 1 mL of formaldehyde (formaldehyde 37% solution, formalin, Sigma). After the fixation, the cells were washed 5 times with 1 mL of D-PBS. Then, the nuclei of the cells were stained with 500 μL of a Hoechst stain (Hoechst AG) diluted to 1:4000. After 10 minutes, the cells were washed 5 times with 1 mL of D-PBS. The prepared cover glass was mounted on a slide glass using a mounting medium (Sigma) and the location and intracellular delivery of the green fluorescent protein were observed using the fluorescence microscope DMi-8 (Leica). As a result, it was confirmed that the AP-linked green fluorescent protein is delivered into cells through the cell membrane and is present in the cytoplasm (FIG. 19).

Test Example 10: Delivery of AP-EGFP into HaCaT and NIH3T3 Skin Cells

In order to investigate whether AP is actually delivered into skin cells together with a protein and where it exists in the skin cells, AP-EGFP was delivered into HaCaT and NIH3T3 skin cells and analysis was conducted using a confocal microscope in the same manner as in Test Example 9. TAT-EGFP and R9-EGFP were used as positive control groups for comparison. In addition, AP C→A EGFP in which the cysteine of the AP sequence was replaced with alanine was used as another test group.

Figure 20:
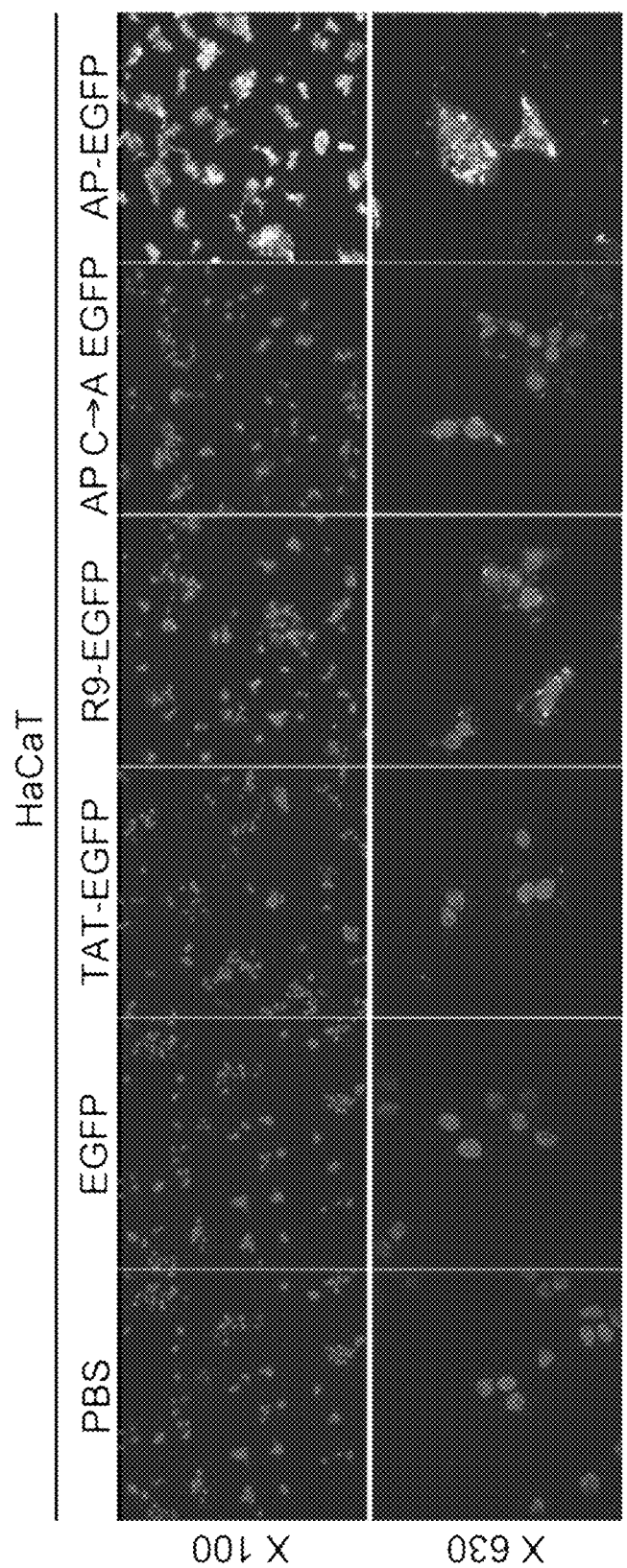
FIG. 20 shows a result of intracellular fluorescence intensity analysis comparing the delivery of a protein into skin epidermal HaCaT cells by AP and intracellular localization with those of existing cell-penetrating peptides as positive control groups by confocal microscopy in Test Example 10.
Figure 21:
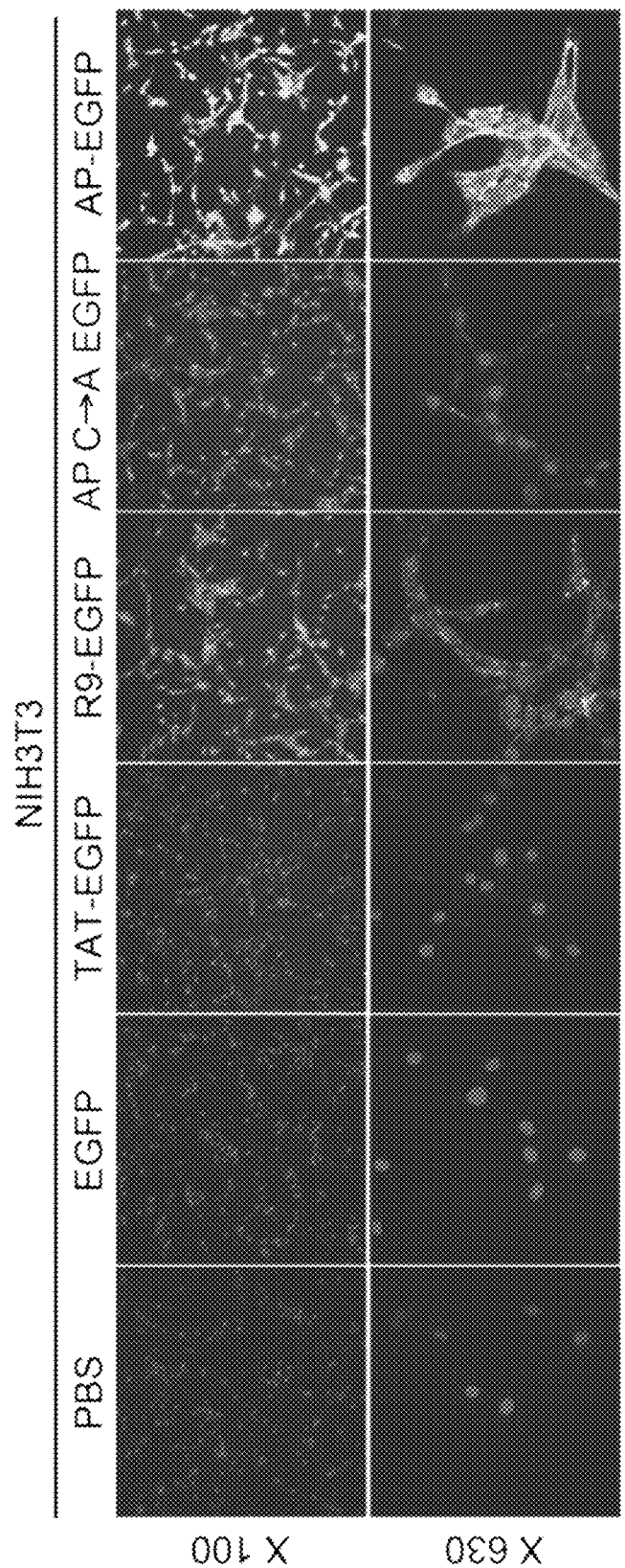
FIG. 21 shows a result of intracellular fluorescence intensity analysis comparing the delivery of a protein into skin dermal NIH3T3 cells by AP and intracellular localization with those of existing cell-penetrating peptides as positive control groups by confocal microscopy in Test Example 10.

As a result, it was confirmed that the AP-linked green fluorescent protein is delivered into the skin cells through the cell membrane at higher efficiency than the positive control groups or C→A EGFP and is present in the nucleus and cytoplasm (FIG. 20 and FIG. 21).

Test Example 11: Delivery of AP-EGFP into Mouse Organs

Figure 22:
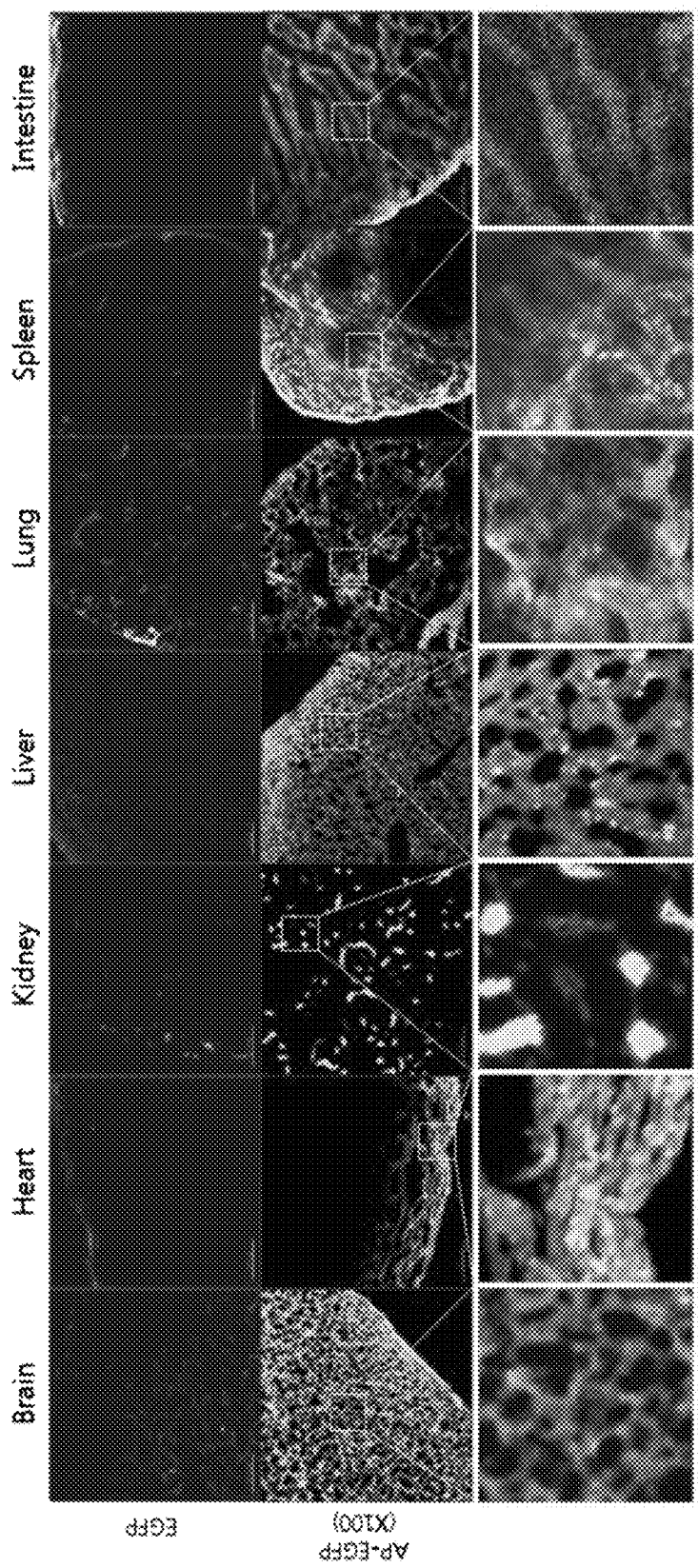
FIG. 22 shows fluorescence microscopic images showing that AP-EGFP is delivered into the cells of different mouse organs in Test Example 11.

In order to investigate whether AP is delivered under the actual in-vivo condition and, if so, how much can be delivered to which organs, 5 mg of the AP-EGFP protein was intraperitoneally injected to a 6-week-old female C57BL/6 mouse. 2 hours later, organs such as the brain, heart, kidney, liver, lung, spleen, intestine, etc. were taken and fixed with 4% paraformaldehyde. After washing 2-3 times with D-PBS, frozen blocks were prepared using the OCT compound. After preparing 6 μm-thick sections using a cryostat, the slide samples were observed under a fluorescence microscope in order to confirm the delivery of AP-EGFP into the organ cells. The slide samples were stained with a Hoechst stain for 10 minutes and the intracellular delivery was investigated by overlapping with the fluorescent protein. EGFP not linked with a cell-penetrating peptide was used as a control group. As a result, it was confirmed that the AP-linked green fluorescent protein was delivered much better into the cells of the brain, heart, kidney, liver, lung, spleen, intestine, etc. than EGFP (FIG. 22).

Test Example 12: Delivery of AP-EGFP into Mouse Skin with Time

In order to investigate whether AP is delivered to skin tissues and, if so, how deep it can be delivered, a 7-week-old female C57BL/6 mouse was depilated and, after removing the stratum corneum from the skin by attaching and detaching an adhesive tape 10 times, 100 μg of AP-EGFP was attached using a paper patch. 2, 4, 6 and 8 hours later, skin tissues were taken and fixed with 4% paraformaldehyde. Then, frozen blocks were prepared using the OCT compound. After preparing 7 μm-thick sections using a cryostat, the slide samples were observed under a fluorescence microscope in order to confirm the delivery of AP-EGFP into the skin tissues. The slide samples were stained with a Hoechst stain for 15 minutes and the intracellular delivery was investigated by overlapping with the fluorescent protein. TAT-EGFP fused with an existing cell-penetrating peptide was used as a positive control group.

Figure 23:
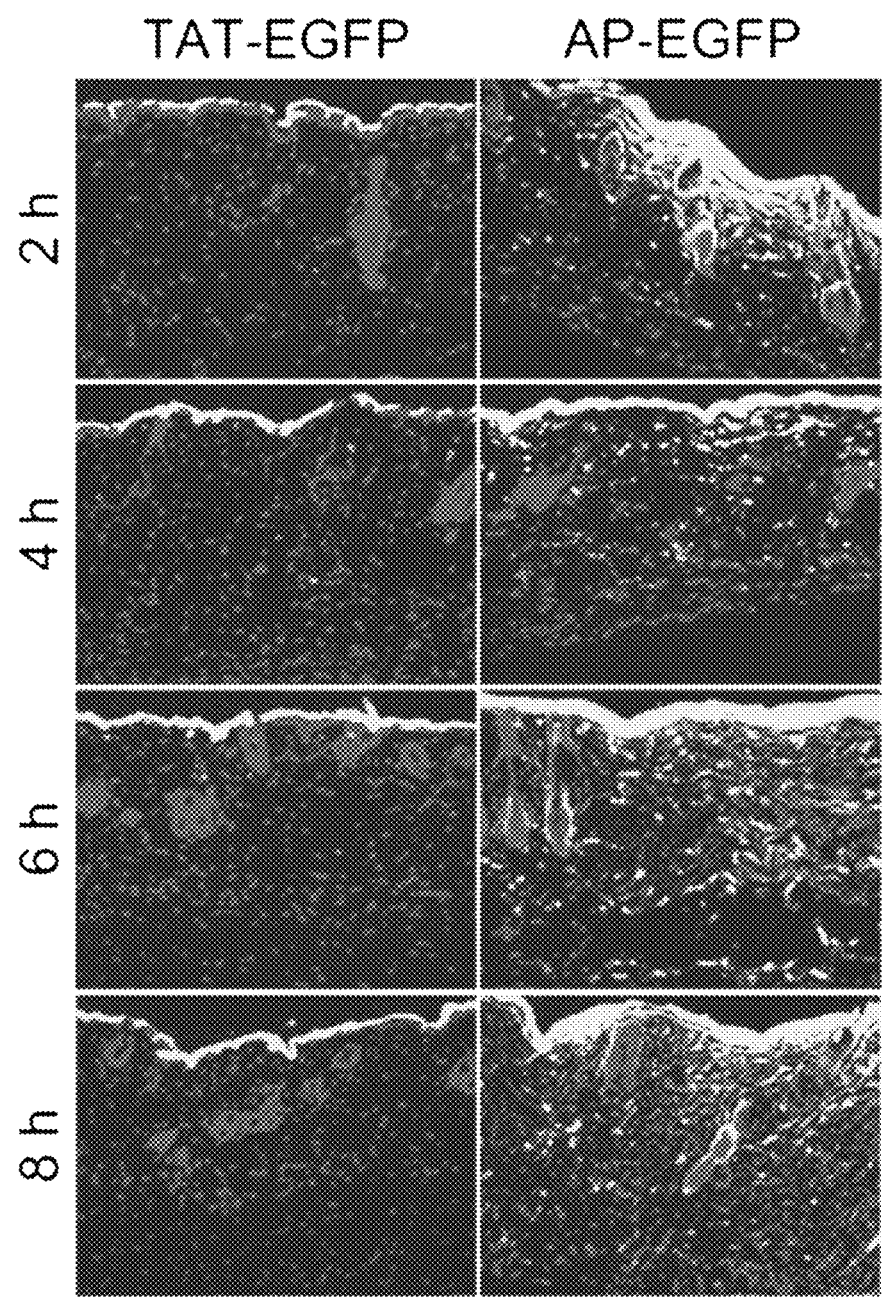
FIG. 23 shows fluorescence microscopic images comparing the change in the delivery efficiency of AP-EGFP into mouse skin tissues with time with that of existing cell-penetrating peptides as positive control groups in Test Example 12.

Whereas TAT-EGFP could not deliver the green fluorescent protein into the skin tissues until 8 hours, the AP-linked green fluorescent protein (AP-EGFP) was delivered distinctly into the cells constituting the skin tissues after 2 hours (FIG. 23).

Test Example 13: Comparison of Protein Delivery Efficiency of AP-dTomato into Mouse Skin with Existing Skin-Penetrating Peptides It was investigated whether the AP of the present disclosure linked with the dTomato fluorescent protein having a large molecular weight can deliver the fluorescent protein to skin tissues as compared with existing skin-penetrating peptides. As in Test Example 3, the dTomato fluorescent protein not linked with a skin-penetrating peptide was used as a negative control group and TAT-dTomato, TDP1-dTomato and TDP2-dTomato in which the dTomato fluorescent protein was linked with each skin-penetrating peptide were used as positive control groups for comparison. Experiment was conducted in the same manner as in Test Example 12, except that skin tissues were taken 6 hours later.

Figure 24:
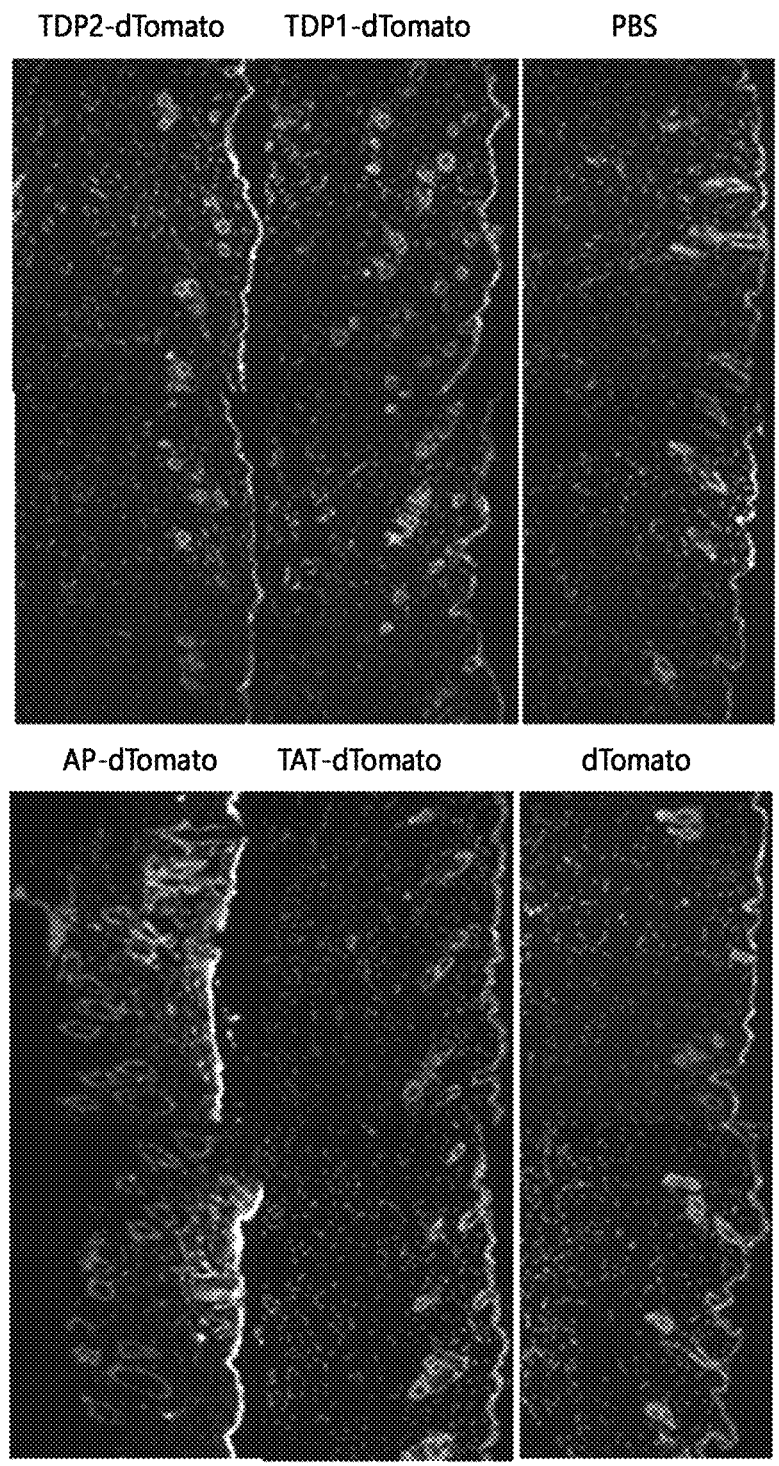
FIG. 24 shows fluorescence microscopic images comparing the change in the delivery efficiency of AP-dTomato into mouse skin with that of existing cell-penetrating peptides in Test Example 13.

It was confirmed that only the AP-dTomato of the present disclosure delivers the dTomato fluorescent protein into the skin tissues (FIG. 24).

Test Example 14: Delivery of AP-dTomato into Skin of Green Fluorescent Protein-Targeted Mouse In order to clarify that the AP of the present disclosure is delivered into the skin cells of skin tissues, the AP-dTomato fluorescent protein was attached to the skin of a GFP gene-targeted mouse expressing the green fluorescent protein (GFP) in all cells using a paper patch in the same manner as in Test Example 12. 6 hours later, skin tissues were taken and fixed with 4% paraformaldehyde. Then, frozen blocks were prepared using the OCT compound. After preparing 20 μm-thick sections using a cryostat, the slide samples were observed under a fluorescence microscope in order to confirm the delivery of AP-EGFP into the skin tissues.

The slide samples were stained with a Hoechst stain for 15 minutes and the intracellular delivery was investigated by overlapping with the fluorescent protein. The result is shown in FIG. 25 and FIG. 26. dTomato not linked with a skin-penetrating peptide was used as a negative control group.

Figure 25:
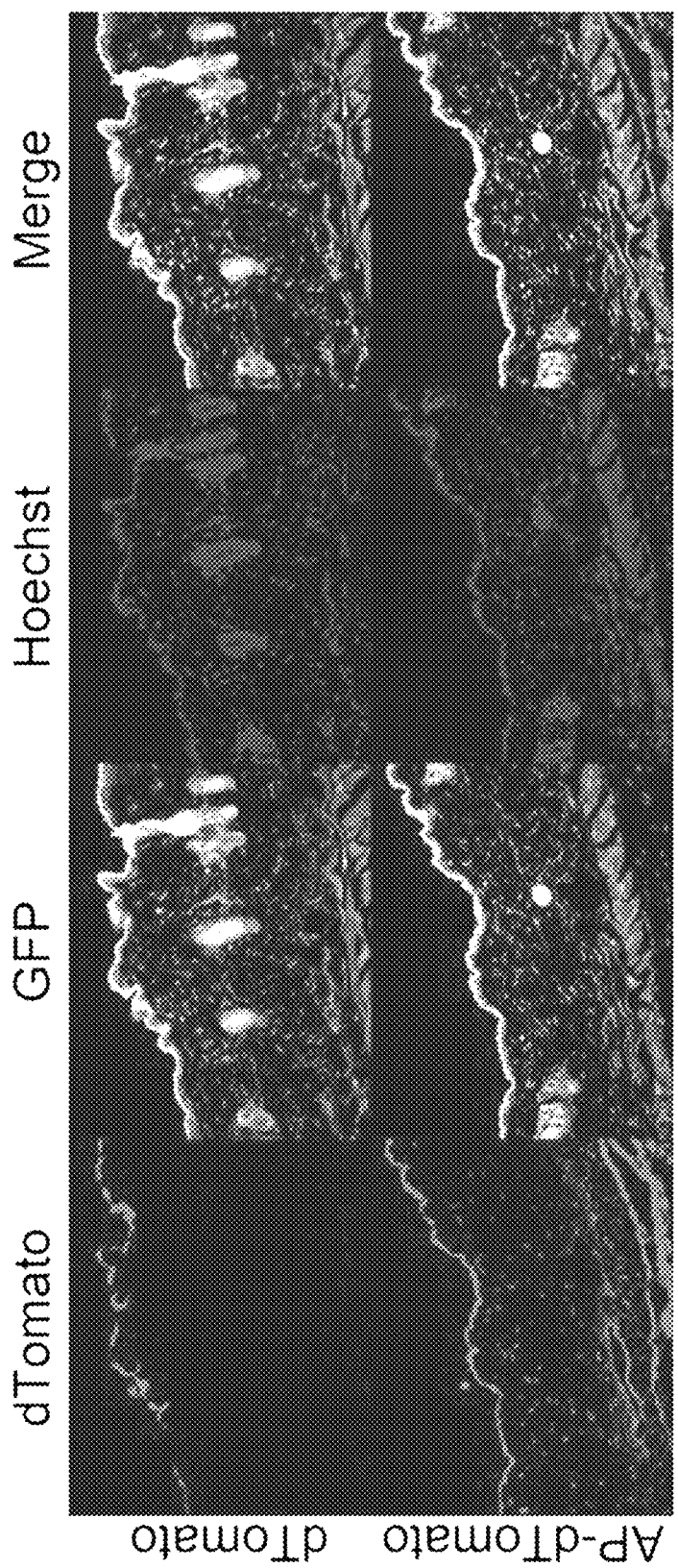
FIG. 25 shows confocal microscopic images showing that AP-dTomato is delivered into the skin of green fluorescent protein-targeted mouse in Test Example 14.
Figure 26:
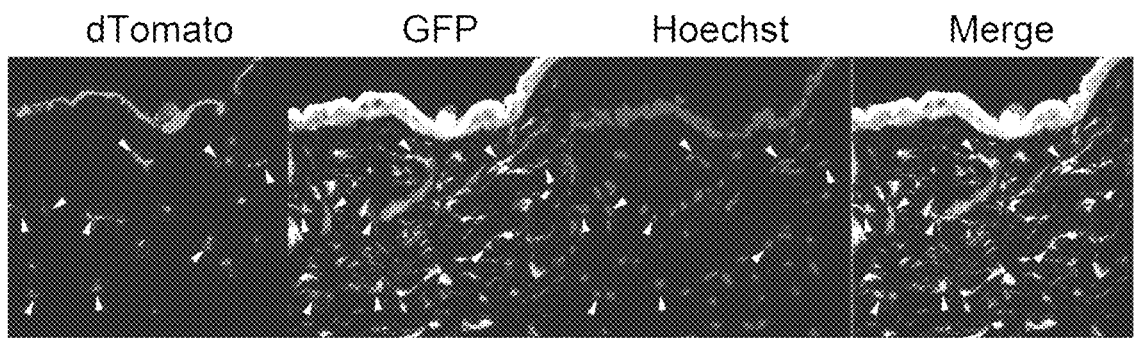
FIG. 26 shows magnified images of FIG. 25.

As a result, it was distinctly confirmed that the red fluorescent protein linked with AP was delivered into the cells constituting the skin tissues as compared to dTomato (FIG. 25). The delivery of the AP-dTomato fluorescent protein into the GFP-expressing green cells was also confirmed through images at higher magnification (FIG. 26).

Test Example 15: Expression of AP-EGFP Protein and AP-rPTP Protein in *E. coli* and Purification The AP-EGFP protein purified in Preparation Example 4 and the AP-rPTP protein purified in Preparation Example 7 were subjected to 12% SDS gel electrophoresis. The result is shown in FIG. 27.

Figure 27:
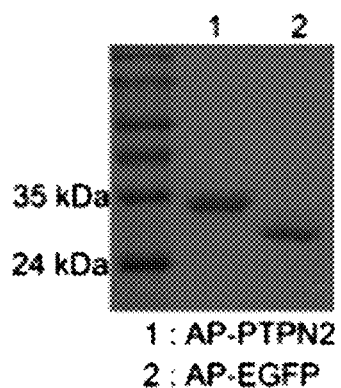
FIG. 27 shows a result of 12% SDS gel electrophoresis of an AP-EGFP protein purified in Preparation Example 4 and an AP-rPTP protein purified in Preparation Example 7.

As seen from FIG. 27, the two proteins were expressed properly in *E. coli* and were purified well.

Test Example 16: 3-Dimensional Structure of AP-rPTP Protein

Figure 28:
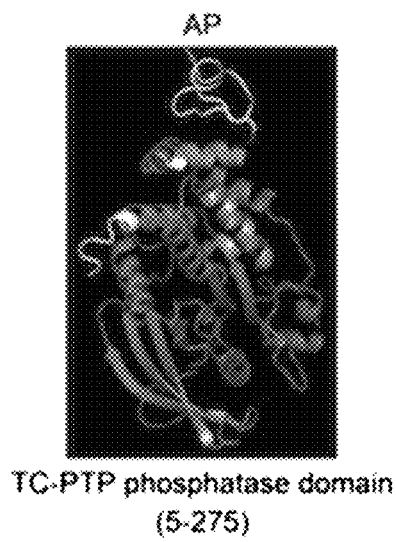
FIG. 28 shows the 3-dimensional structure of an AP-rPTP protein predicted in Test Example 16.

FIG. 28 shows a predicted 3-dimensional structure of the AP-rPTP protein purified in Preparation Example 7. It was predicted by Sparks X (http://sparks-lab.org) and visualized using PyMOL.

As seen from FIG. 28, the AP-rPTP protein maintained the 3-dimensional structure of the rPTP protein almost intact and no rapid change in structure was observed.

Test Example 17: Measurement of Phosphatase Activity of AP-EGFP Protein and AP-rPTP Protein FIG. 29 shows a result of investigating the phosphatase activity of the AP-EGFP protein purified in Preparation Example 4 and the AP-rPTP protein purified in Preparation Example 7.

For measurement of the phosphatase activity of the AP-EGFP protein and the AP-rPTP protein, the pNPP (para-nitrophenylphosphate) assay (BioAssay 517 Systems, Hayward, Calif., USA) was conducted after adding a colorimetric substrate to the AP-EGFP protein and the AP-rPTP protein.

From the obtained data, the initial rate ($V_0$) was plotted against the protein concentration. Statistical analysis was conducted by one-way ANOVA (*P<0.001).

Figure 29:
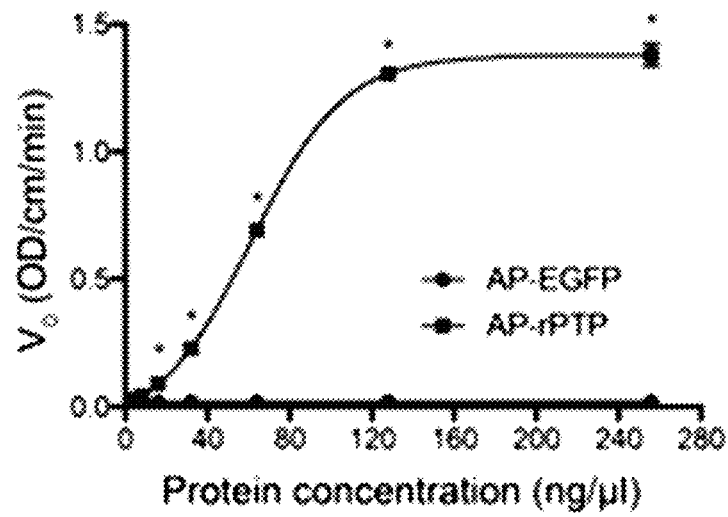
FIG. 29 shows a result of investigating the phosphatase activity of an AP-EGFP protein and an AP-rPTP protein in Test Example 17.

As seen from FIG. 29, the AP-rPTP protein showed a phosphatase activity of 1.5 nmol/min/μg, whereas no activity was detected for the AP-EGFP protein.

Test Example 18: Investigation of Delivery Efficiency of AP-rPTP Protein into Skin Cells HaCaT cells are human epidermal cells used in research of in-vitro delivery efficiency and mechanism related with transdermal delivery and skin diseases [*J Invest Dermatol.* 2011 July 131(7): 1477-85; *Biochem Pharmacol.* 2008 Mar. 15; 75(6): 1348-57].

Figure 30:
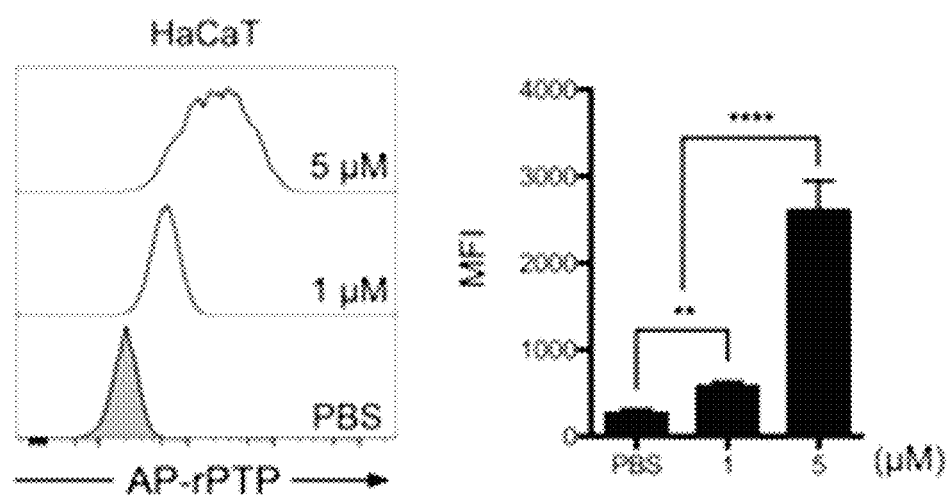
FIG. 30 shows a result of intracellular fluorescence intensity analysis by flow cytometry of the efficiency of the delivery of a protein into skin epidermal HaCaT cells by AP-rPTP in Test Example 18.

It was investigated whether the AP-rPTP protein of the present disclosure can be delivered to skin cells using HaCaT cells. The result is shown in FIG. 30. The AP-rPTP protein was stained with an anti-His tag antibody. The signal was amplified by the Alexa Fluor-488-conjugated anti-mouse IgG antibody and the intracellular fluorescence intensity was measured by flow cytometry.

FIG. 30 shows the result of intracellular fluorescence intensity analysis by flow cytometry of the protein delivery efficiency of the AP-rPTP prepared in Preparation Example 7 into skin epidermal HaCaT cells. In FIG. 30, the x-axis of the right-side graph stands for MFI, or 'mean fluorescence intensity'.

As seen from FIG. 30, after treatment with 1 μM or 5 μM AP-rPTP protein for 1 hour, the AP-rPTP protein was delivered into the cells with very superior efficiency.

Test Example 19: Investigation of Delivery Efficiency of AP-rPTP Protein into Skin Cells with Time HaCaT cells are human epidermal cells used in research of in-vitro delivery efficiency and mechanism related with transdermal delivery and skin diseases [*J Invest Dermatol.* 2011 July 131(7): 1477-85; *Biochem Pharmacol.* 2008 Mar. 15; 75(6): 1348-57].

Figure 31:
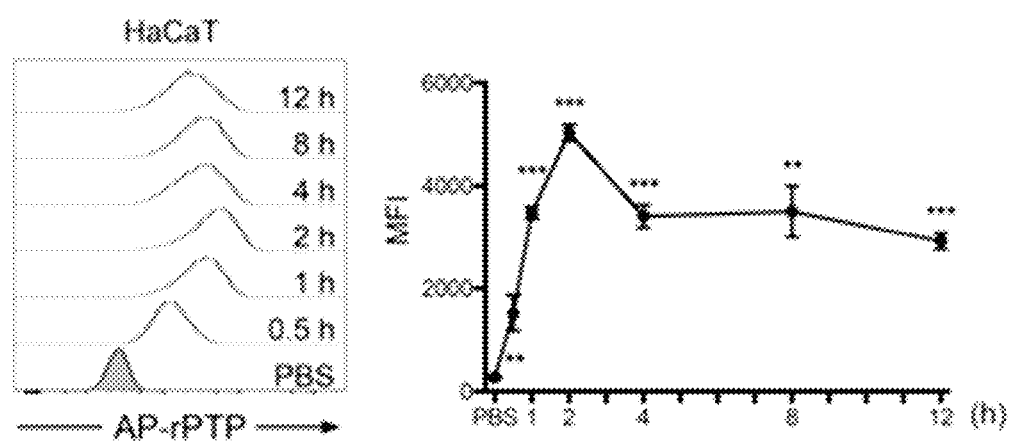
FIG. 31 shows a result of intracellular fluorescence intensity analysis by flow cytometry of comparing the efficiency of the delivery of a protein into skin epidermal HaCaT cells by AP-rPTP with time in Test Example 19.

After treating HaCaT with the AP-rPTP protein for different times (0.5-12 hours), the delivery efficiency to the skin cells was compared (FIG. 31).

The AP-rPTP protein was stained with an anti-His tag antibody. The signal was amplified by the Alexa Fluor-488-conjugated anti-mouse IgG antibody and the intracellular fluorescence intensity was measured by flow cytometry.

FIG. 31 shows the result of intracellular fluorescence intensity analysis by flow cytometry of comparing the efficiency of the delivery of the protein into skin epidermal HaCaT cells by the AP-rPTP protein prepared in Preparation Example 7 with time. In FIG. 31, the x-axis of the right-side graph stands for MFI, or 'mean fluorescence intensity'.

As seen from FIG. 31, the maximum fluorescence intensity was achieved after 2 hours. The fluorescence intensity decreased rapidly thereafter and was maintained stable after 12 hours. Through this, it was it was confirmed that the AP-rPTP protein of the present disclosure can achieve a sufficient intracellular delivery efficiency in 1-8 hours. Most specifically, an intracellular delivery efficiency of 1.5 times or higher can be achieved by treating for 1.5-3.5 hours.

Test Example 20: Investigation of Cytokine Signaling Inhibition Efficiency of AP-rPTP Protein in Splenocytes It was investigated whether the AP-rPTP protein can inhibit cytokine signaling. Specifically, splenocytes taken from 6- to 8-week-old C57BL/6 mice were incubated with PBS, AP-rPTP and AP-EGFP respectively for 1 hour at 37° C. and then activated with cytokines, recombinant mouse IFN-γ (10 ng/mL; BD), IL-4 (20 ng/mL; BD) and IL-6 (30 ng/mL; BD). The cells were washed for 30 minutes with PBS and a RIPA buffer (Cell Signaling, Beverly, Mass., USA) (1 mM NaF, 1 mM PMSF, Halt protease and phosphatase inhibitor cocktail (Thermo Fisher Scientific, Waltham, Mass., USA)) on ice.

Tyrosine phosphorylation of the STAT protein for each cytokine stimulation was measured by immunoblotting. The immunoblotting was conducted using a PVDF membrane (Bio-Rad) and phospho-Stat1 (Tyr701) rabbit mAb, phopspho-Stat3 (Tyr705) rabbit mAb and phospho-Stat6 (Tyr641) rabbit mAb as primary antibodies. The reagents were purchased from Cell Signaling and β-actin mouse mAb was purchased from Santa Cruz Biotechnology (CA, USA).

Figure 32:
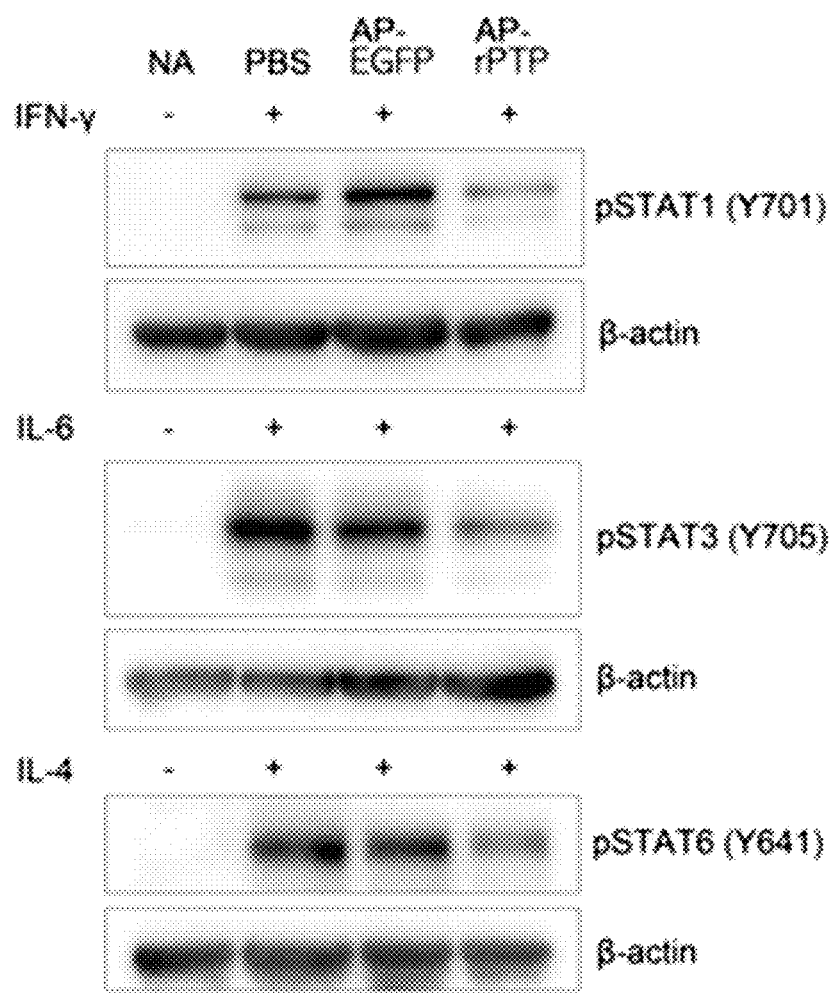
FIG. 32 shows images showing the effect of stimulation by cytokines in mouse splenocytes treated with an AP-rPTP protein in Test Example 20.

FIG. 32 shows the effect of the stimulation by cytokines in mouse splenocytes treated with the AP-rPTP protein. IFN-γ, IL-6 and IL-4 marked on the upper left corner of each band indicate stimulation by the corresponding cytokines.

NA means no activation of immune cells and corresponds to a negative control group. PBS means stimulation with IFN-γ, IL-6 or IL-4 for activation of immune cells and corresponds to a positive control group. The representative results of four independent experiments were presented (n=4).

As seen from FIG. 32, the result of incubating with the AP-rPTP or AP-EGFP protein for 1 hour, stimulating with IFN-γ, IL-6 or IL-4 for 60 minutes, 30 minutes or 15 minutes, respectively, and comparing the phosphorylation degree of the STAT protein confirms that the treatment with the AP-rPTP protein resulted in significantly decreased phosphorylation of STAT1, STAT3 and STAT6.

To conclude, it is thought that the AP-rPTP protein according to the present disclosure negatively regulates cytokine signaling in immune cells.

Test Example 21: Investigation of Proliferation Efficiency of CD4 T Cells in Splenocytes by AP-rPTP Protein It was investigated whether the AP-rPTP protein according to the present disclosure can also regulate the activity of T cells.

0.1 μg of anti-CD3 and anti-CD28 antibodies were coated on a 96 well plate in a 0.5% $CO_2$ incubator at 37° C. for 5 hours. Then, isolated mouse splenocytes were inoculated, with $2.5 \times 10^5$ cells per well. After treating with PBS or the AP-rPTP protein, the cells were cultured for 3 days in a 0.5% $CO_2$ incubator at 37° C. Then, the cells were fluorescence-stained with CFSE (Invitrogen, Carlsbad, Calif., USA) at 4° C. for 20 minutes. Then, CFSE signals from the prepared cells were analyzed by flow cytometry (FACS).

Figure 33:
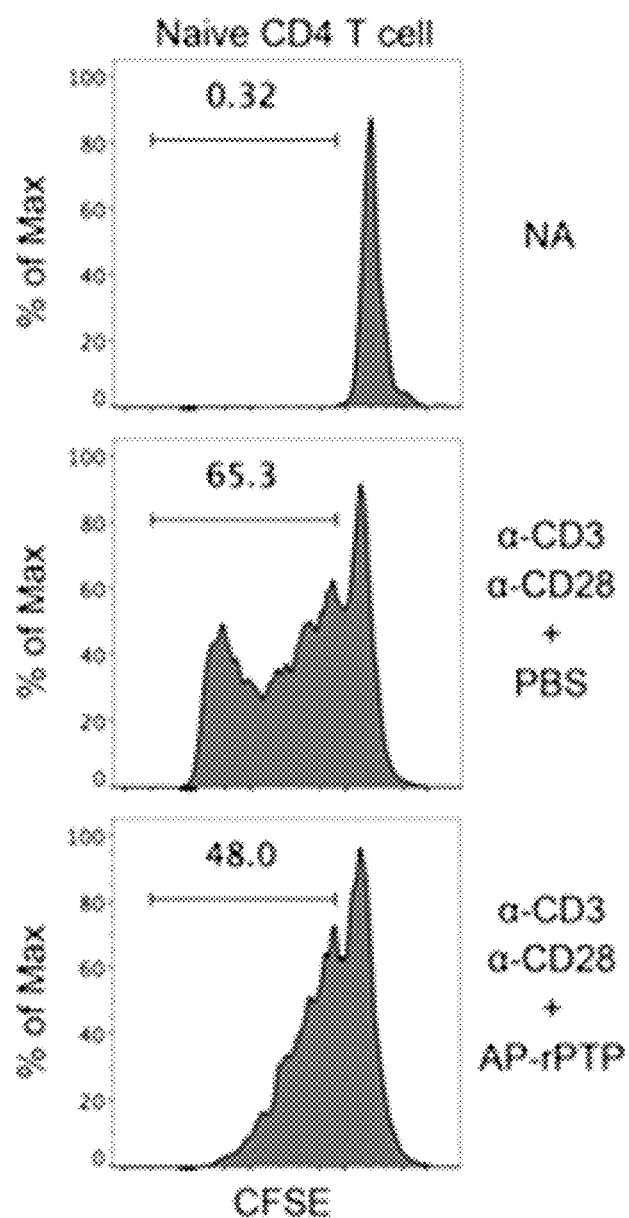
FIG. 33 shows a result of measuring the proliferation of primary mouse CD4−T cells treated with NA or PBS ('NA' and 'α-CD3αCD28+PBS'; a, b) and the proliferation of primary mouse CD4−T cells treated with an AP-rPTP protein (c) in Test Example 21.
Figure 34A:
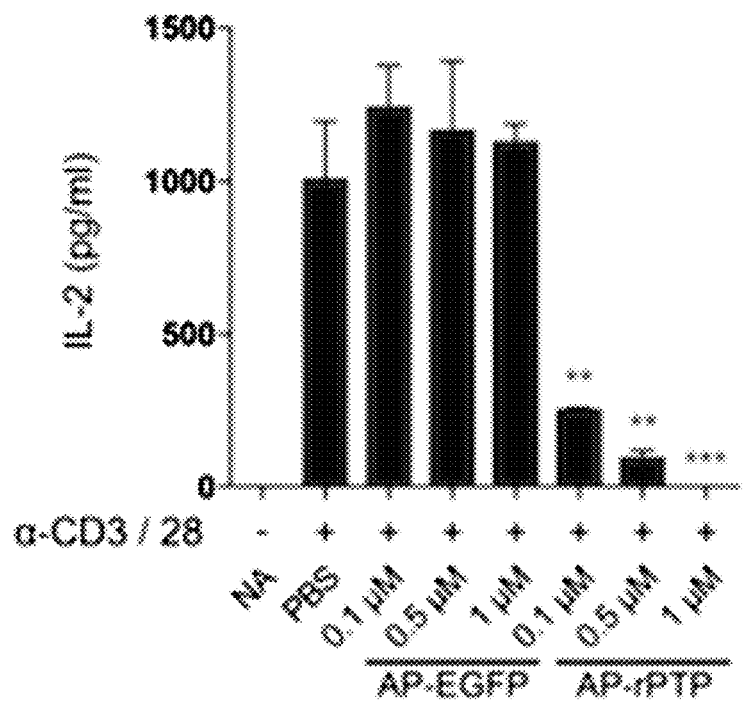
FIGS. 34a-34d show a result of measuring the expression level of cytokines IL-17 (34a), IL-13 (34b), IFN-γ (34c) and IL-2 (34d) in mouse splenocytes treated with an AP-rPTP or AP-EGFP protein in Test Example 22.
Figure 34B:
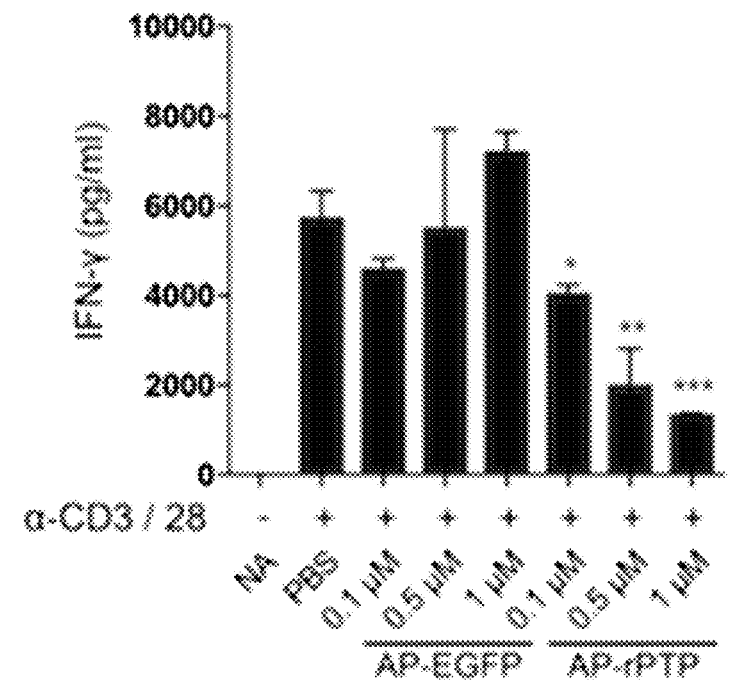
Figure 34C:
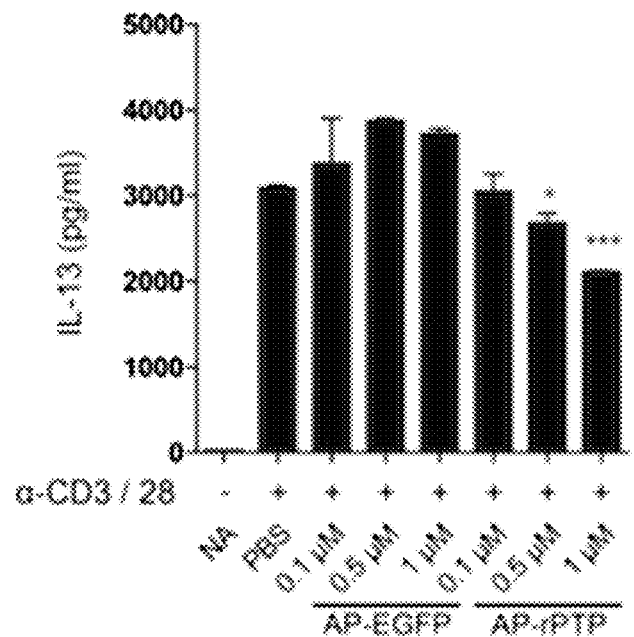
Figure 34D:
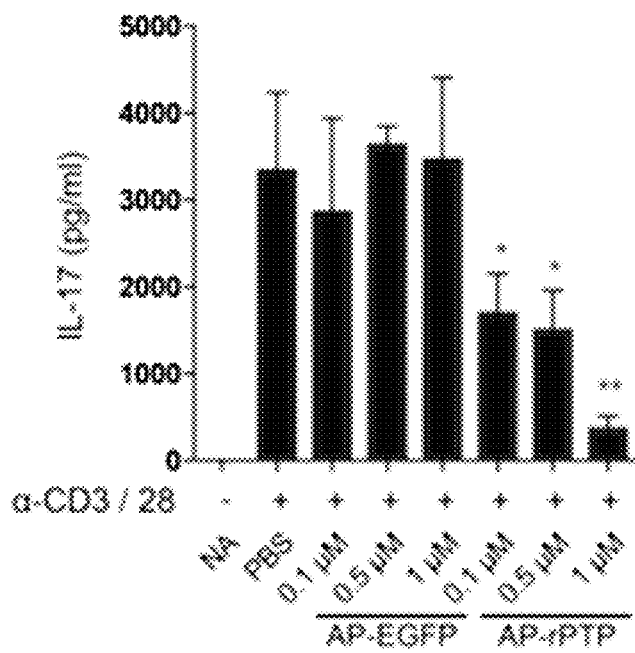

FIG. 33 shows the result of measuring the proliferation of primary mouse CD4-T cells treated with NA or PBS ('NA' and 'α-CD3αCD28+PBS'; a, b) and the proliferation of primary mouse CD4-T cells treated with the AP-rPTP protein (c).

NA means no activation of T cells and corresponds to a negative control group. PBS means stimulation with anti-CD3 and anti-CD28 monoclonal antibodies for activation of T cells and corresponds to a positive control group.

As seen from FIG. 33, as a result of investigating the cytokine production from activated T cells and the proliferation of CD4 T cells by stimulating with anti-CD3 and anti-CD28 antibodies, it was confirmed that AP-rPTP significantly decreases the proliferation of activated T cells.

Test Example 22: Comparison of Cytokine Expression Level of AP-rPTP

Protein and AP-EGFP Protein in Splenocytes 2 μg/mL (BD Pharmingen) anti-CD3 and anti-CD28 antibodies were coated on a 96-well plate in a 0.5% $CO_2$ incubator at 37° C. for 5 hours. Then, isolated mouse splenocytes were inoculated, with $2.5 \times 10^5$ cells per well. After treating with the AP-EGFP protein or the AP-rPTP protein, the cells were cultured for 3 days in a 0.5% $CO_2$ incubator at 37° C. Then, the cell culture supernatant was subjected to ELISA analysis for IFN-γ (BioLegend), IL-2 (BioLegend), IL-13 (Ebioscience) and IL-17 (Ebioscience). The result is shown in FIG. 34. An ELISA kit purchased from BioLegend was used and the ELISA analysis was conducted according to the standard protocol.

FIGS. 34a-34d show the result of measuring the expression level of cytokines IL-17 (34a), IL-13 (34b), IFN-γ (34c) and IL-2 (34d) in mouse splenocytes treated with the AP-rPTP or AP-EGFP protein. All data are mean values of at least three experiments. The data are represented as mean±s.e.m. (*: $p<0.05$; : $p<0.01$; *: $p<0.001$). The statistical analysis was conducted by one-way ANOVA.

As seen from FIGS. 34a-34d, it was confirmed that the production of various cytokines including IL-2, IFN-γ, IL-13 and IL-17 were significantly decreased in a concentration (dose)-dependent manner. This result confirms that the AP-rPTP protein according to the present disclosure can act as a potential immune modulator that regulates not only inflammatory cytokine signaling but also the activity and proliferation of T cells.

Figure 35:
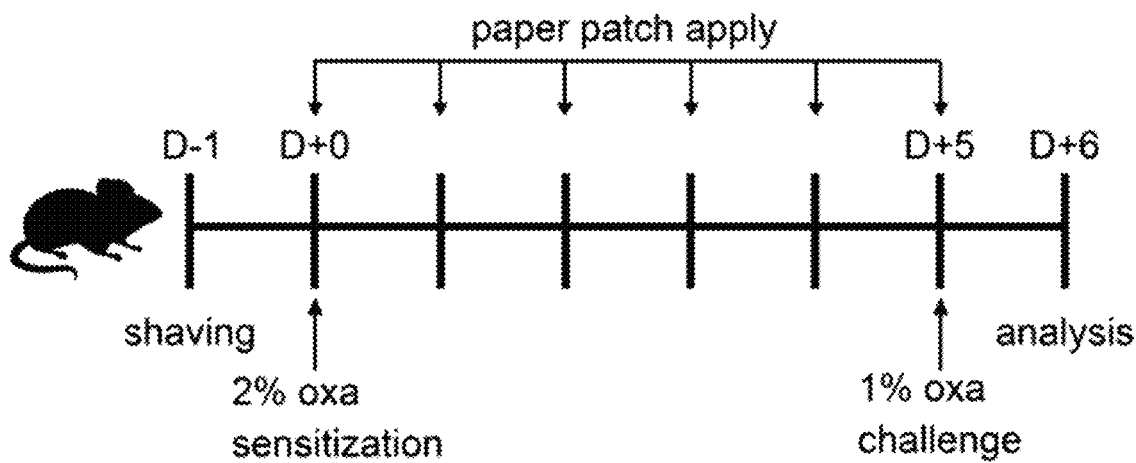
FIG. 35 shows a scheme of an oxazolone-induced contact dermatitis animal model of Test Example 23.

Test Example 23: Investigation of Therapeutic Effect of AP-rPTP Protein in Oxazolone-Induced Contact Dermatitis Animal Model After depilating a 7-week-old female C57BL/6 mouse, the mouse ear was sensitized the next day by spraying 10 μL of a 2% oxazolone solution in acetone:olive oil (4:1). 5 days after the sensitization, a 1% oxazolone solution was sprayed in the same manner to induce dermatitis. Between the sensitization and induction, 100 μg of the AP-rPTP protein was applied on both sides of the ear using a paper patch for a total of 6 times. Analysis was conducted on the next day of the induction with 1% oxazolone (FIG. 35).

Figure 36:
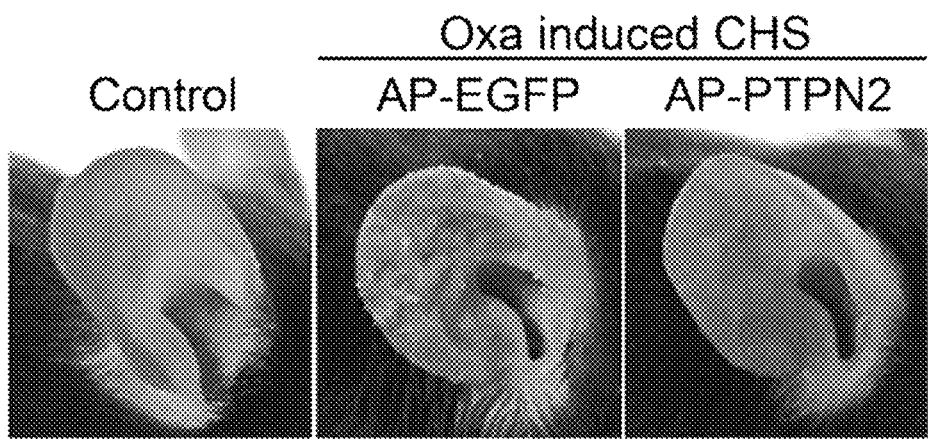
FIG. 36 shows a result of observing the ear of a contact dermatitis-induced mouse 6 days after sensitization in Test Example 23. It can be seen that the treatment with AP-rPTP reduces inflammation in the mouse ear.
Figure 37:
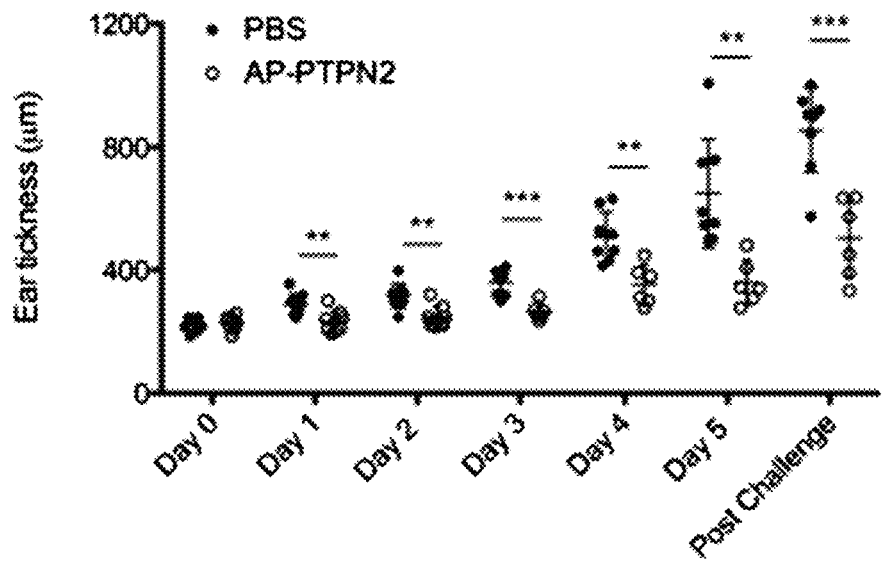
FIG. 37 shows that the ear thickness of a mouse group treated with AP-rPTP is decreased as compared to a PBS-treated control mouse group in Test Example 23.
Figure 38:
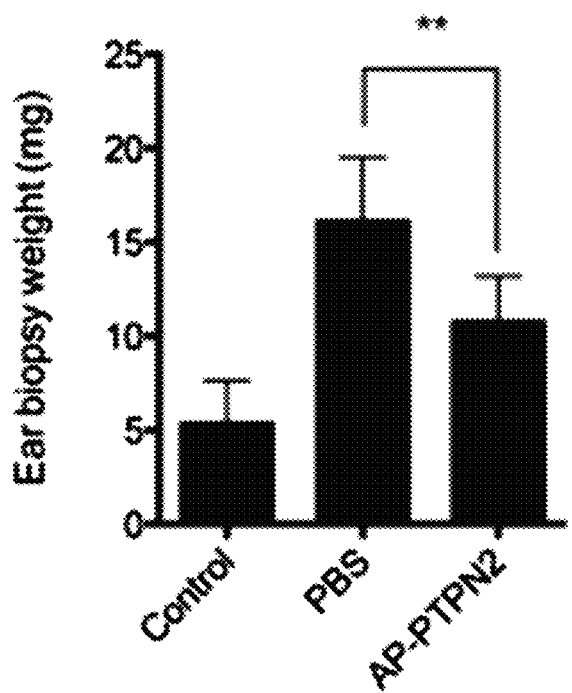
FIG. 38 shows that the ear weight of a mouse group treated with AP-rPTP is decreased as compared to a PBS-treated control mouse group in Test Example 23.

As a result, it was confirmed that the ear of the AP-rPTP-applied mouse group showed reduced inflammation as compared to the ear of a negative control group treated with PBS (FIG. 36). As a result of measuring ear thickness using a micrometer (Mitutoyo), it was confirmed that the ear thickness of the AP-rPTP-applied group was decreased as compared to the negative control group (FIG. 37). Also, the decrease in ear weight was observed (FIG. 38).

Figure 39:
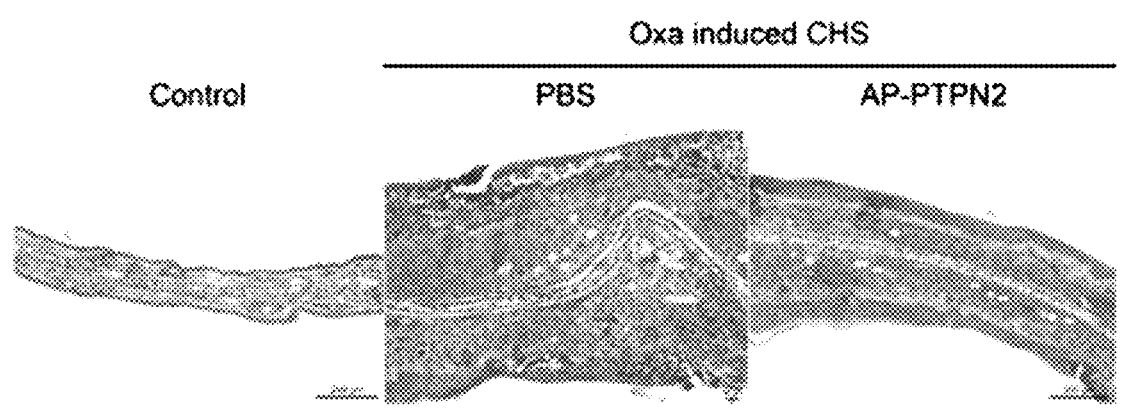
FIG. 39 shows optical microscopic images showing the difference in the ear thickness of a mouse group treated with AP-rPTP and a PBS-treated control mouse group after staining with H&E in Test Example 23.

More specifically, the ear was fixed with 4% formaldehyde for one day and frozen blocks were prepared using the OCT compound after dehydrating tissues by immersing in 30% sucrose for one day. After preparing 10 μm-thick sections, the sections were stained with H&E and observed under an optical microscope. As a result, it was confirmed that the ear thickness was decreased as compared to the negative control group (FIG. 39).

Although experiments were also conducted with a TAT-rPTP fusion product or an R9-rPTP fusion product, in which the existing cell-penetrating peptides were used instead of AP, in order to investigate the rPTP-mediated regulatory function of pathological conditions, it was confirmed that they do not exhibit regulatory function unlike AP-rPTP. That is to say, they did not show significant change as compared to the negative control group.

Figure 40:
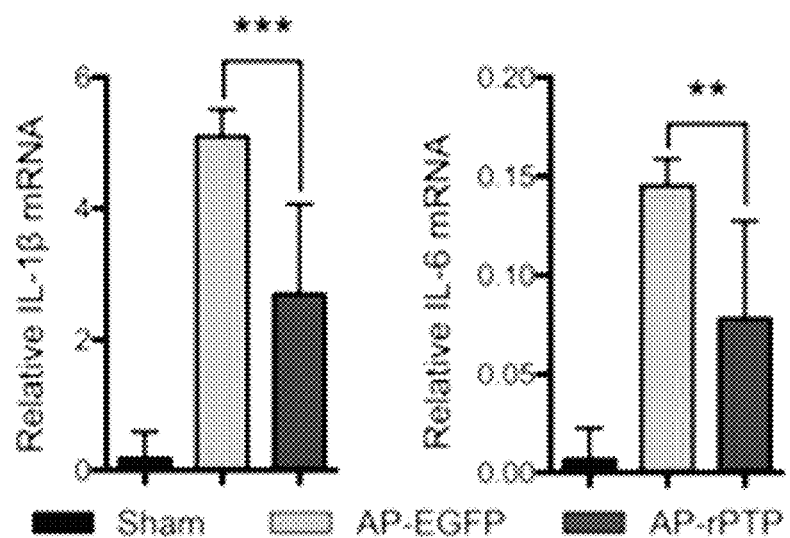
FIG. 40 shows a result of quantifying the mRNA expression level of cytokines (IL-1β, IL-6) in the skin of an oxazolone-induced contact dermatitis animal model in Test Example 24.
Figure 41:
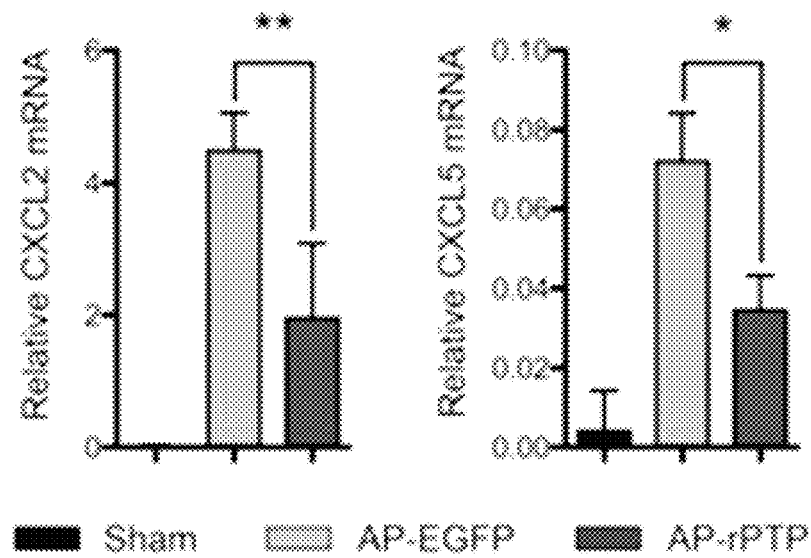
FIG. 41 shows a result of quantifying the mRNA expression level of chemokines (CXCL2, CXCL5) in the skin of an oxazolone-induced contact dermatitis animal model in Test Example 24.

Test Example 24: Comparison of Cytokine and Chemokine mRNA Expression in Skin of Oxazolone (OXA)-Induced Contact Dermatitis Animal Model The expression level of cytokine (IL-1β, IL-6) mRNA in the skin of the oxazolone-induced contact dermatitis animal model prepared in Test Example 23 was measured and quantified. The result is shown in FIG. 40. Also, a result of quantifying the expression level of chemokine (CXCL2, CXCL5) mRNA is shown in FIG. 41.

It was confirmed that treatment with the AP-rPTP protein according to the present disclosure (red) showed similar expression levels of cytokines and chemokines to those of the sham (black, control group). Treatment with the AP-EGFP protein (green) resulted in significantly increased expression levels of cytokines and chemokines as compared to the treatment with the AP-rPTP according to the present disclosure. The cytokine expression level was increased to 2 times or higher and the chemokine expression level was increased up to 3 times.

In other words, it was confirmed that the AP-rPTP protein can effectively control the inflammatory response of skin tissues suffering from OXA-induced acute dermatitis.

Test Example 25: Investigation of Preventive and Therapeutic Effects of AP-rPTP Protein in Ovalbumin (OVA)-Induced Chronic Dermatitis Animal Model After depilating a 7- to 8-week-old female BALB/c mouse, 100 μg of ovalbumin (OVA) was applied on the back using a sterilized gauze. This procedure was repeated 3 times for 1 week.

Figure 42:
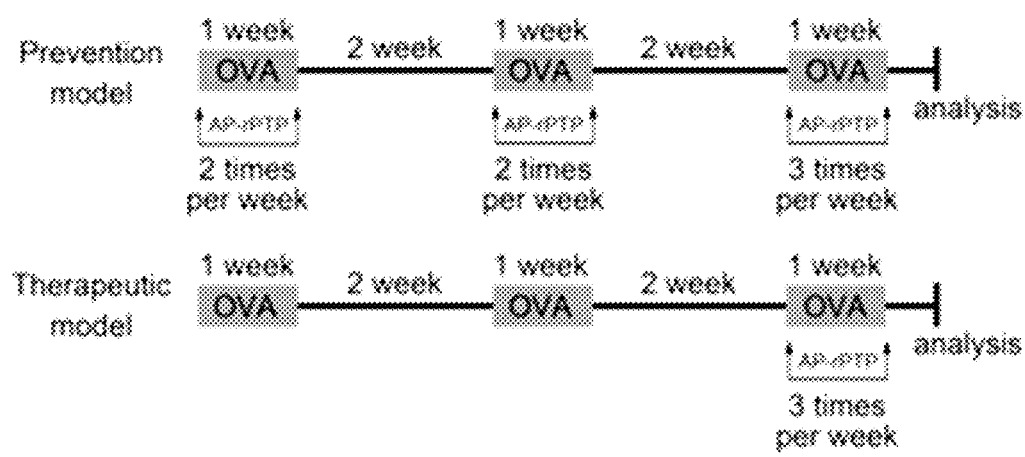
FIG. 42 shows a scheme of an ovalbumin (OVA)-induced chronic dermatitis animal model of Test Example 25.

More specifically, 100 μg of the AP-rPTP protein was administered together with OVA for each application for the investigation of preventive effect, and the AP-rPTP protein was administered only during the final OVA application for the investigation of therapeutic effect (FIG. 42).

More specifically, the back tissue was fixed with 4% formaldehyde for one day and paraffin blocks were prepared after dehydrating tissues by immersing in 30% sucrose for one day. After preparing 6 μm-thick sections, the sections were stained with H&E and observed under an optical microscope. As a result, it was confirmed that the back thickness and inflammation were significantly decreased when treated with the AP-rPTP according to the present disclosure (preventive or therapeutic model), whereas the negative control group (sham) showed hyperproliferation of the epidermis (FIG. 43).

Figure 43:
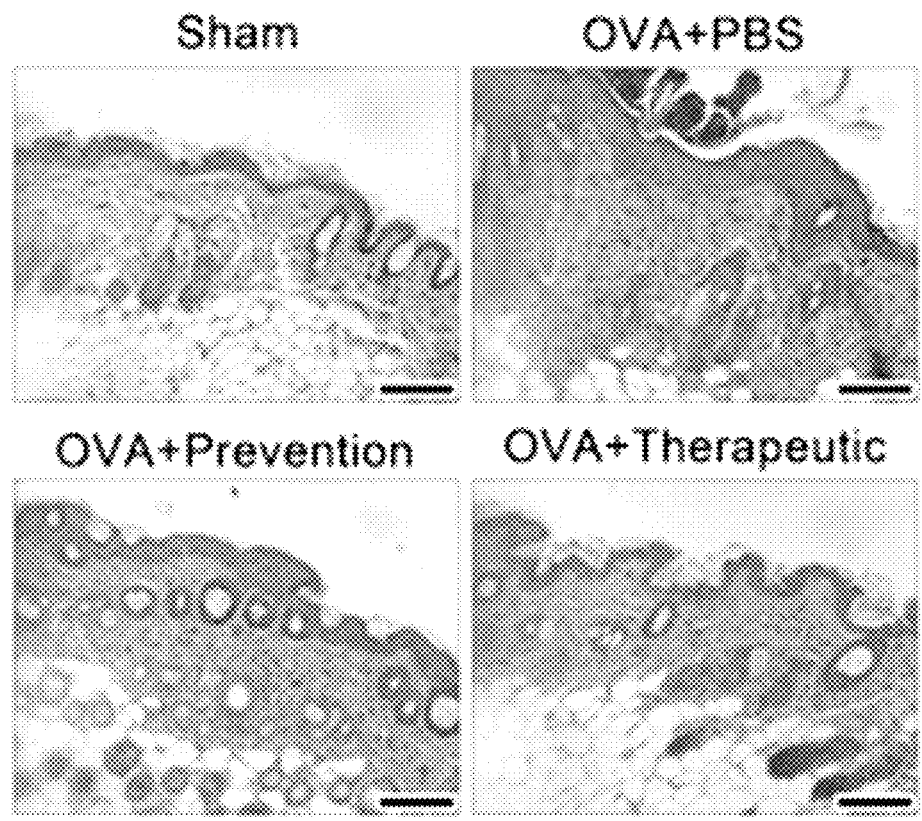
FIG. 43 shows optical microscopic images showing the difference in the ear thickness of a mouse group treated with AP-rPTP and a PBS-treated control mouse group after staining with H&E in Test Example 25.
Figure 44:
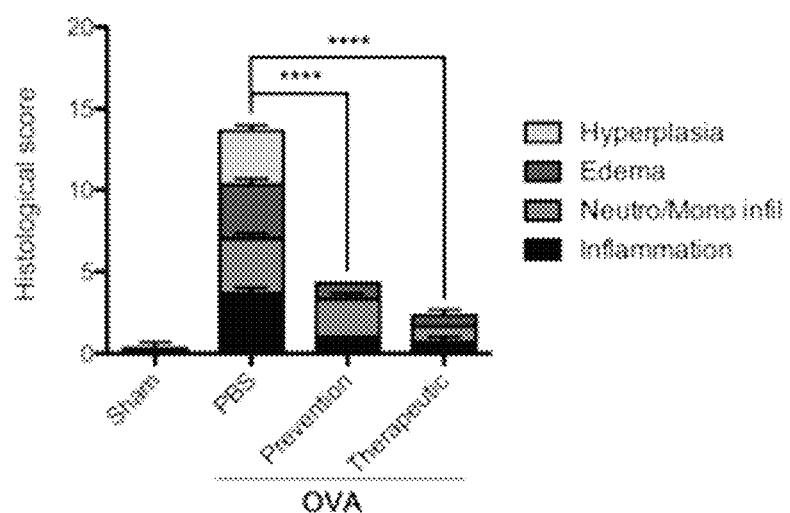
FIG. 44 shows a result of comparing histological scores of H&E staining in FIG. 43.

FIG. 44 shows a result of comparing histological scores of the H&E staining in FIG. 43. It was confirmed that the transdermal treatment of the mouse with the AP-rPTP protein resulted in significantly decreased inflammatory tissues in both the preventive model and the therapeutic model.

FIG. 45 shows a result of comparing the IL-13 mRNA expression level in the skin tissue of the preventive model and the therapeutic model. It can be seen that the treatment with the AP-rPTP of the present disclosure leads to remarkably decreased expression of IL-13 mRNA.

To conclude these results, it can be seen that the inflammations of acute or chronic allergic dermatitis can be significantly reduced through transdermal administration of AP-rPTP using a paper patch. That is to say, the superior preventive and therapeutic effects for dermatitis were confirmed.

Test Example 26: Investigation of Preventive and Therapeutic Effects of AP-rPTP Protein in Imiquimod-Induced Psoriasis-Like Dermatitis Animal Model Because the AP-rPTP protein according to the present disclosure targets inflammatory cytokine signaling and T-cell receptor signaling, it was expected that it would exhibit preventive or therapeutic effect for skin diseases other than allergic inflammations. The following experiment was conducted to demonstrate this.

Figure 47:
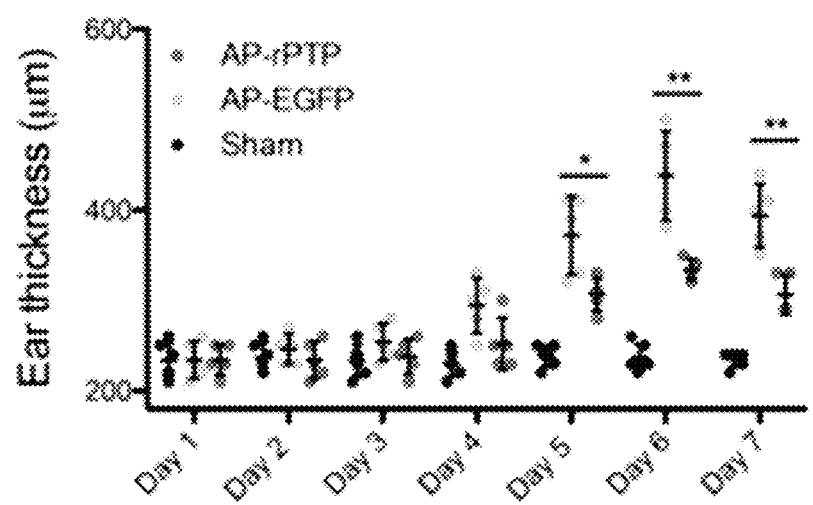
FIG. 47 shows a result of measuring the change in ear thickness of an imiquimod-induced psoriasis-like dermatitis animal model treated with AP-rPTP or AP-EGFP for 6 days in Test Example 26.
Figure 49:
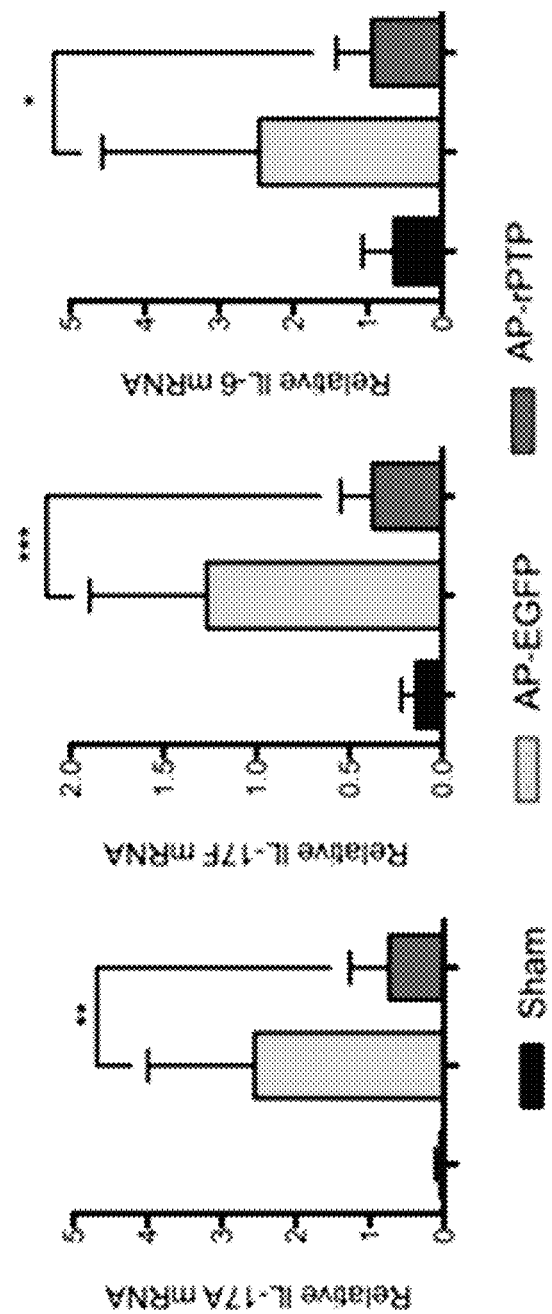
FIG. 49 shows a result of quantifying the mRNA expression level of cytokines (IL-7A, IL-17F, IL-6) in the ear tissue cells of a mouse group treated with AP-rPTP or AP-EGFP and a negative control group (sham) in Test Example 26.
Figure 50:
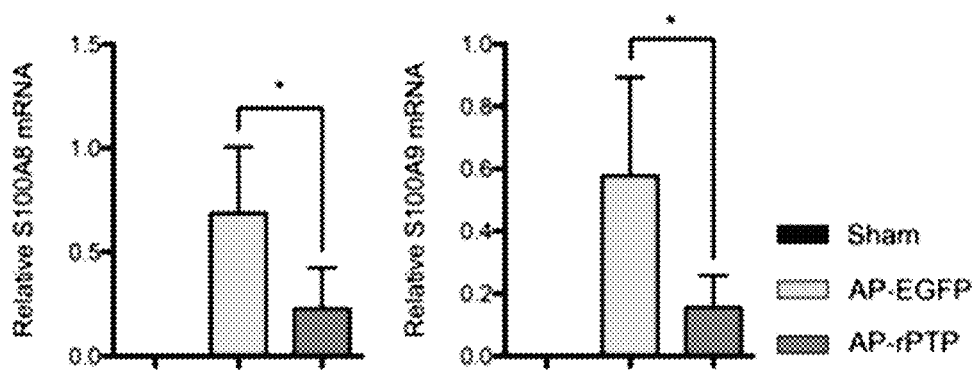
FIG. 50 shows a result of quantifying the mRNA expression level of antimicrobial peptides (S100A8, S100A9) in the ear tissue cells of a mouse group treated with AP-rPTP or AP-EGFP and a negative control group (sham) in Test Example 26.
Figure 51:
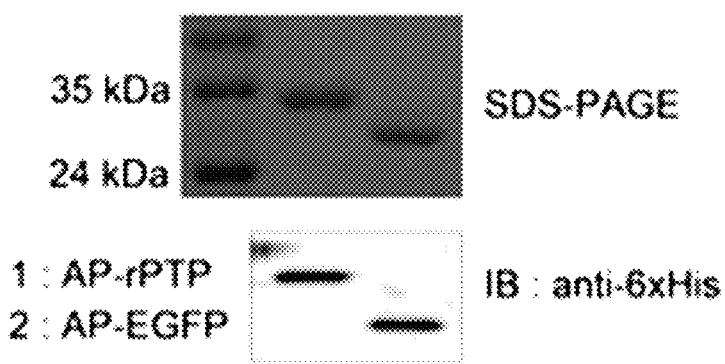
FIG. 51 shows a result of 12% SDS gel electrophoresis of an AP-rPTP protein expressed and purified in Preparation Example 7.

After depilating a 7-week-old male C57BL/6 mouse, 20 mg of Aldara cream (imiquimod 5%) and 100 μg of AP-rPTP or AP-EGFP was applied to the ear using a paper patch for 1 hour every day from the next day (FIG. 46). The ear thickness was measured every day. The result is shown in FIG. 47. Pathological analysis was conducted on day 7. The result is shown in FIGS. 48-50.

FIG. 47 shows the result of measuring the change in the ear thickness of the imiquimod-induced psoriasis-like dermatitis animal model treated with AP-rPTP or AP-EGFP for 6 days.

As seen from FIG. 47, as a result of measuring the ear thickness using a micrometer (Mitutoyo), it was confirmed that the ear thickness of the AP-rPTP-applied mouse group was not significantly increased as compared to the ear thickness of the negative control sham group and that the ear thickness of the AP-rPTP-applied group was decreased as compared to that of the AP-EGFP-treated group.

Figure 48:
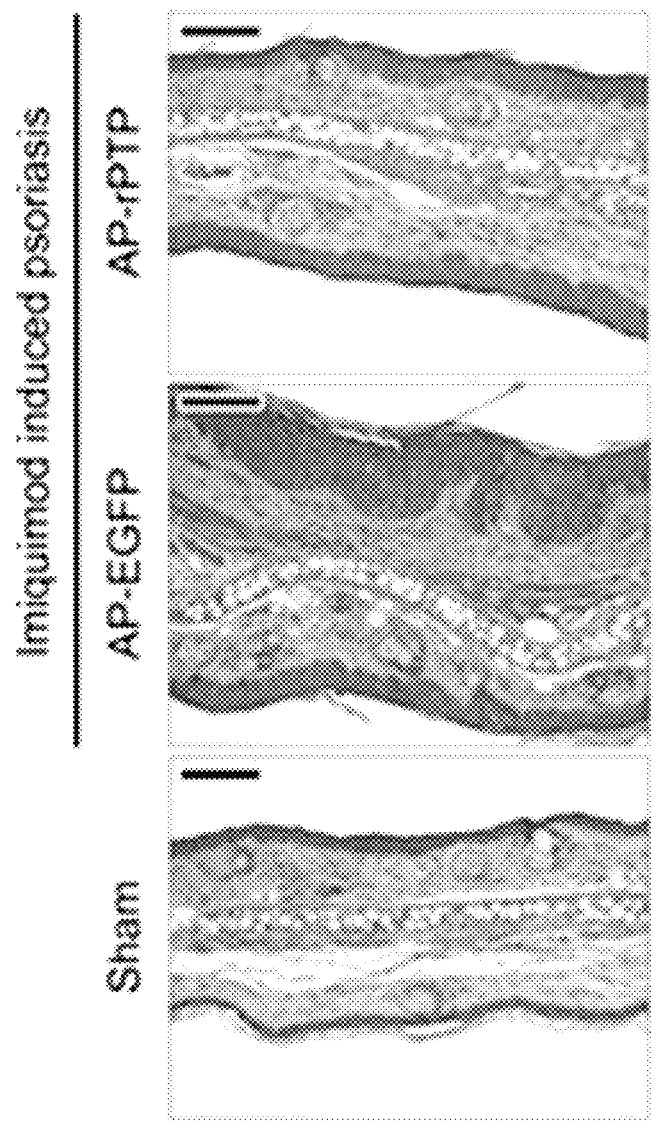
FIG. 48 shows optical microscopic images showing the difference in the ear thickness of a mouse group treated with AP-rPTP or AP-EGFP and a negative control group (sham) after staining with H&E in Test Example 26.

FIG. 48 shows optical microscopic images showing the difference in the ear thickness of the mouse group treated with AP-rPTP or AP-EGFP and the negative control group (sham) after staining with H&E.

As seen from FIG. 48, it was confirmed that the treatment with AP-rPTP resulted in remarkably decreased invasion of inflammatory cells and hyperproliferation of the epidermis as compared to the treatment with AP-EGFP.

FIG. 49 shows a result of quantifying the mRNA expression level of cytokines (IL-7A, IL-17F, IL-6) in the ear tissue cells of the mouse group treated with AP-rPTP or AP-EGFP and the negative control group (sham). FIG. 50 shows a result of quantifying the mRNA expression level of antimicrobial peptides (S100A8, S100A9) in the ear tissue cells of the mouse group treated with AP-rPTP or AP-EGFP and the negative control group (sham).

From the result of investigating the mRNA expression profiles of the ear skin tissues shown in FIG. 49 and FIG. 50, it was confirmed that the expression of IL-17A, IL-17F and IL-6 mRNAs decreased rapidly when AP-rPTP was transdermally administered.

It was also confirmed that the administration of AP-rPTP resulted in distinct decrease of the S100A8 peptide and the S100A9 peptide which are chemotaxic toward neutrophils. To conclude, it can be seen that AP-rPTP exhibits very effective preventive and therapeutic effects for psoriasis-like skin disease when transdermally administered.

INDUSTRIAL APPLICABILITY

A skin-penetrating peptide of the present disclosure and a fusion product in which it is fused with a biologically active substance can be widely applied in cosmetics, medicine, etc.

The invention claimed is:

1. A fusion product comprising:
   a skin-penetrating peptide consisting of a sequence of (X1)n-X2-(cysteine)-(X3)m,
   wherein
   n is an integer from 3 to 14,
   m is an integer from 4 to 14,
   each of X1 and X3 is independently arginine, lysine, or histidine, and
   X2 is alanine, glycine, proline, tryptophan, phenylalanine, leucine, isoleucine, methionine, valine, arginine, or histidine,
   wherein if m is 4, —(X3)m is —KRRR or —RRRR;
   a biologically active substance selected from the group consisting of a protein, a genetic material, a fat, a carbohydrate, and a chemical compound: and
   a fusing moiety linking the skin-penetrating peptide and the biologically active substance,
   with the proviso that when the biologically active substance or the chemical compound is a protein, the skin-penetrating peptide and the biologically active substance are each derived from a peptide of different amino acid sequence, and the skin-penetrating peptide and the chemical compound are each derived from a peptide of different amino acid sequence.

2. The fusion product according to claim 1, wherein the skin-penetrating peptide consists of 9-14 amino acid residues.

3. The fusion product according to claim 2, wherein each of X1 and X3 is independently arginine or lysine.

4. The fusion product according to claim 2, wherein X2 is alanine, tryptophan or arginine.

5. The fusion product according to claim 3, which comprises the amino acid sequence of SEQ ID NO 1, SEQ ID NO 5, SEQ ID NO 8 or SEQ ID NO 12.

6. The fusion product according to claim 1, wherein the biologically active substance is an rPTP peptide comprising the amino acid sequence of SEQ ID NO 20.

7. The fusion product according to claim 1, which comprises the amino acid sequence of SEQ ID NO 19.

8. The fusion product according to claim 1, wherein the linking by the fusing moiety is peptide bonding or chemical bonding.

9. The fusion product according to claim 8, which wherein the chemical bonding is selected from a group consisting of disulfide bonding, diamine bonding, sulfide-amine bonding, carboxyl-amine bonding, ester bonding and covalent bonding.

10. A recombinant expression vector comprising a gene encoding the fusion product according to claim 1.

11. A cosmetic composition comprising the fusion product of a skin-penetrating peptide and a biologically active substance according to claim 1 as an active ingredient.

12. The cosmetic composition according to claim 11, which is prepared into a formulation selected from the group consisting of an emulsion, a cream, an essence, a skin lotion, a liposome, a microcapsule, a composite particle, a shampoo, and a rinse.

13. A pharmaceutical composition for external application to skin, comprising the fusion product of a skin-penetrating peptide and a biologically active substance according to claim 1 as an active ingredient.

14. The pharmaceutical composition for external application to skin according to claim 13, wherein the biologically active substance fused with the skin-penetrating peptide penetrates the stratum corneum of skin.

15. A method for preventing or treating an inflammatory skin disease, comprising a step of applying an effective amount of the pharmaceutical composition for external application to skin according to claim 13 to the skin of a subject.

* * * * *